(12) United States Patent
McGiven et al.

(10) Patent No.: US 11,998,608 B2
(45) Date of Patent: Jun. 4, 2024

(54) POLYSACCHARIDE AND METHODS

(71) Applicants: THE SECRETARY OF STATE FOR ENVIRONMENT, FOOD AND RURAL AFFAIRS, Surrey (GB); THE GOVERNORS OF THE UNIVERSITY OF ALBERTA, Edmonton (CA)

(72) Inventors: John McGiven, Surrey (GB); Laurence Howells, Surrey (GB); Lucy Duncombe, Surrey (GB); David Bundle, Edmonton (CA); Satadru Sekhar Mandal, Edmonton (CA); Susmita Sarkar, Edmonton (CA)

(73) Assignees: THE SECRETARY OF STATE FOR ENVIRONMENT, FOOD AND RURAL AFFAIRS (GB); THE GOVERNORS OF THE UNIVERSITY OF ALBERTA (CA)

( * ) Notice: Subject to any disclaimer, the term of this patent is extended or adjusted under 35 U.S.C. 154(b) by 0 days.

(21) Appl. No.: 17/316,944

(22) Filed: May 11, 2021

(65) Prior Publication Data
US 2021/0330799 A1    Oct. 28, 2021

Related U.S. Application Data

(63) Continuation of application No. 16/347,550, filed as application No. PCT/GB2017/053322 on Nov. 3, 2017, now Pat. No. 11,033,632.

(30) Foreign Application Priority Data

Nov. 4, 2016 (GB) .................................... 1618635

(51) Int. Cl.
| | |
|---|---|
| *A61K 47/61* | (2017.01) |
| *A61K 9/19* | (2006.01) |
| *A61K 39/02* | (2006.01) |
| *C07H 5/06* | (2006.01) |
| *C07H 15/18* | (2006.01) |
| *G01N 33/53* | (2006.01) |
| *G01N 33/569* | (2006.01) |
| *G01N 33/58* | (2006.01) |
| *A61K 39/00* | (2006.01) |

(52) U.S. Cl.
CPC .............. *A61K 47/61* (2017.08); *A61K 9/19* (2013.01); *A61K 39/098* (2013.01); *C07H 5/06* (2013.01); *C07H 15/18* (2013.01); *G01N 33/5308* (2013.01); *G01N 33/56911* (2013.01); *G01N 33/582* (2013.01); *A61K 2039/6031* (2013.01); *G01N 2333/23* (2013.01); *G01N 2400/00* (2013.01)

(58) Field of Classification Search
None
See application file for complete search history.

(56) References Cited

U.S. PATENT DOCUMENTS

| | | | |
|---|---|---|---|
| 4,831,126 A | 5/1989 | Bundle et al. | |
| 5,006,463 A * | 4/1991 | Cherwonogrodzky | ...................... G01N 33/56911 530/387.5 |
| 5,976,820 A | 11/1999 | Jolley et al. | |
| 9,744,245 B2 * | 8/2017 | McGiven | ............... G01N 33/53 |

FOREIGN PATENT DOCUMENTS

| | | |
|---|---|---|
| WO | 2009118570 A2 | 10/2009 |
| WO | 2011030168 A1 | 3/2011 |
| WO | WO 2011/030168 A1 | 3/2011 |

OTHER PUBLICATIONS

Peters, T., & Bundle, D. R. (1987). Synthesis of 4, 6-dideoxy-4-formamido-α-D-mannose containing tri-, tetra-, and penta-saccharides, antigenic determinants of the *Brucella* A and M antigens. Journal of the Chemical Society, Chemical Communications, (21), 1648-1650. (Year: 1987).*

Saksena, R., Chernyak, A., Poirot, E., & Kováč, P. (2003). Conjugating low molecular mass carbohydrates to proteins 2. Recovery of excess ligand used in the conjugation reaction. In Methods in enzymology (vol. 362, pp. 140-159). Academic Press. (Year: 2003).*

(Continued)

*Primary Examiner* — Dale R Miller

(74) *Attorney, Agent, or Firm* — Colleen M. Schaller; Howson & Howson LLP

(57) ABSTRACT

There is provided a molecule comprising a chain of seven or more contiguous units of 4,6-dideoxy-4-acylamido-α-pyranose each pair of units joined by a $C_1$-$C_2$ or a $C_1$-$C_3$ link, the chain having a terminal end and a reducing end, wherein the pyranose ring in the unit of the chain most distal from the reducing end is linked to a cap structure. The cap structure is not a 4,6-dideoxy-4-acylamido-α-pyranose. There are also provided vaccine compositions comprising the molecule and methods of vaccinating an animal against infection by a *Brucella* organism, including methods of distinguishing between a vaccinated and an infected animal. There are further provided novel methods of detecting the presence in a sample of an anti-*Brucella* antibody.

**17 Claims, 12 Dr

(56) References Cited

OTHER PUBLICATIONS

Ariosa-Alvarez, A., Arencibia-Mohar, A., Madrazo-Alonso, O., Garcia-Imia, L., Sierra-Gonzalez, G. . . (1998). Synthesis of the Vibrio Cholerae O1 Ogawa and Inaba Terminal Disaccharides With Dioxolane-Type Spacers and their Coupling to Proteins1. Journal of carbohydrate chemistry, 17(9), 1307-1320. (Year: 1998).*

González, L., Asensio, J. L., Ariosa-Alvarez, A., Vérez-Bencomo, V., & Jiménez-Barbero, J. (1999). Solution conformation and dynamics of the trisaccharide fragments of the O-antigen of Vibrio cholerae O1, serotypes Inaba and Ogawa. Carbohydrate research, 321(1-2), 88-95. (Year: 1999).*

Eichler, E., Kihlberg, J., & Bundle, D. R. (1991). Access to fluorescent probes via allyl glycosides: the synthesis of a*Brucella* trisaccharide epitope linked to a coumarin. Glycoconjugate journal, 8(2), 69-74. (Year: 1991).*

Normand, et al., "tructures of Synthetic O-Antigen Fragments From Serotype 2a Shigella Flexneri in Complex with a Protective Monoclonal Antibody", PNAS, vol. 105, No. 29, Jul. 22, 2008, pp. 9976-9981.

Abdoel, et al., "Rapid Latex Agglutination Test for the Serodiagnosis of Human Brucellosis", Science Direct, Diagnostic Microbiology and Infectious Disease, vol. 57, 2007, pp. 123-128.

Abdoel, et al., "Simple and Rapid Field Tests for Brucellosis in Livestock", Science Direct, Veterinary Microbiology, vol. 130, 2008, pp. 312-319.

Alton, et al., "Techniques for The Brucellosis Laboratory", INRA, Institut National De La Recherche Agronomique (National Institute of Agricultural Research),, 1988, pp. 50-54.

Barrio, et al., "Rough Mutants Defective in Core and O-Polysaccharide Synthesis and Export Induce Antibodies Reacting in an Indirect ELISA With Smooth Lipopolysaccharide and Are Less Effective Than Rev 1 Vaccine Against *Brucella* Melitensis Infection of Sheep", Vaccine, vol. 27, 2009, pp. 1741-1749.

Blasco, et al., "Brucellosis Vaccines and Vaccine Candidates", Veterinary Vaccines for Developing Countries, Chapter 5f., 2016, pp. 1-33.

Bundle, et al., "Definition of *Brucella* A and M Epitopes by Monoclonal Typing Reagents and Synthetic Oligosaccharides", Infection and Immunity, vol. 57, No. 9, Sep. 1989, pp. 2829-2836.

Bundle, et al., "Oligosaccharides and Peptide Displayed on an Amphiphilic Polymer Enable Solid Phase Assay of Hapten Specific Antibodies", Bioconjugate Chem., vol. 25, 2014, pp. 685-697.

Bundle, et al., "Synthesis of Antigenic Determinants of the *Brucella* A Anti-Gen, Utilizing Methyl 4-Azido-4, 6-Dideoxy-a-D-Manno-Pyranoside Efficiently Derived from D-Mannose", Carbohydrate Research, vol. 174, 1988, pp. 239-251.

Caroff, et al., "Structure of the 0-Chain of the Phenol-Phase Soluble Cellular Lipopolysaccharide of Yersinia Enterocolitica Serotype 0:9", Eur. J. Biochem., vol. 139, 1984, pp. 195-200.

Cloeckaert, et al., "0-chain Expression in the Rough *Brucella melitensis* Strain B115: Induction of 0-Polysaccharide-Specific Monoclonal Antibodies and Intracellular Localization Demonstrated by Immunoelectron Microscopy", Journal of General Microbiology, vol. 138, 1992, pp. 1211-1219.

Corbel, "Recent Advances in the Study of *Brucella* Antigens and their Serological Cross-Reactions", The Veterinary Bulletin, vol. 55, No. 12, Dec. 1985, pp. 927-942.

Ducrotoy, et al., "A Review of the Basis of the Immunological Diagnosis of Ruminant Brucellosis", Veterinary Immunology and Immunopathology, 2016, 73 pages.

Eis, et al., "An Improved Synthesis of D-Perosamine and Some Derivatives", Carbohydrate Research, vol. 176, 1988, pp. 316-323.

Ganesh, et al., "Molecular Recognition of *Brucella* A and M Antigens Dissected by Synthetic Oligosaccharide Glycoconjugates Leads to a Disaccharide Diagnostic for Brucellosis", Journal of the American Chemical Society, vol. 136, 2014, pp. 16260-16269.
GB1618635.5 , "Search Report received for GB Patent Application No. GB1618635.5, dated Aug. 21, 2017", dated Aug. 21, 2017, 2 pages.
Gonzalez , et al., "Brucellosis Vaccines: Assessment of *Brucella melitensis* Lipopolysaccharide Rough Mutants Defective in Core and O-Polysaccharide Synthesis and Export", Plos One, vol. 3, Issue 7, Jul. 2008, pp. 1-15.
Goodwin , et al., "Brucellosis Vaccines for Livestock", Veterinary Immunology and Immunopathology, 2016, 30 pages.
Grillo , et al., "Increases of Efficacy as Vaccine Against *Brucella abortus* Infection in Mice by Simultaneous Inoculation With Avirulent Smooth Bvrs/Bvrr and Rough Wbka Mutants", Vaccine, vol. 24, 2006, pp. 2910-2916.
Guiard , et al., "Design and Synthesis of a Universal Antigen to Detect Brucellosis", Angew Chem Int Ed Engl., vol. 52, 2013, pp. 7181-7185.
Idrissi , et al., "Comparison of the Efficacy of *Brucella abortus* Strain RB51 and *Brucella melitensis* Rev. 1 Live Vaccines Against Experimental Infection With Brucella Melitensis in Pregnant Ewes", Rev. Sci. Tech., vol. 20, No. 3, 2001, pp. 741-747.
Kubler-Kielb , et al., "Reinvestigation of the Structure of *Brucella* O-Antigens", Carbohydrate Research, vol. 378, Aug. 30, 2013, pp. 144-147.
Kubler-Kielb , et al., "The Study of the Core Part and Non-Repeating Elements of the O-Antigen of *Brucella* Lipopolysaccharide", Carbohydrate Research, vol. 366, 2013, pp. 33-37.
Lipinski , et al., "A β-Mannan Trisaccharide Conjugate Vaccine Aids Clearance of Candida Albicans in Immunocompromised Rabbits", Vaccine, vol. 30, 2012, pp. 6263-6269.
Mancilla , et al., "Genomic Island 2 Is an Unstable Genetic Element Contributing to *Brucella* Lipopolysaccharide Spontaneous Smooth-to-rough Dissociation", Journal of Bacteriology, vol. 192, No. 24, Dec. 2010, pp. 6346-6351.
Mandal , et al., "Novel Solutions for Vaccines and Diagnostics to Combat Brucellosis", ACS Cent Sci., vol. 3, 2017, pp. 224-231.
Mandal , et al., "Synthetic Glycoconjugates Characterize the Fine Specificity of *Brucella* A and M Monoclonal Antibodies", Organic & Biomolecular Chemistry, 2017, 10 pages.
Mawas , et al., "Immunogenicity in a Mouse Model of a Conjugate Vaccine Made With a Synthetic Single Repeating Unit of Type 14 Pneumococcal Polysaccharide Coupled to CRM197", Infection and Immunity, vol. 70, No. 9, Sep. 2002, pp. 5107-5114.
McGiven , et al., "Improved Serodiagnosis of Bovine Brucellosis by Novel Synthetic Oligosaccharide Antigens Representing the Capping M Epitope Elements of *Brucella* O-Polysaccharide", Journal of Clinical Microbiology, vol. 53, No. 4, Apr. 2015, pp. 1204-1210.
McGiven , "New Developments in the Immunodiagnosis of Brucellosis in Livestock and Wildlife", Rev Sci Tech., vol. 32, No. 1, 2013, pp. 163-176.
Meikle , et al., "Fine Structure of A and M Antigens From *Brucella* Biovars", Infection and Immunity, vol. 57, No. 9, Sep. 1989, pp. 2820-2828.
Monreal , et al., "Characterization of *Brucella abortus* O-Polysaccharide and Core Lipopolysaccharide Mutants and Demonstration That a Complete Core Is Required for Rough Vaccines to Be Efficient Against *Brucella abortus* and *Brucella ovis* in the Mouse Model", Infection and Immunity, vol. 71, No. 6, Jun. 2003, pp. 3261-3271.
Montaraz , et al., "Protection Against *Brucella abortus* in Mice With O-Polysaccharide-Specific Monoclonal Antibodies", Infection and Immunity, vol. 51, No. 3, Mar. 1986, pp. 961-963.
Moriyon , et al., "Rough Vaccines in Animal Brucellosis: Structural and Genetic Basis and Present Status", Vet Res., vol. 35, 2004, pp. 1-38.
Nasir , et al., "Fluorescence Polarization: An Analytical Tool for Immunoassay and Drug Discovery", Combinatorial Chemistry & High Throughput Screening, vol. 2, No. 4, 1999, pp. 177-190.
Nielsen , et al., "Enzyme-linked Immunosorbent Assay for Differentiation of the Antibody Response of Cattle Naturally Infected With *Brucella abortus* or Vaccinated With Strain 19", American Journal of Veterinary Research, vol. 50, No. 1, Jan. 1989, pp. 5-9.
Ogawa , et al., "Synthesis of the Dodecasaccharide Fragment Representing the O-Polysaccharide of Vibrio Cholerae 0:1, Serotype

(56) References Cited

OTHER PUBLICATIONS

Ogawa, Bearing an Aglycon Offering Flexibility for Chemical Linking to Proteins", Glycoconjugate Journal, vol. 14, 1997, pp. 433-438.

Oie, "Brucellosis (*Brucella abortus*, B. Melitensis And B. Suis) (Infection with B. Abortus, B. Melitensis and B. Suis)", Chapter 2.1.4., May 2016, pp. 1-44.

PCT/GB2017/053322, "International Preliminary Report on Patentability received for PCT Patent Application No. PCT/GB2017/053322, dated May 16, 2019", dated May 16, 2019, 13 pages.

PCT/GB2017/053322, "International Search Report and Written Opinion received for PCT Patent Application No. PCT/GB2017/053322, dated Jul. 10, 2018", dated Jul. 10, 2018, 21 pages.

Perez-Sancho, et al., "Evaluation of the Immunogenicity and Safety of *Brucella melitensis* B115 Vaccination in Pregnant Sheep", Vaccine, vol. 32, 2014, pp. 1877-1881.

Pouillot, et al., "The Brucellin Skin Test as a Tool to Discriminate False Positive Serological Reactions in Bovine Brucellosis", Vet Res., vol. 28, 1997, pp. 365-374.

Rhodes, et al., "A Blocking Elisa for the Detection of Specific Antibodies to Bovine Respiratory Syncytial Virus", J Vet Diagn Invest, vol. 1, 1989, pp. 324-328.

Schurig, et al., "Biological Properties of RB51; a Stable Rough Strain of *Brucella abortus*", Veterinary Microbiology, vol. 28, 1991, pp. 171-188.

Stefanetti, et al., "Impact of Conjugation Chemistry on the Immunogenicity of S. Typhimurium Conjugate Vaccines", Vaccine, vol. 32, 2014, pp. 6122-6129.

Svenson, et al., "Artificial *Salmonella* Vaccines: *Salmonella* Typhimurium 0-Antigen-Specific Oligosaccharide-Protein Conjugates Elicit Protective Antibodies in Rabbits and Mice", Infection and Immunity, vol. 32, No. 2, May 1981, pp. 490-496.

Vemulapalli, et al., "Complementation of *Brucella abortus* RB51 With a Functional wboA Gene Results in O-Antigen Synthesis and Enhanced Vaccine Efficacy but No Change in Rough Phenotype and Attenuation", Infection and Immunity, vol. 68, No. 7, Jul. 2000, pp. 3927-3932.

Verez-Bencomo, et al., "A Synthetic Conjugate Polysaccharide Vaccine Against Haemophilus Influenzae Type B", Science, vol. 305, Jul. 23, 2004, pp. 522-525.

Westphal, et al., "Über Die Extraktion Von Bakterien Mit Phenol/Wasser", Jan. 14, 1952, pp. 148-155.

Zaccheus, et al., "The Epitopic and Structural Characterization of *Brucella* Suis Biovar 2 O-Polysaccharide Demonstrates the Existence of a New M-Negative C-Negative Smooth *Brucella serovar*", PLOS One, vol. 8, Issue 1, Jan. 2013, pp. 1-7.

Duncombe, et al. "The Tip of *Brucella* O-Polysaccharide Is a Potent Epitope in Response to Brucellosis Infection and Enables Short Synthetic Antigens to Be Superior Diagnostic Reagents", Microorganisms, vol. 10, No. 708, 2022, 19 pages.

Non-Final Office Action in U.S. Appl. No. 16/347,550, dated Jun. 22, 2020.

Response to Non-Final Office Action in U.S. Appl. No. 16/347,550, dated Nov. 18, 2020.

English Translation of Office Action in Eurasian Patent Application No. 202290694, dated Nov. 7, 2023.

* cited by examiner

POLYSACCHARIDE AND METHODS

CROSS REFERENCE TO RELATED APPLICATIONS

This application is a continuation of U.S. patent application Ser. No. 16/347,500 filed May 6, 2019 which is a national phase filing under 35 U.S.C. § 371 of International Application No. PCT/GB2017/053322 filed Nov. 3, 2017 which claims priority from GB1618635.5 filed Nov. 4, 2016, the entire contents of which are hereby incorporated by reference herein.

FIELD OF THE INVENTION

The invention relates to a polysaccharide molecule which is useful as a component of a vaccine for vaccinating animals against infection by *Brucella* organisms, such that a DIVA (Differentiating Infected from Vaccinated Animals) test is possible. The invention also relates to novel diagnostic methods for detection of infection by a *Brucella* organism.

BACKGROUND

Brucellosis is one of the world's most significant zoonotic diseases and is caused by bacteria of the genus *Brucella*. These are non-spore forming coccobacillary rods with a cell wall characteristic of Gram-negative bacteria which includes peptidoglycans, outer membrane proteins and lipopolysaccharide (LPS). The species *B. abortus, B. melitensis* and *B. suis* cause the greatest animal and human health impacts. The LPS of field strains of these species possess O-polysaccharide (OPS), which protrudes from the cell wall, dominates the surface and alters the morphology of colonies, giving rise to their description as 'smooth' species and as strains that possess smooth (s) LPS. Strains that do not have OPS on their surface are described as 'rough' and have rough (r) LPS. The main feature of the disease in livestock is reproductive failure, which is most evident through abortion and male infertility. This results in large losses in animal production and spread of disease to humans. Otherwise, many animals will appear outwardly healthy.

The impact of the disease is felt in most regions of the globe. Even in the absence of disease, it is important to conduct surveillance in order to maintain a disease-free status. In most countries the disease persists, or may be re-emerging, and significant wildlife reservoirs exist.

Control of endemic brucellosis is only achievable via mass vaccination. Test and slaughter programmes at high levels of disease prevalence are unaffordable, unsustainable and unpalatable. After a period of mass vaccination, further downward pressure on prevalence can be attained by vaccination of replacement animals. In practice, however, effective vaccination may be difficult to achieve with sufficient coverage. The current vaccines exert insufficient protection to eliminate disease. Therefore, to achieve disease elimination, a test and slaughter programme, reliant upon serology, is required. Serodiagnosis is the key tool in maintaining disease freedom and for facilitating trade in livestock, as well as for epidemiological investigations. Other methods of disease detection, such as direct culture of *Brucella* and PCR for detection of *Brucella* specific DNA, are insufficiently sensitive, more expensive and, for culture, carry significant health risks Immunodiagnosis via cell mediated reactions are also insufficiently effective due to low diagnostic sensitivity and reactions due to vaccination. (Pouillot et al (1997) Vet Res 28:365-374).

The currently universally recognised vaccines for brucellosis are *B. abortus* S19 and *B. abortus* RB51 for use in cattle, with *B. melitensis* Rev1 for use in sheep and goats. All have significant and well documented flaws (Blasco et al (2015) Veterinary Vaccines for Developing Countries. FOA, Rome). For example, they are all live (requiring the use of a cold chain for distribution), possess residual virulence in livestock and are pathogenic to humans *B. abortus* RB51 and *B. melitensis* Rev1 both possess resistance to antibiotics that are important in the treatment of human disease. *B. abortus* S19 and *B. melitensis* Rev1 may lose the ability to synthesise OPS, which results in a loss of protective efficacy. This is particularly problematic with *B. melitensis* Rev1 (Mancilla et al (2010) Journal of Bacteriology 192:6346-6351).

*B. abortus* S19 and *B. melitensis* Rev1 are both smooth stains and, therefore, their use results in the induction of antibodies that react in conventional serological tests for *Brucella* infection. This is because the serodiagnostic antigens used in these tests rely upon the presence of OPS to provide them with excellent sensitivity, whereas antigens without OPS are ineffective diagnostics (McGiven (2013) Rev Sci Tech 32:163-176). This makes the differentiation of infected and vaccinated animals impossible in many circumstances. This presents a significant barrier to effective control, as it makes it extremely difficult to effectively use vaccination alongside a test and removal strategy based on serodiagnosis.

The rough strain *B. abortus* RB51 was developed to alleviate the serological reactions due to vaccination with *B. abortus* S19 in cattle. This rough strain was developed by passage on rifampicin impregnated growth media (Schurig et al (1991) Vet Microbiol 28:171-188). Of the many mutations spontaneously generated by the antibiotic, several affect OPS synthesis. The strain can neither synthesise OPS nor, when synthesis is complemented by gene addition, export it to the cell surface (Vemulapalli et al (2000) Infect Immun 68). The use of this vaccine, therefore, does not result in anti-OPS antibodies and it has limited interference in conventional serology.

Despite this advantage of *B. abortus* RB51, its adoption has been far from universal. Its protective efficacy and safety in cattle compared to *B. abortus* S19 is contested (Moriyon et al (2004) Veterinary Research 35:1-38). In murine models of protection, the primary animal model, it has been shown to be significantly less protective than *B. abortus* S19 (Monreal et al (2003) Infection and Immunity 71:3261-3271).

Attempts to develop *B. abortus* RB51 as a vaccine for brucellosis in sheep and goats have failed to show protection (Idrissi et al (2001) Rev Sci Tech 20:741-747). Rough *B. melitensis* strains have also been evaluated as vaccines in sheep but have shown insufficient protective efficacy (Barrio et al (2009) Vaccine 27:1741-1749). A rough *B. melitensis* strain B115 has been applied to sheep but was shown to be insufficiently safe, with a high abortion rate reported (Perez-Sancho et al (2014) Vaccine 32:1877-1881). Studies in mice have previously shown that *B. melitensis* B115 induces anti-OPS antibodies due to the presence of cytoplasmic OPS (Cloeckaert et al (1992) J Gen Microbiol 138:1211-1219). A comprehensive study of the protective capability of rough *B. melitensis* mutants to protect against *B. melitensis* challenge in mice concluded that rough variants that did not synthesise OPS were significantly less protective than their smooth counterparts (Gonzalez et al (2008) PLoS ONE 3:e2760).

Anti-OPS antibodies have been persistently shown to be protective in the mouse model of brucellosis (Montaraz et al (1986) Infection and Immunity 51:961-963). A combination of humoral and cell mediated protection has been shown to have synergistic effects (Grilló et al (2006) Vaccine 24:2910-2916) and provides optimal protection. Although the data in the natural host is less conclusive, the evidence based on the relative properties of smooth and rough strains, as described above, is compelling, particularly for small ruminants The search for improved *Brucella* vaccines is a recognised necessity yet, despite decades of effort, no new vaccines have been adopted for use in livestock since the introduction of *B. abortus* RB51. Research into recombinant protein subunit vaccines, *Brucella* protein expression vectors or DNA vaccines have yet to have any impact in the field. Attenuated smooth *Brucella* mutants run up against the same issues of antibody induction as *B. abortus* S19 and *B. melitensis* 16M and have not demonstrated sufficient additional advantages in other regards such as safety and efficacy in order to be taken forward from the research laboratory.

As discussed, effective new developments have been severely hampered by the persistently and seemingly unresolvable issue that OPS seems required both for optimal vaccine protection in livestock and for effective serodiagnosis. This has been a longstanding barrier against the development of an optimally protective vaccine which may be utilised in a DIVA (Differentiating Infected from Vaccinated Animals) vaccine-and-test regime.

The main structural element within the *Brucella* OPS is a homopolymer of 4,6-dideoxy-4-formamido-mannopyranosyl (D-Rha4NFo) units that are variably $\alpha(1\rightarrow 2)$ and $\alpha(1\rightarrow 3)$ linked (Meikle et al (1989) Infect Immun 57:2820-2828). The proportion of each linkage type in different strains of *Brucella* appears to vary from 0 to 20% frequency of $\alpha(1\rightarrow 3)$ linkage types with the remainder being $\alpha(1\rightarrow 2)$ types. Notably, only the *B. suis* biovar 2 type strain has been found to be devoid of $\alpha(1\rightarrow 3)$ links (Zaccheus et al (2013) PLoS One 8:e53941).

As discussed extensively within WO2014/170681 (the contents of which are incorporated by reference herein in their entirety), the relative proportions and distribution of $\alpha(1\rightarrow 2)$ and $\alpha(1\rightarrow 3)$ linkages within the *Brucella* and *Y. enterocolitica* O:9 homopolymeric OPS create distinct, but not necessarily completely described, antibody binding epitopes. In *Brucella*, there are three different antigenic epitopes which can be found in the OPS for which there has been firm structural evidence (Bundle et al (1989) Infect Immun 57:2829-2836) as summarised in Table 1:

TABLE 1

| Name of epitope | Number of perosamines | Characteristics | Present in which OPS |
|---|---|---|---|
| C/Y | 3 to 4 | N-formyl perosamines are exclusively joined by $\alpha(1\rightarrow 2)$ linkages | All smooth *Brucella* strains and also *Y. enterocolitica* O:9 |
| A | 5 or more | N-formyl perosamines are joined by $\alpha(1\rightarrow 2)$ linkages | Predominantly within all A-dominant *Brucella* strains and also *Y. enterocolitica* O:9 |

TABLE 1-continued

| Name of epitope | Number of perosamines | Characteristics | Present in which OPS |
|---|---|---|---|
| M | 2-6 | At least one $\alpha(1\rightarrow 3)$ link present with zero, one or two adjacent $\alpha(1\rightarrow 2)$ linkages; location of $\alpha(1\rightarrow 3)$ link within epitope undefined | Predominantly within M-dominant OPS *Brucella* strains but also, to a lesser extent, A-dominant strains. Not found in *Y. enterocolitica* O:9 or *B. suis* biovar 2 |

Nielsen et al (Nielsen et al (1989) Am J Vet Res 50:5-9) suggested the presence of a further epitope in the non-reducing end region of the OPS. These authors speculated that antibodies to this theoretical epitope were generated during vaccination with *B. abortus* S19.

The *Brucella* OPS is formed as a D-Rha4NFo block copolymer (Kubler-Kielb & Vinogradov (2013) Carbohydrate Research 378:144-147) with two polymeric elements combined into one molecule, along with three non-D-Rha4NFo sugars at the reducing end forming the adaptor and primer regions (Kubler-Kielb & Vinogradov (2013) Carbohydrate Research 366:33-37). The first D-Rha4NFo polymeric element, found at the reducing end, is a sequence of D-Rha4NFo units that are all $\alpha(1\rightarrow 2)$ linked. This sequence is linked to the second polymeric element, of one or more tetrasaccharide D-Rha4NFo units containing a central $\alpha(1\rightarrow 3)$ link, the linkages being otherwise $\alpha(1\rightarrow 2)$. As mentioned above, the presence of the $\alpha(1\rightarrow 3)$ link constitutes the specific feature of the "M epitope". The OPS of M dominant strains of *Brucella* have several multiples of these tetrasaccharide units coupled to the $\alpha(1\rightarrow 2)$ linked polymer. The OPS of A dominant strains contain one or two of these terminal tetrasaccharides coupled to a longer $\alpha(1\rightarrow 2)$ linked polymer. Consequently, an $\alpha(1\rightarrow 3)$ link is present near the tip of each OPS molecule whether it derives from an A or an M dominant strain of *Brucella*.

The significance of this linkage detail is that it substantially alters the shape of the OPS and affects antibody binding. This has been shown in numerous studies using monoclonal antibodies (mAbs) (Bundle et al (1989) Infect Immun 57:2829-2836) and the absorbed monospecific polyclonal sera that is used within the classical biotyping scheme for *Brucella* to classify strains as either A, M or mixed A and M serotypes (Alton et al (1994) INRA Editions).

Infection with other Gram-negative bacteria which possess similar OPS structures may induce antibodies that cross react with *Brucella* OPS (Corbel (1985) Vet. Bull. 55:927-942) giving rise to False Positive Serological Reactions (FPSRs). The most well cited of these is *Yersinia enterocolitica* O:9 as this possesses a homopolymer that consists of exclusively $\alpha(1\rightarrow 2)$ linked D-Rha4NFo units (Caroff et al (1984) Eur J Biochem 139:195-200).

The invention disclosed in WO2014/170681 related to various synthetic oligosaccharide structures based on the structure of *Brucella* OPS. The structures all contain at least two 4,6-dideoxy-4-formamido-D-mannopyranose units and comprise at least one $\alpha(1\rightarrow 3)$ linkage between pairs of units. Depending on the number of units included in the oligosaccharide, the structure may be used as a "universal" antigen, capable of detecting antibodies raised against any *Brucella* or *Y. enterocolitica* OPS, or as a "M-specific" antigen, capable of detecting only antibodies raised against a *Brucella* OPS comprising $\alpha(1\rightarrow 3)$ linkages (McGiven et al (2015) Journal of Clinical Microbiology). This enabled, for the first time, a user to distinguish between an animal infected with *Brucella* as opposed to an animal which might be infected with either *Brucella* or the *Y. enterocolitica* O:9.

SUMMARY OF THE INVENTION

The inventors have newly identified and characterised a further important structural feature of the *Brucella* OPS, which enables the provision, for the first time, of a vaccine which can be used within a DIVA testing system, as described herein.

As discussed further below, the initial work described herein also led to the evaluation of the serodiagnostic properties of several synthetic oligosaccharide structures that would otherwise not have been considered. Some of these have demonstrated surprisingly superior properties in serodiagnostic assays for brucellosis.

According to a first aspect of the invention, there is provided a molecule comprising a chain of seven or more contiguous units of 4,6-dideoxy-4-acylamido-α-pyranose of Formula 1, adjacent units being joined by a $C_1$-$C_2$ or a $C_1$-$C_3$ glycosidic link, the chain having a terminal end and a reducing end, wherein the pyranose ring in the unit of the chain most distal from the reducing end is linked to a cap structure, for example linked from $C_2$ or $C_3$. In all aspects and embodiments of the invention disclosed herein, the cap structure is not a 4,6-dideoxy-4-acylamido-α-D-pyranose (i.e., is not a 4,6-dideoxy-4-acylamido-α-D-mannopyranose or a 4,6-dideoxy-4-acylamido-α-D-glucopyranose) linked to the remainder of the molecule via its $C_1$.

The term "4,6-dideoxy-4-acylamido-α-pyranose", as used throughout this specification, indicates a 4,6-dideoxy-4-acylamido-α-pyranose as defined in Formula 1 below.

The cap structure serves to disrupt an epitope which the inventors have newly identified in *Brucella* OPS, determining it to be dependent on the presence of an intact single 4,6-dideoxy-4-acylamido-α-D-mannopyranose unit at the terminal end (i.e., the non-reducing end) of the polymer. The cap structure may, therefore, be any structure which disrupts the structure of the terminal 4,6-dideoxy-4-acylamido-α-pyranose of Formula 1, particularly by removing or replacing the —OH groups on $C_2$ and $C_3$ ($R_{10}$ and $R_{11}$ in Formula 1 below); specific non-limiting examples are further described below. Such disruption may be determined by raising antibodies against a molecule believed to be in accordance with the invention and determining whether the antibodies are capable of binding to a universal antigen and to a DIVA antigen as described in more detail below. If the antibodies are capable of binding to a universal antigen but not to a DIVA antigen, the molecule is one in which the tip epitope has been disrupted, i.e., it comprises a cap structure as described herein.

A unit of 4,6-dideoxy-4-acylamido-α-pyranose as referred to throughout this specification has the structure Formula 1:

Formula 1 wherein $R_1$ is as defined below, $R_{10}$ and $R_{11}$ are independently selected from —OH or a 4,6-dideoxy-4-acylamido-α-pyranose (when the 4,6-dideoxy-4-acylamido-α-pyranose unit of Formula 1 is located in a polymer at a non-terminal position where it is linked via its $C_2$ or $C_3$ to a further 4,6-dideoxy-4-acylamido-α-pyranose unit, as described in more detail below); $R_{12}$ is an acylamido selected from formamido, acetylamido, propionamido and butyramido; $R_{13}$ is —CH$_3$. The numbering of the carbon atoms in this structure is also shown above.

In any given 4,6-dideoxy-4-acylamido-α-pyranose unit, group $R_1$ may be a saccharide molecule such as another 4,6-dideoxy-4-acylamido-α-pyranose unit, so that the single unit appears as Formula 1a, being linked to neighbouring sugar:

Formula 1a

Alternatively, if $R_1$ is at the "reducing end" of a polysaccharide chain, $R_1$ may be H or an alkyl group such as methyl or ethyl, or may be a non-perosamine sugar, or may be any other non-perosamine molecule such as a protein, a lipid, a macromolecule (any of which may join (i.e., link) to a larger entity such as a whole cell), or a linker group as used herein to link a polysaccharide to an entity such as a vaccine carrier. If the unit is in the form of Formula 1a, linked to a neighbouring sugar via $C_1$, it may be referred to as 4,6-dideoxy-4-acylamido-α-pyranosyl. The term "pyranose" as used throughout this specification, encompasses both the pyranose and pyranosyl arrangements. Likewise, reference in this specification to "mannopyranose" may refer to either mannopyranose or mannopyranosyl and reference to "glucopyranose" may refer to either glucopyranose or glucopyranosyl.

The "reducing end" of a chain of 4,6-dideoxy-4-acylamido-α-pyranose units is, therefore, the end at which there is a 4,6-dideoxy-4-acylamido-α-pyranose where $C_1$ is not linked to a further 4,6-dideoxy-4-acylamido-α-pyranose. In this case, $R_1$ may be (by way of example) H or methyl, a non-perosamine sugar or another non-perosamine molecule as described above.

The "terminal end" of a chain of 4,6-dideoxy-4-acylamido-α-pyranose units is the end having the unit in the chain most distal from the reducing end. By way of example and further explanation, the "terminal end" and "reducing end" are indicated in Structure I below and equivalent terminology applies to any polymer of 4,6-dideoxy-4-acylamido-α-pyranose units discussed herein.

Throughout this specification, a "$C_1$-$C_2$ glycosidic link" (or "$C_1$-$C_2$ link") is an α(1→2) link between two pyranose rings and a "$C_1$-$C_3$ glycosidic link" (or "$C_1$-$C_3$ link") is an α(1→3) link between two pyranose rings.

In any embodiment of the invention described herein, any 4,6-dideoxy-4-acylamido-α-pyranose within the chain may be 4,6-dideoxy-4-formamido-α-mannopyranose, for example, 4,6-dideoxy-4-formamido-α-D-mannopyranose. As described above, this forms the OPS of *Brucella* and *Y. enterocolitica* organisms. 4,6-dideoxy-4-formamido-α-D-mannopyranose has the structure shown below as Formula 1b:

Formula 1b

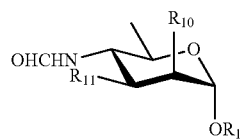

wherein $R_1$, $R_{10}$ and $R_{11}$ are as defined above.

Alternatively, any (or all) 4,6-dideoxy-4-acylamido-α-pyranose within the chain may be 4,6-dideoxy-4-formamido-α-glucopyranose, for example, 4,6-dideoxy-4-formamido-α-D-glucopyranose. Units of 4,6-dideoxy-4-formamido-α-mannopyranose and of 4,6-dideoxy-4-formamido-α-glucopyranose may both be included in the molecule according to the invention.

Units of 4,6-dideoxy-4-formamido-α-D-mannopyranose exist within the natural OPS polymers in one of three states. They may be located at the reducing end, at the terminal end, or in between. If a unit is at the reducing end then it is linked to a further 4,6-dideoxy-4-formamido-α-D-mannopyranose via $C_2$ or $C_3$ and, in the OPS, it is also linked to a non-perosamine sugar via the reducing carbon ($C_1$). If the 4,6-dideoxy-4-formamido-α-D-mannopyranose is located between the reducing and terminal ends then it is bound to two adjacent 4,6-dideoxy-4-formamido-α-D-mannopyranose units, one via the reducing carbon ($C_1$) and one via $C_2$ or $C_3$. Finally, if the 4,6-dideoxy-4-formamido-α-D-mannopyranose is at the terminal end, it is linked to one adjacent 4,6-dideoxy-4-formamido-α-D-mannopyranose only, via its reducing ($C_1$) carbon. There is no other linkage and carbons 2 and 3 both carry hydroxyls rather than having additional sugars linked to them. Therefore, the terminal sugar unit is unique within the polymer, as it is the only sugar that has unsubstituted hydroxyls on both $C_2$ and $C_3$.

As discussed further below and forming the basis of the present invention, the absence of any additional sugars attached to this terminal 4,6-dideoxy-4-formamido-α-D-mannopyranose unit in the OPS makes it particularly accessible to molecules of the immune system, which the inventors have exploited to provide a molecule which can be used effectively as a vaccine within a disease control system which also comprises use of a DIVA assay described herein. Therefore, the invention disclosed herein relates to a 4,6-dideoxy-4-formamido-α-D-pyranose polymer (especially a 4,6-dideoxy-4-formamido-α-D-mannopyranose polymer) which does not have a 4,6-dideoxy-4-formamido-α-D-pyranose unit (i.e., a 4,6-dideoxy-4-formamido-α-D-mannopyranose or 4,6-dideoxy-4-formamido-α-D-glucopyranose) at the terminal end.

The cap structure included in the molecule according to the invention is linked to the 4,6-dideoxy-4-formamido-α-D-pyranose unit in the molecule which is most distal from the reducing end of the chain, i.e., which is at the terminal end. That is, there is no embodiment of any aspect of the invention described herein in which the most distal 4,6-dideoxy-4-acylamido-α-pyranose unit is linked (i.e., joined) to a cap structure which is then further linked (i.e., joined) to a single unit of 4,6-dideoxy-4-acylamido-α-pyranose via its $C_1$ or to the reducing end of a chain of multiple units of 4,6-dideoxy-4-acylamido-α-pyranose.

In the molecule according to the invention, the cap structure may consist of Formula 2:

Formula 2

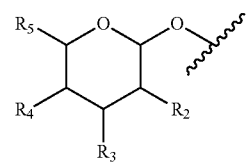

wherein $R_2$ is selected from —OH, an alkoxy consisting of 1, 2, 3, 4 or 5 carbon atoms, or an alkyl consisting of 1, 2, 3, 4 or 5 carbon atoms;

$R_3$ and $R_4$ are independently selected from an acylamido (which may be formamido, acetamido, propionamido or butyramido or a deacetylated variant thereof), —OH, a C1 to C5 alkoxy, a C1 to C5 alkyl or a totally or partially hydroxylated C1 to C5 alkyl; and $R_5$ is a C1 to C5 alkyl or a totally or partially hydroxylated C1 to C5 alkyl. As mentioned above, the cap is not a 4,6-dideoxy-4-acylamido-α-D-pyranose (4,6-dideoxy-4-formamido-α-D-mannopyranose or 4,6-dideoxy-4-formamido-α-D-glucopyranose), so the embodiment of Formula 2 in which $R_2$ and $R_3$ are both —OH and $R_4$ is formamido and $R_5$ is methyl is excluded.

The term "totally or partially hydroxylated" in reference to a hydroxylated alkyl indicates that one, or more than one, hydroxy group may be present within the hydroxylated alkyl. For example, more than one hydroxy group may be present if the hydroxylated alkyl comprises more than one carbon atom. Throughout this specification, the term "C1 to C5" indicates that there may be 1, 2, 3, 4 or 5 carbon atoms.

In an embodiment, $R_2$, $R_3$ and $R_4$ are all —OH and $R_5$ is hydroxymethyl. This embodiment of the cap structure may be referred to as a "mannose cap".

Alternatively, $R_2$ and/or $R_3$ may be alkoxy, $R_4$ may be acylamido or a deacetylated variant thereof and $R_5$ may be alkyl. In a particular embodiment of this arrangement, $R_2$ and/or $R_3$ is methoxy, $R_4$ is formamido or a deacetylated variant thereof and $R_5$ is methyl.

$R_4$ may alternatively comprise a modified alkoxy group which comprises an alkyl group conjugated to a linker molecule such as squarate or disuccinimidyl glutarate. The linker molecule may be further linked to a protein such as bovine serum albumin (BSA) or tetanus toxoid. Where $R_4$ is such an embodiment, $R_2$, $R_3$ and/or $R_5$ may be any as described above.

Formula 2 may have the arrangement shown below as Formula 2a:

Formula 2a

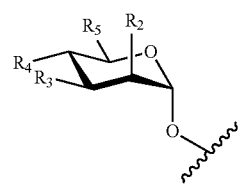

With $R_2$, $R_3$, $R_4$ and $R_5$ as defined above. As mentioned above, the embodiment wherein the cap structure consists of Formula 2a and $R_2$ and $R_3$ are both OH and $R_4$ is formamido and $R_5$ is methyl is excluded (i.e., Formula 2 is not 4,6-dideoxy-4-formamido-α-D-mannopyranose or 4,6-dideoxy-4-formamido-α-D-glucopyranose). The embodiments wherein the cap structure consists of Formula 2a and $R_2$ and $R_3$ are both OH and $R_4$ is acetylamido, propionamido or butyramido and $R_5$ is methyl are also excluded.

In an alternative molecule according to the invention, the cap structure may be an oxidised 4,6-dideoxy-4-acylamido-α-pyranose in which the pyranose ring is disrupted. For example, the cap structure may consist of Formula 3:

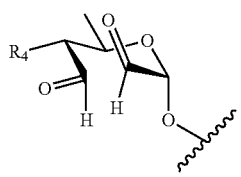

Formula 3 wherein $R_4$ is acylamido (which may be formamido, acetamido, propionamido or butyramido or a deacetylated variant thereof, preferably formamido or a deacetylated variant thereof), —OH, a C1 to C5 alkoxy, a C1 to C5 alkyl, or a totally or partially hydroxylated C1 to C5 alkyl.

The cap structure may comprise Formula 4:

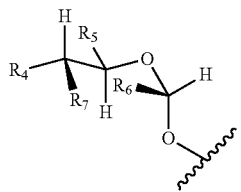

Formula 4 wherein $R_4$ is acylamido (which may be formamido, acetamido, propionamido or butyramido or a deacetylated variant thereof, preferably formamido or a deacetylated variant thereof), —OH, a C1 to C5 alkoxy, a C1 to C5 alkyl or a totally or partially hydroxylated C1 to C5 alkyl; $R_5$ is a C1 to C5 alkyl or a totally or partially hydroxylated C1 to C5 alkyl; and $R_6$ and $R_7$ are independently selected from —H, —$CH_3$, —CHO, —CH=NH, —CH=$NR_8$, CH=N—$NH_2$, —CH=N—$NHR_8$, —$CH_2NH_2$, —$CH_2NHNH_2$, or —$CH_2(NH)_nR_8$ where n=1 or 2.

$R_6$ and $R_7$ may be identical or may each be a different group from within this selection. $R_8$ is a non-pyranose containing group, i.e., a group which does not contain any pyranose-containing molecules. When $R_6$ and $R_7$ are both —CH=$NR_8$, or are both —CH=N—$NHR_8$, or are both —$CH_2(NH)_nR_8$, $R_8$ need not be identical in both $R_6$ and $R_7$.

For example, $R_8$ may be or may comprise a non-pyranose molecule linking (i.e., joining) an N atom present in $R_6$ or $R_7$ to a carrier such as a vaccine carrier protein (such as tetanus toxoid or detoxified diphtheria toxin), or a protein such a bovine serum albumin (BSA). The non-pyranose molecule may be derived from a molecule used as a linker, such as di(N-succinimidyl) glutarate (DSG), 3,4-dibutoxy-3-cyclobutene-1,2-dione (also known as dibutyl squarate) or adipic acid dihydrazide (ADH). Alternatively, in $R_6$ or $R_7$ the N atom which is located closest to the remainder of Formula 4 may be derived from the attached molecule (such as a carrier as outlined below), for example through a process of reductive amination.

The carrier may be a fluorescent molecule, an inert amphiphilic polymer, or a solid material entity such as a surface or a bead, or an entity such as a cell (which may be a live, attenuated or dead cell) or a cell membrane or portion thereof. The carrier may be a vaccine carrier entity as described below. The carrier may be a Brucella protein, i.e., a protein which is naturally occurring in a Brucella organism which is derived from natural or recombinant sources. The Brucella protein may be located at/attached to the surface of a cell.

The molecule according to the invention may comprise at least 7 contiguous units of 4,6-dideoxy-4-acylamido-α-pyranose, for example, at least 8, 9, 10, 11, 12, 13, 14, 15, 16, 17, 18, 19, 20, 21, 22, 23, 24, 25, 26, 27, 28, 29 or at least about 30 contiguous units. The molecule may be synthetic, or may be a modified OPS obtained from (for example, isolated or purified from) a naturally occurring or recombinant organism (typically a bacterium) comprising the genes required to synthesise an OPS, for example obtained from an Escherichia coli bacterium or a Brucella bacterium or a Y. enterocolitica bacterium such as Y. enterocolitica O:9, or may be a molecule prepared by modification (to include a cap structure as described herein) of an OPS obtained from such a bacterium. An exclusively $C_1$-$C_2$ linked OPS may be preferred. Therefore, the molecule may comprise at least about 40, 50, 60, 70, 80, 90 or at least about 100 contiguous units of 4,6-dideoxy-4-acylamido-α-pyranose. The molecule may be linked (i.e. joined) to one or more non-perosamine sugars, such as those found in naturally occurring OPS at the reducing end of the molecule and residual core sugars as outlined below. An example of such a sugar is Kdo (3-Deoxy-D-manno-oct-2-ulosonic acid). The molecule according to the first aspect of the invention may form part of a Rose Bengal Test antigen as described below, modified to include a molecule comprising a cap structure, as described above and elsewhere herein. Likewise, the molecule may form part of a Serum Agglutination Test (SAT) antigen, or part of a Complement Fixation Test (CFT) antigen, which may take the form of a cell or a subcellular fraction. The molecule may also constitute an O-polysaccharide element of a smooth lipopolysaccharide macromolecule. The molecule may be formed by chemical reactions performed directly upon any of these antigen components (i.e. without prior purification of the OPS).

A molecule comprising a cap structure of Formula 3 or 4 may be an intermediate within a reaction or method to provide a capped molecule. For example, Formula 3 may be an intermediate within a reaction to provide a molecule comprising a cap structure of Formula 4, as exemplified herein.

Any of the molecules according to the invention described above may be linked (i.e., joined) to a carrier, for example where $R_8$ is a carrier molecule as outlined above. Alternatively or additionally, the 4,6-dideoxy-4-acylamido-α-pyranose at the reducing end may be linked from $C_1$ to the carrier by a linking molecule which may optionally include a —$(CH_2)_n$—C=O group, wherein n=3-9. The linking group may, alternatively or additionally, include a squarate group and/or a group resulting from a linking method utilising disuccinimidyl glutarate (DSG) and/or adipic acid dihydrazide (ADH). Other linking arrangements are well known in the art and are discussed, for example, in WO2014/170681 as referred to elsewhere herein.

The link between the reducing end $C_1$ and the carrier may also include one or more non-perosamine sugars, such as those found in naturally occurring OPS at the reducing end of the molecule and residual core sugars that are retained as an artifact of the mild acid hydrolysis method to release OPS from lipid A and the rest of the core. An example of a sugar found at the reducing end of OPS prepared by this approach is Kdo (3-Deoxy-D-manno-oct-2-ulosonic acid). The Kdo may be linked to a carrier via its anomeric (reducing) carbon (which in Kdo is $C_2$), or via the carboxylic acid using methods well known in the art (such as conjugation of carboxylic acids to amines using carbodiimide crosslinkers). Any of the molecules according to the invention may be linked (i.e., joined) to a protein carrier, for example from the reducing end using an oligosaccharyltransferase enzyme (either before or after the inclusion of the cap in the molecule; for example, the enzyme may be expressed in a recombinant organism referred to above).

The carrier may be a protein such as tetanus toxoid or detoxified diphtheria toxin, or a protein such a bovine serum albumin (BSA). The carrier may be a fluorescent molecule, an inert amphiphilic polymer, or a solid material entity such as a surface or a bead. The carrier may be a *Brucella* protein, i.e., a protein which is naturally occurring in a *Brucella* organism and is produced either naturally or by recombinant means. Suitable proteins include, for example: lumazine synthase, L7/L12 ribosomal protein, GroEL (heat shock protein), GroES (heat shock protein), MBP (maltose binding protein), Cu—Zn SOD (copper-zinc superoxide dismutase) Omp31 (outer membrane protein 31), p39 (periplasmic binding protein), bp26 (also known as Omp28), U-Omp16 (unlipidated Omp16), U-Omp19 (unlipidated Omp19). The carrier may be a vaccine carrier entity as described below.

The molecule according to the first aspect of the invention may form part of a diagnostic conjugate. The term "diagnostic conjugate", as used throughout this specification, indicates that an oligosaccharide molecule (such as the molecule according to the first aspect of the invention, or a DIVA antigen oligosaccharide as defined below), is joined or linked (directly or via a further element) to a non-perosamine sugar as described above, and/or to a carrier molecule as described above, and/or to a cell or a portion of a cell, and/or to a non-saccharide carrier as described below. The diagnostic conjugate may be a sLPS or OPS molecule modified to include a cap structure, and/or may form part of a cell or subcellular fraction, such as a RBT antigen, a SAT antigen or a CFT antigen as described above.

A second aspect of the invention provides a vaccine composition comprising a molecule according to the first aspect of the invention and a vaccine carrier entity. The molecule may be conjugated to the vaccine carrier entity. The vaccine carrier entity may comprise, for example, a protein or peptide which may be any known in the art to be useful as a conjugate to an antigenic molecule to form a vaccine. By way of non-limiting example, the vaccine carrier entity may comprise tetanus toxoid (Verez-Bencomo et al (2004) Science 305:522-525), detoxified diphtheria toxins such as CRM 197 (Mawas et al (2002) Infection and Immunity 70:5107-5114), or other highly immunogenic proteins (Svenson & Lindberg (1981) Infection and Immunity 32:7). The vaccine carrier entity may also comprise an immunogenic particle such as a liposome, micelle, microsphere, nanoparticle or inactive viral particle wherein the oligosaccharide is incorporated at the surface of the particle. The vaccine carrier entity may comprise a *Brucella* protein, i.e., a protein which is naturally occurring in a *Brucella* organism or occurring (i.e., expressed) in a recombinant organism such as an *Escherichia coli* or a *Brucella* organism, or a peptide derived from such a protein (for example, a fragment of such a protein). Suitable proteins include, by way of non-limiting example: lumazine synthase, L7/L12 ribosomal protein, GroEL (heat shock protein), GroES (heat shock protein), MBP (maltose binding protein), Cu—Zn SOD (copper-zinc superoxide dismutase) Omp31 (outer membrane protein 31), p39 (periplasmic binding protein), bp26 (also known as Omp28), U-Omp16 (unlipidated Omp16), U-Omp19 (unlipidated Omp19).

The vaccine composition may comprise a molecule according to the first aspect of the invention which is a sLPS molecule comprising a modified OPS molecule which comprises a cap structure linked to the terminal 4,6-dideoxy-4-formamido-α-D-mannopyranose.

In an embodiment, in the vaccine composition, the molecule comprises only $C_1$-$C_2$ links between each pair of 4,6-dideoxy-4-acylamido-α-pyranose units, i.e., there is a $C_1$-$C_2$ link between every pair of units in the molecule. In an alternative embodiment, in the vaccine composition, the molecule comprises at least one $C_1$-$C_3$ link between a pair of 4,6-dideoxy-4-acylamido-α-pyranose units.

In the vaccine composition according to the second aspect of the invention, the molecule may comprise at least about 7, 8, 9, 10, 11, 12, 13, 14 or 15 contiguous units of 4,6-dideoxy-4-acylamido-α-pyranose. For example, the molecule may comprise at least about 16 units of 4,6-dideoxy-4-acylamido-α-pyranose, for example, at least about 17, 18, 19, 20, 21, 22, 23, 24, 25, 26, 27, 28, 29 or at least about 30 contiguous units. The molecule may be synthetic, or may be a modified OPS obtained from (for example, isolated or purified from) a naturally occurring or recombinant organism (typically a bacterium) comprising the genes required to synthesise an OPS, for example an OPS obtained from an *E. coli* bacterium, a *Brucella* bacterium or from a *Y. enterocolitica* bacterium such as *Y. enterocolitica* O:9, or may be a molecule prepared by modification (to include a cap structure as described herein) of an OPS obtained from such a bacterium. Therefore, the molecule may comprise at least about 40, 50, 60, 70, 80, 90 or at least about 100 contiguous units of 4,6-dideoxy-4-acylamido-α-pyranose.

According to a third aspect of the invention, there is provided a cell (or subcellular fraction obtained from a cell) comprising a molecule according to the first aspect of the invention. The cell may be a bacterial cell such as a *Brucella* cell or a *Y. enterocolitica* O:9 cell or an *E. coli* cell. The cell may be a dead or attenuated cell which may additionally be stained; for example, the cell comprising the molecule according to the first aspect of the invention may be a Rose Bengal Test antigen in which at least one OPS on the surface of the RBT cell has been modified to form a molecule according to the first aspect of the invention, for example by use of an oxidation method as described herein.

The molecule may be introduced into the cell from the cell exterior by any known transformation method. Alternatively, the cell may be engineered to express an OPS comprising a cap structure as described, for example, a cap structure of Formula 2 in which $R_2$ and/or $R_3$ is methoxy, $R_4$ is formamido and $R_5$ is methyl. For example, the cell is a *Brucella* cell or a *Y. enterocolitica* O:9 cell which may be engineered to express the rfbT gene from the organism *Vibrio cholera* O:1 Ogawa.

A fourth aspect of the invention provides a vaccine composition comprising a cell according to the third aspect of the invention which is a *Brucella* cell or a *Y. enterocolitica* O:9 cell.

The vaccine composition according to the second or fourth aspects of the invention may further comprise excipients and/or diluents appropriate for the means by which the composition is to be administered to a subject in need of vaccination against infection by *Brucella*. Selection of appropriate components is within the routine capability of the skilled person without the application of inventive activity.

For example, the vaccine composition of the invention may conveniently be formulated using a pharmaceutically acceptable excipient or diluent, such as, for example, an aqueous solvent, non-aqueous solvent, non-toxic excipient, such as a salt, preservative, buffer and the like. Examples of non-aqueous solvents are propylene glycol, polyethylene glycol, vegetable oil and injectable organic esters such as ethyloleate. Aqueous solvents include water, alcoholic/aqueous solutions, saline solutions, parenteral vehicles such as sodium chloride, Ringer's dextrose, etc. Preservatives include antimicrobials, anti-oxidants, chelating agents and inert gases. The pH and exact concentration of the various components the vaccine composition are adjusted according to routine skills.

In certain situations, it may also be desirable to formulate the vaccine composition to comprise an adjuvant to enhance the immune response. Such adjuvants include all acceptable immunostimulatory compounds such as, for example, a cytokine, toxin, or synthetic composition. Commonly used adjuvants include aluminium hydroxide, aluminium phosphate, calcium phosphate, Freund's adjuvants and Quil-A saponin. In addition to adjuvants, it may be desirable to co-administer biologic response modifiers (BRM) with the vaccine conjugate to down regulate suppressor T cell activity.

Possible vehicles for administration of the vaccine composition include but are not limited to liposomes, micelles and/or nanoparticles. Liposomes are microscopic vesicles that consist of one or more lipid bilayers surrounding aqueous compartments. Liposomes are similar in composition to cellular membranes and, as a result, liposomes generally can be administered safely and are biodegradable. Techniques for preparation of liposomes and the formulation (e.g., encapsulation) of various molecules with liposomes are well known.

Depending on the method of preparation, liposomes may be unilamellar or multilamellar and can vary in size with diameters ranging from about 0.02 μm to greater than about 10 μm. Liposomes can also adsorb to virtually any type of cell and then release the encapsulated agent. Alternatively, the liposome fuses with the target cell, whereby the contents of the liposome empty into the target cell. Alternatively, an absorbed liposome may be endocytosed by cells that are phagocytic. Endocytosis is followed by intralysosomal degradation of liposomal lipids and release of the encapsulated agents. In the present context, the vaccine composition according to the invention can comprise a molecule according to the first aspect of the invention localized on the surface of the liposome, to facilitate antigen presentation without disruption of the liposome or endocytosis. Irrespective of the mechanism or delivery, however, the result is the intracellular disposition of the associated vaccine composition and/or molecule.

Liposomal vectors may be anionic or cationic. Anionic liposomal vectors include pH sensitive liposomes which disrupt or fuse with the endosomal membrane following endocytosis and endo some acidification.

Other suitable liposomes that may be used in the compositions and methods of the invention include multilamellar vesicles (MLV), oligolamellar vesicles (OLV), unilamellar vesicles (UV), small unilamellar vesicles (SUV), medium-sized unilamellar vesicles (MIN), large unilamellar vesicles (LUV), giant unilamellar vesicles (GUV), multivesicular vesicles (MVV), single or oligolamellar vesicles made by reverse-phase evaporation method (REV), multilamellar vesicles made by the reverse-phase evaporation method (MLV-REV), stable plurilamellar vesicles (SPLV), frozen and thawed MLV (FATMLV), vesicles prepared by extrusion methods (VET), vesicles prepared by French press (FPV), vesicles prepared by fusion (FUV), dehydration-rehydration vesicles (DRV), and bubblesomes (BSV). Techniques for preparing these liposomes are well known in the art.

Other forms of delivery particle, for example, microspheres and the like, also are contemplated for delivery of the vaccine.

In one embodiment, the vaccine composition may be included in an animal feed (i.e., a foodstuff suitable for consumption by an animal) comprising a vaccine composition according to the invention. This may, in non-limiting examples, be in the form of pellets, crumbs or a mash which may further comprise, again for example only, grain, grass and/or protein components. The composition may also be included in drinking liquids and/or administered via a spray into the atmosphere surrounding the animal which is, consequently, inhaled by the animal.

The molecule according to the first aspect of the invention, or the vaccine composition according to the second and fourth aspects of the invention, or the cell according to the third aspect of the invention, may be for use as a vaccine in a method for vaccinating an animal against infection by a *Brucella* organism. The method may comprise a method according to the fifth aspect of the invention.

Therefore, a fifth aspect of the invention provides a method for vaccinating an animal against infection by a *Brucella* organism, and/or of reducing the risk of infection by a *Brucella* organism, comprising administering to the animal a protective amount of a molecule according to the first aspect of the invention, or a vaccine composition according to the second or fourth aspects of the invention, or a cell according to the third aspect of the invention. The vaccination is against infection by a smooth strain *Brucella* organism, for example *B. abortus, B. melitensis* and/or *B. suis*. The method includes inducing an immune response in the animal by administering the molecule or vaccine composition or cell to the animal. The method may further comprise obtaining a biological sample from the animal and contacting it with a DIVA antigen and detecting no or little antibody binding to the DIVA antigen. A DIVA antigen as referred to herein is defined below. It includes an antigen disclosed in WO2014/170681 as being specific for anti-OPS antibodies which were induced due to infection with a smooth strain *Brucella* organism having an OPS comprising a polymer of 4,6-dideoxy-4-formamido-a-D-mannopyranose units and comprising a $C_1$-$C_2$ or a $C_1$-$C_3$ glycosidic link between each pair of adjacent units. Such antigens were referred to in that disclosure as "specific M-antigens".

The DIVA antigen may comprise a DIVA antigen oligosaccharide consisting of two, three, four or five contiguous units of 4,6-dideoxy-4-acylamido-α-D-mannopyranose. For example, it may comprise a disaccharide consisting of two units of 4,6-dideoxy-4-acylamido-α-D-mannopyranose joined by a $C_1$-$C_3$ link, and/or may comprise a tetrasaccharide consisting of four units of 4,6-dideoxy-4-acylamido-α-D-mannopyranose and comprising a central $C_1$-$C_3$ link and two $C_1$-$C_2$ links, the disaccharide or tetrasaccharide joined (i.e., linked) to a non-saccharide carrier via the reducing end. In the tetrasaccharide, a "central $C_1$-$C_3$ link" indicates that the $C_1$-$C_3$ link appears between the second and third 4,6-dideoxy-4-acylamido-α-mannopyranose units in the tetrasaccharide.

Alternatively, the DIVA antigen may comprise a DIVA antigen oligosaccharide which is a trisaccharide consisting of three units of 4,6-dideoxy-4-acylamido-α-D-mannopyranose and comprising one $C_1$-$C_3$ link and one $C_1$-$C_2$ link, or comprising two $C_1$-$C_2$ links, the trisaccharide joined to a non-saccharide carrier via the reducing end. In a further alternative, the DIVA antigen may comprise a DIVA antigen oligosaccharide which is a disaccharide consisting of two units of 4,6-dideoxy-4-acylamido-α-D-mannopyranose and a $C_1$-$C_2$ link, the disaccharide joined (i.e., linked) to a non-saccharide carrier via the reducing end.

Alternatively, the DIVA antigen may comprise a DIVA antigen oligosaccharide which is a pentasaccharide consisting of five units of 4,6-dideoxy-4-acylamido-α-D-mannopyranose and comprising one $C_1$-$C_3$ link and three $C_1$-$C_2$ links, the $C_1$-$C_3$ link being positioned between the second and third 4,6-dideoxy-4-acylamido-α-D-mannopyranose units from the non-reducing end, the pentasaccharide being joined (i.e., linked) to a non-saccharide carrier via the reducing end.

In a further alternative, the DIVA antigen may comprise a monosaccharide consisting of one unit of 4,6-dideoxy-4-acylamido-α-D-mannopyranose joined to a non-saccharide carrier via the $C_1$ carbon.

The term "non-saccharide carrier", as used throughout this specification, may refer to a carrier which contains no saccharide groups, for example, a protein such as tetanus toxoid or detoxified diphtheria toxin, or a protein such a bovine serum albumin (BSA).

The non-saccharide carrier may be a fluorescent molecule, an inert amphiphilic polymer, a lipid or glycolipid, or a solid material entity such as a surface or a bead. The use of such carriers allows for various assay formats that detect the presence of antibody in a sample, for example, ELISA, FPA, TR-FRET, lateral flow assay or bead-based agglutination assay, as outlined below.

A "solid" bead encompasses non-liquid structures such as gel beads or latex beads. Therefore, the DIVA antigen may be or form part of a diagnostic conjugate which may be in the form of a surface having at least one DIVA antigen oligosaccharide as described herein attached thereto via a linking system which includes a covalent attachment to the oligosaccharide. Attachment may be, for example, via passive absorption mediated by a protein carrier, or a non-protein carrier molecule comprising hydrophobic elements, covalently attached to the oligosaccharide, via the reducing end as mentioned above. The passive absorption being due to, for example, hydrophobic and ionic interactions with a surface such as polystyrene, polyvinyl chloride, latex, glass, nitrocellulose, polyvinylidene difluoride. The protein carrier may be, for example, BSA. Other functional groups available on the solid entity surface may also be utilised, such as maleimide (binds to sulfhydryls), amine (numerous binding options available through use of a linker), aldehydes (bind to amines), or carboxyl (bind to amines).

The DIVA antigen described herein may be a synthetic conjugate, for example, as described in WO2014/170681. For example, the DIVA antigen may have or comprise Structure III or Structure VI, as set out below, or Structure IV or Structure V or Structure VII or Structure XI or Structure XII (see Table 2 below).

The method may comprise use of more than one DIVA antigen, by simultaneously or sequentially contacting the biological sample (obtained from the animal in which an immune response has been induced by administering the molecule or vaccine composition or cell to the animal) with two or more DIVA antigens. For example, a tetrasaccharide-containing DIVA antigen as described above may be used in combination with a trisaccharide-containing DIVA antigen comprising a trisaccharide consisting of three units of 4,6-dideoxy-4-acylamido-α-D-mannopyranose and comprising two $C_1$-$C_2$ links, the trisaccharide joined (i.e., linked) to a non-saccharide carrier via the reducing end. Alternatively, a tetrasaccharide-containing DIVA antigen as described above may be used in combination with a disaccharide-containing DIVA antigen comprising a disaccharide consisting of two units of 4,6-dideoxy-4-acylamido-α-D-mannopyranose and a $C_1$-$C_2$ link, the disaccharide joined (i.e., linked) to a non-saccharide carrier via the reducing end. For example, a DIVA antigen of Structure VI may be used in combination with a DIVA antigen of Structure XII and/or a DIVA antigen of Structure XI.

In the method according to any aspect of the invention, the animal may be a ruminant, camelid or suid animal such as a bovine or swine animal, for example, a cow, pig, sheep or goat, or may be a human being. The biological sample in any aspect of the invention may be a blood, plasma, serum, tissue, saliva or milk sample. Therefore, the biological sample is not a laboratory sample comprising only antibodies and/or oligo- or polysaccharides (plus laboratory reagents), such as a monoclonal antibody preparation, but is a complex sample also comprising many other components including other antibodies, unrelated to the method to be conducted.

Advantageously, the presence of antibodies which are detectable by the DIVA antigen(s) described herein and in WO2014/170681 in a sample from an animal, indicates that the animal is, or has previously been, infected with a smooth strain *Brucella* bacterium so as to elicit an immune response and raising of antibodies. The *Brucella* may be any smooth strain (those that present OPS containing 4,6-dideoxy-4-formamido-mannopyranosyl on their surface). A lack of binding to the DIVA antigen in the method according to the invention is a means of confirming that the animal has not been infected with these organisms.

Importantly, when the animal has been vaccinated with a vaccine according to the invention, no response to the DIVA antigen is observed (i.e., no or little antibody binding to the DIVA antigen is detected), because the epitope identified by the inventors, which is dependent on the presence of a terminal 4,6-dideoxy-4-acylamido-α-D-mannopyranose, is not present in the vaccine molecule. Therefore, a positive response in such an assay can be taken as confirmation of infection. This is a very important advantage over existing methods as it provides a DIVA test, capable of distinguishing vaccinated from infected animals.

The methods according to any aspect of the invention may comprise use of an ELISA assay, for example an indirect ELISA or a competitive ELISA, the design of which is within the routine ability of the skilled person. For example, in an indirect ELISA, the DIVA antigen or DIVA antigen oligosaccharide described herein (or a diagnostic conjugate comprising a DIVA antigen oligosaccharide) is immobilised on an ELISA plate, for example to a non-functionalised ELISA plate via the use of a conjugated carrier molecule such as BSA, capable of passive absorption to the plate. The biological sample to be tested is then added to the plate and incubated for a period of time, after which the plate is washed. A detection conjugate (such as HRP-conjugated Protein-G or HRP-conjugated anti-species IgG) is added and the plate incubated, washed and subsequently developed by a method appropriate to the detection conjugate being used (in the case of HRP, ABTS may be suitable, as described below). This allows determination of the level of binding, if any, of antibodies present in the biological sample to the antigen present on the plate.

Other ELISA variants, such as a blocking ELISA (Rhodes et al (1989) Journal of Veterinary Diagnostic Investigation 1:324-328), are well known to the skilled person and may be utilised without application of inventive skill.

The methods according to the invention may comprise use of TR-FRET methods, such as are described, for example, in WO2009/118570 and WO2011/030168. In this context, the DIVA antigen or DIVA antigen oligosaccharide may be conjugated, directly or indirectly, to a TR-FRET label such as a lanthanide chelate (donor fluorophore) or fluorescein (acceptor fluorophore) as described in those patent publications.

As mentioned above, the DIVA antigen or DIVA antigen oligosaccharide (or diagnostic conjugate comprising a DIVA antigen oligosaccharide) may be formed by conjugation, directly or indirectly, of the di- or tri- or tetra- or pentasaccharide to fluorophores that will enable the detection of antigen-antibody binding by fluorescence polarisation (Nasir & Jolley (1999) Comb Chem High Throughput Screen 2:177-190) as described, for example, in U.S. Pat. No. 5,976,820. This forms the basis of a fluorescence polarisation assay (FPA) as referred to elsewhere herein.

By way of non-limiting example, other assay formats which may be utilised in the invention include a lateral flow assay, in which antigen or oligosaccharide is absorbed to a membrane along which a serum (comprising serum antibodies) may be caused to flow. The serum may be mixed with anti-species antibodies, labelled with colloidal gold or latex beads (Abdoel et al (2008) Vet Microbiol 130:312-319). A further alternative is a bead based agglutination assay, for example in which an antigen-BSA conjugate or an oligosaccharide-BSA conjugate is passively coated to a latex bead. The bead is then added to a serum sample and the occurrence or absence of agglutination observed (indicating antibody binding to antigen on the bead) (Abdoel & Smits (2007) Microbiology and Infectious Disease 57:123-128).

The method may further comprise contacting the sample with a universal antigen; throughout this specification, a "universal antigen" is an antigen comprising at least 6 contiguous units of 4,6-dideoxy-4-acylamido-α-pyranose comprising $C_1$-$C_2$ links between most or all pairs of units and optionally comprising at least one $C_1$-$C_3$ link between a pair of units. The method may comprise detection of antibody binding to the universal antigen. This provides an indication that the vaccine has elicited an immune response in the animal. The universal antigen may comprise an OPS (or portion of an OPS) obtained from a *Brucella* organism or from *Y. enterocolitica* O:9; for example, the OPS or portion thereof may form part of a sLPS, or a whole cell. Alternatively, the universal antigen may have the structure VIII, IX or XIX as set out below.

A sixth aspect of the invention provides a method for screening a population of animals known to comprise individuals which have been vaccinated with a molecule according to the first aspect of the invention or with a vaccine composition according to the second or fourth aspects of the invention or with a cell according to the third aspect of the invention, the method comprising contacting a biological sample obtained from an animal in the population with a DIVA antigen, wherein detection of antibody binding to the DIVA antigen indicates that the sample was obtained from an animal infected with a *Brucella* organism. The method for screening may, therefore, be a method for detecting one or more animals infected with a *Brucella* organism in a population of animals known to comprise individuals which have been vaccinated as described (i.e., animals to which a molecule according to the first aspect of the invention or a vaccine composition according to the second or fourth aspects of the invention or a cell according to the third aspect of the invention has been administered), since there is no detection of antibody binding to the DIVA antigen in a sample obtained from a vaccinated animal. The method may comprise a step of obtaining the biological sample from each animal in the population. The biological sample and the DIVA antigen may be any as described above in relation to the fifth aspect of the invention.

A seventh aspect of the invention provides a kit comprising a vaccine composition according to the second or fourth aspects of the invention. For example, the vaccine composition may be provided packaged in lyophilised form and the kit may further comprise a solution suitable for use to reconstitute the vaccine composition to a form suitable for administration to an animal.

Alternatively or additionally, the kit may further comprise an administration device comprising, for example, a needle, a syringe and/or a pipette, suitable for administering the vaccine composition (which may have been reconstituted from lyophilised form) to an animal.

An eighth aspect of the invention provides a method for obtaining a cell according to the third aspect of the invention, comprising expressing the rfbT gene from the organism *Vibrio cholera* O:1 Ogawa in a *Brucella* cell or in a *Y. enterocolitica* O:9 cell. Expression of this gene in *Brucella* will cause the OPS to be synthesised with a methoxy cap on $C_2$.

A ninth aspect of the invention provides a method for detection of anti-*Brucella* antibodies in a sample, comprising contacting the sample with a diagnostic conjugate comprising the molecule according to the first aspect of the invention. The diagnostic conjugate may, for example, comprise a modified RBT antigen, SAT antigen, CFT antigen or sLPS antigen including the molecule according to the first aspect of the invention. In this method, the anti-*Brucella* antibodies are not antibodies to *B. inopinata* BO2.

The molecule may comprise at least about 7, 8, 9, 10, 11, 12, 13, 14 or 15 contiguous units of 4,6-dideoxy-4-acylamido-α-pyranose. For example, the molecule may comprise at least about 16 units of 4,6-dideoxy-4-acylamido-α-pyranose, for example, at least about 17, 18, 19, 20, 21, 22, 23, 24, 25, 26, 27, 28, 29 or at least about 30 contiguous units. Any 4,6-dideoxy-4-acylamido-α-pyranose may be 4,6-dideoxy-4-formamido-α-pyranose, for example, 4,6-dideoxy-4-formamido-α-D-mannopyranose. The molecule may be synthetic, or it may be chemically modified OPS derived from a natural or recombinant source. It may be a modified OPS obtained from (for example, isolated or purified from) a recombinant organism (typically a bacterium) comprising the genes required to synthesise a capped OPS, for example from an *E. coli* bacterium or a *Brucella* bacterium or from a *Y. enterocolitica* bacterium such as *Y. enterocolitica* O:9, modified to express the rfbT gene as outlined above. It may be a molecule prepared by modification (to include a cap structure as described herein) of an OPS obtained from an organism (typically a bacterium) comprising the genes required to synthesise an OPS. Therefore, the molecule may comprise at least about 40, 50, 60, 70, 80, 90 or at least about 100 contiguous units of 4,6-dideoxy-4-acylamido-α-pyranose.

The sample may be a biological sample, of any type as described above in relation to other aspects of the invention, obtained from an animal suspected to have been infected with a *Brucella* organism of species *B. abortus, B. melitensis* and *B. suis*. Alternatively or additionally, the sample may be a biological sample obtained from an animal known or suspected to have been vaccinated with a vaccine not according to the present invention, for example, a *B. abortus* S19 vaccine, a *B. melitensis* Rev1 vaccine or a vaccine that is any other smooth strain of *B. abortus, B. melitensis* or *B. suis*. Advantageously, when conducting a method according to the ninth aspect of the invention, the diagnostic conjugate does not bind to antibodies present in a sample of an animal which has been vaccinated in such a way, or has reduced binding to such antibodies compared to the binding exhibited to a *Brucella* sLPS antigen. Therefore, this provides an alternative DIVA test, allowing continued use of vaccines of the prior art and providing the ability to better distinguish between an infected and a vaccinated animal.

Therefore, the method according to the ninth aspect of the invention may provide a method for screening a population of animals known to comprise individuals which have been vaccinated with a *Brucella* "smooth cell"-based vaccine (i.e., such as a *B. abortus* S19 vaccine, a *B. melitensis* Rev1 vaccine or a vaccine that is any other smooth strain of *B. abortus, B. melitensis* or *B. suis*), the method comprising contacting a biological sample obtained from an animal in the population with a diagnostic conjugate comprising the molecule according to the first aspect of the invention, wherein detection of antibody binding to the diagnostic conjugate indicates that the sample was obtained from an animal infected with a *Brucella* organism. The method for screening may, therefore, be a method for detecting one or more animals infected with a *Brucella* organism in a population of animals known to comprise individuals which have been vaccinated as described in this paragraph. The method may comprise a step of obtaining the biological sample from each animal in the population.

The method may take the form of an ELISA assay, FPA, TR-FRET, lateral flow assay or bead-based agglutination assay, as described above in relation to previous aspects of the invention. Likewise, animals and samples as described above in relation to previous aspects of the invention may be used in the method according to the ninth aspect of the invention.

A tenth aspect of the invention provides a method of detecting the presence in a sample of an anti-*Brucella* antibody comprising contacting the sample with a diagnostic conjugate comprising a trisaccharide consisting of three units of 4,6-dideoxy-4-acylamido-α-pyranose and comprising only $C_1$-$C_2$ links and/or with a diagnostic conjugate comprising a disaccharide consisting of two units of 4,6-dideoxy-4-acylamido-α-pyranose joined by a $C_1$-$C_2$ link. The trisaccharide and/or disaccharide is linked (i.e., joined), directly or via another element, to a non-saccharide carrier via the reducing end. In an alternative, the diagnostic conjugate may comprise a monosaccharide consisting of one unit of 4,6-dideoxy-4-acylamido-α-pyranose joined to a non-saccharide carrier via the $C_1$ carbon. The tenth aspect may further comprise contacting the sample with a diagnostic conjugate comprising a tetrasaccharide consisting of four units of 4,6-dideoxy-4-acylamido-α-pyranose and comprising a central $C_1$-$C_3$ link and two $C_1$-$C_2$ links, the tetrasaccharide linked (i.e., joined), directly or via another element, to a non-saccharide carrier via the reducing end. Any 4,6-dideoxy-4-acylamido-α-pyranose may be 4,6-dideoxy-4-formamido-α-pyranose or 4,6-dideoxy-4-acylamido-α-D-mannopyranose, for example, 4,6-dideoxy-4-formamido-α-D-mannopyranose. The non-saccharide carrier may be any carrier as described above in relation to the first aspect of the invention. The diagnostic conjugate comprising a trisaccharide may have Structure XII; the diagnostic conjugate comprising a disaccharide may have Structure XI; the diagnostic conjugate comprising a monosaccharide may have Structure II. The diagnostic conjugate comprising a tetrasaccharide may have Structure VI. The method may take the form of an ELISA assay, FPA, TR-FRET, lateral flow assay or bead-based agglutination assay, as described above in relation to previous aspects of the invention. Likewise, animals and samples as described above in relation to previous aspects of the invention may be used in the method according to the ninth aspect of the invention.

The sample to be contacted with the diagnostic conjugate may be obtained at or after about 10 weeks after an animal from which the sample is obtained has been, or is suspected to have been, infected with or exposed to *Brucella* organism, for example, at or after about 11, 12, 13, 14, 15, 16, 17, 18, 19, 20, 21, 22, 23, 24, 25, 30, 35 40, 45, 50, 53, 55, or about 60 weeks after infection or exposure. It may be preferred to obtain the sample at or after about 16 weeks after an animal from which the sample is obtained has been, or is suspected to have been, infected with or exposed to *Brucella* organism. The sample may be obtained in the period 10-40 weeks, for example in the period 15-40 weeks after an animal from which the sample is obtained has been, or is suspect to have been, infected with or exposed to *Brucella* organism. A "week after exposure" indicates a period of a calendar week after exposure plus or minus 4 days. Therefore, for example, "10 weeks after exposure" would indicate exposure or infection of the animal occurring between about 66 days and about 74 days 10 calendar weeks plus or minus 4 days) prior to the obtaining of the sample; "16 weeks after exposure" would indicate exposure or infection of the animal occurring between about 108 days and about 116 days (16 calendar weeks plus or minus 4 days) prior to the obtaining of the sample.

Throughout the description and claims of this specification, the words "comprise" and "contain" and variations of the words, for example "comprising" and "comprises", mean (and are to be considered interchangeable with) "including but not limited to" and do not exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Other features of the present invention will become apparent from the following examples. Generally speaking, the invention extends to any novel one, or any novel combination, of the features disclosed in this specification (including the accompanying claims and figures). Thus, features, integers, characteristics, compounds or chemical moieties described in conjunction with a particular aspect, embodiment or example of the invention are to be understood to be applicable to any other aspect, embodiment or example described herein, unless incompatible therewith.

Moreover, unless stated otherwise, any feature disclosed herein may be replaced by an alternative feature serving the same or a similar purpose.

BRIEF DESCRIPTION OF THE FIGURES

Embodiments of the invention will now be described, by way of example only, with reference to FIGS. 1-16 in which:

Figure 4:
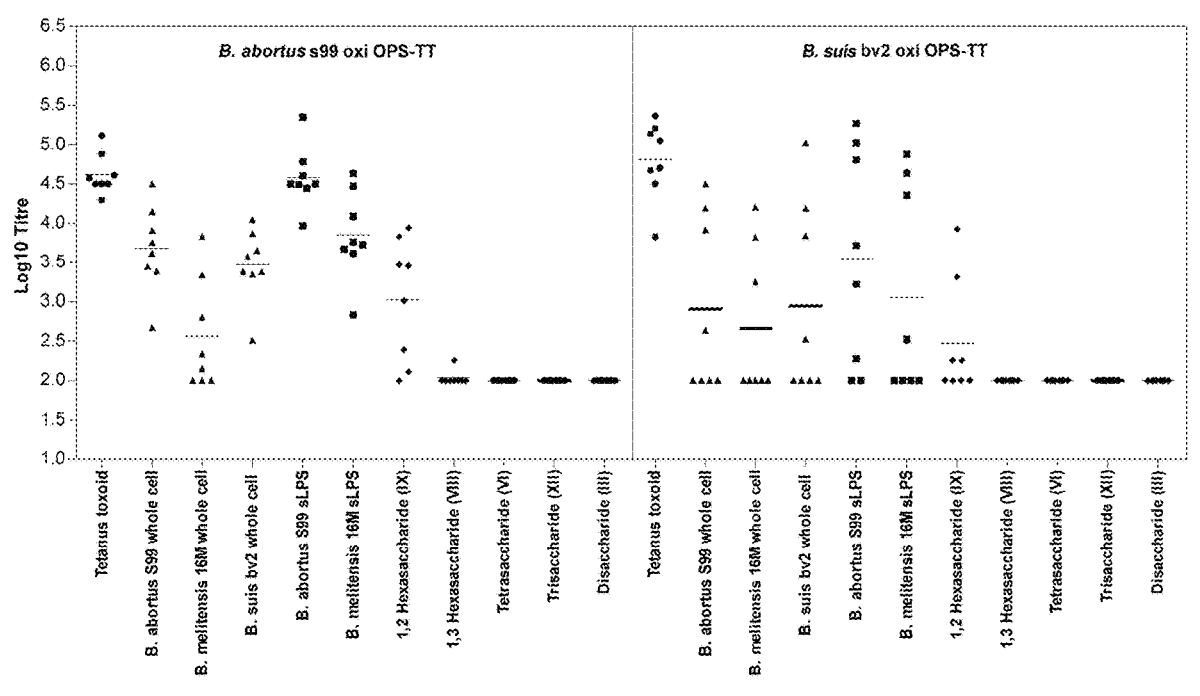

FIG. 4 shows antibody binding, shown as endpoint titer (y-axis) by iELISA, of sera (48 days post immunization) from two groups of 8 CD1 mice immunized with two types of TT-*Brucella* OPS conjugate evaluated against different antigens (Tetanus toxoid; *B. abortus* S99 whole cells [A dominant OPS]; *B. melitensis* 16M whole cells [M dominant OPS]; *B. suis* biovar 2 whole cells [exclusively α(1→2) linked OPS]; *B. abortus* S99 sLPS [A dominant OPS]; *B. melitensis* 16M sLPS [M dominant OPS]; 1,2 hexasaccharide=Structure IX; 1,3 hexasaccharide=Structure VIII; Tetrasaccharide=Structure VI; Trisaccharide=Structure XII; Disaccharide=Structure III); horizontal bars show the median titer, the range of titers tested were from $\log_{10}$ 2.0;

FIG. 8 shows the iELISA results for serum samples from 17 pigs infected with *B. suis* biovar 2 (A dominant, OPS is exclusively 1,2 linked), shown as 'Infected', and 12 randomly sampled non-infected pigs, shown as 'Rand Non-In'. ELISAs were performed using the exclusively 1,2 linked trisaccharide BSA conjugate (Structure XII) alone (at 2.5 µg/ml coating concentration) and using an even mix by mass (1.25 µg/ml coating concentration of each antigen, total concentration=2.5 µg/ml) of the exclusively 1,2 linked trisaccharide BSA conjugate (Structure XII) and the M tetrasaccharide BSA conjugate (Structure VI);

FIG. 9 shows iELISA results (y-axis), using *B. abortus* S99 sLPS antigen, for 20 sera from 4 cows experimentally infected with *B. abortus* 544 (solid lines) that were each sampled at 3, 7, 16, 24 and 53 weeks post-infection (x-axis) and for 20 sera from 4 cows experimentally infected with *Y. enterocolitica* O:9 that were also sampled at 3, 7, 16, 24 and 53 weeks post-infection;

FIG. 12 shows iELISA results (y-axis), monosaccharide (Structure II) antigen, for 20 sera from 4 cows experimentally infected with *B. abortus* 544 (solid lines) that were each sampled at 3, 7, 16, 24 and 53 weeks post-infection (x-axis) and for 20 sera from 4 cows experimentally infected with *Y. enterocolitica* O:9 that were also sampled at 3, 7, 16, 24 and 53 weeks post-infection;

FIG. 13 is a scatter plot showing the iELISA results using *B. abortus* S99 sLPS (x-axis) against iELISA results using the exclusively 1,2 linked trisaccharide BSA conjugate (Structure XII) antigen (y-axis), with data points showing the results for 29 serum samples from 29 *B. abortus* infected cattle ('Infected', solid diamonds), 31 serum samples from 31 non-*Brucella* infected cattle that were false positive for conventional serodiagnostic assays for brucellosis ('FPSRs', open circles) and 20 serum samples from 20 randomly selected non-infected cattle ('Rand Non-In', crosses);

Figure 14:
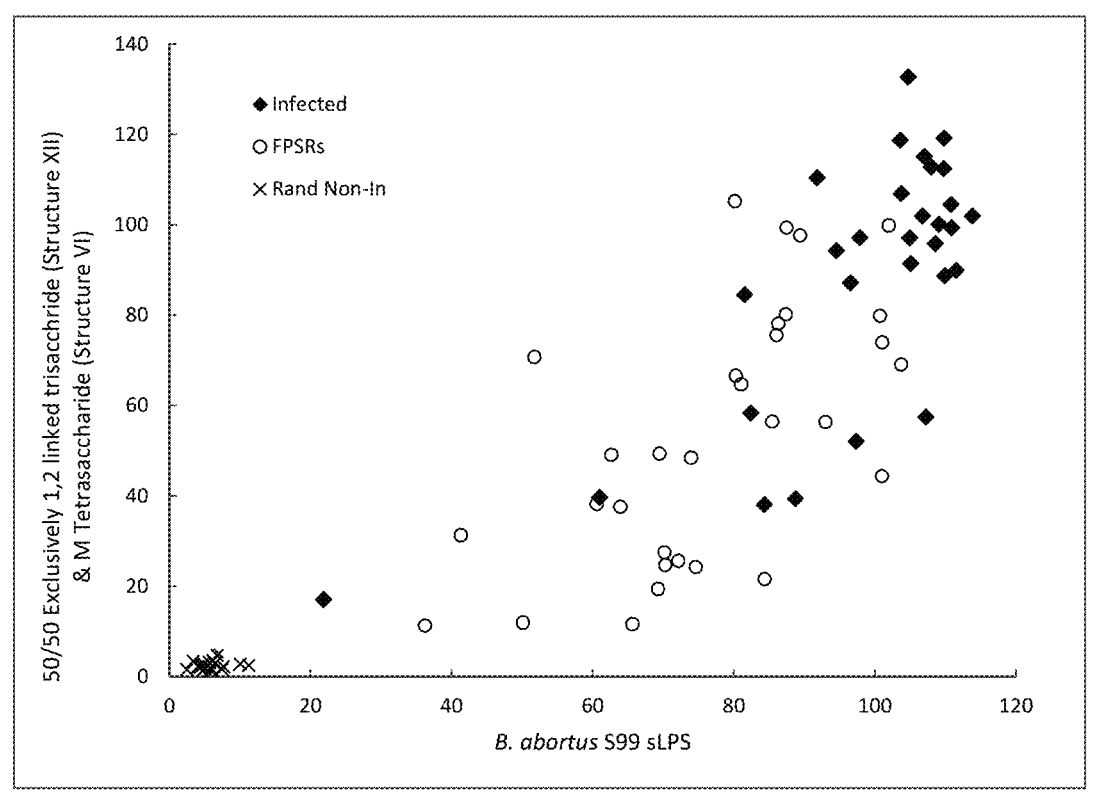

FIG. 14 is a scatter plot showing the iELISA results using *B. abortus* S99 sLPS (x-axis) against iELISA results using an even mix by mass (1.25 µg/ml coating concentration of each antigen, total concentration=2.5 µg/ml) of the exclusively 1,2 linked trisaccharide BSA conjugate (Structure XII) and the M tetrasaccharide BSA conjugate (Structure VI) (y-axis), with data points showing the results for 29 serum samples from 29 *B. abortus* infected cattle ('Infected', solid diamonds), 31 serum samples from 31 non-*Brucella* infected cattle that were false positive for conventional serodiagnostic assays for brucellosis ('FPSRs', open circles) and 20 serum samples from 20 randomly selected non-infected cattle ('Rand Non-In', crosses)

EXAMPLES

Figure 1:
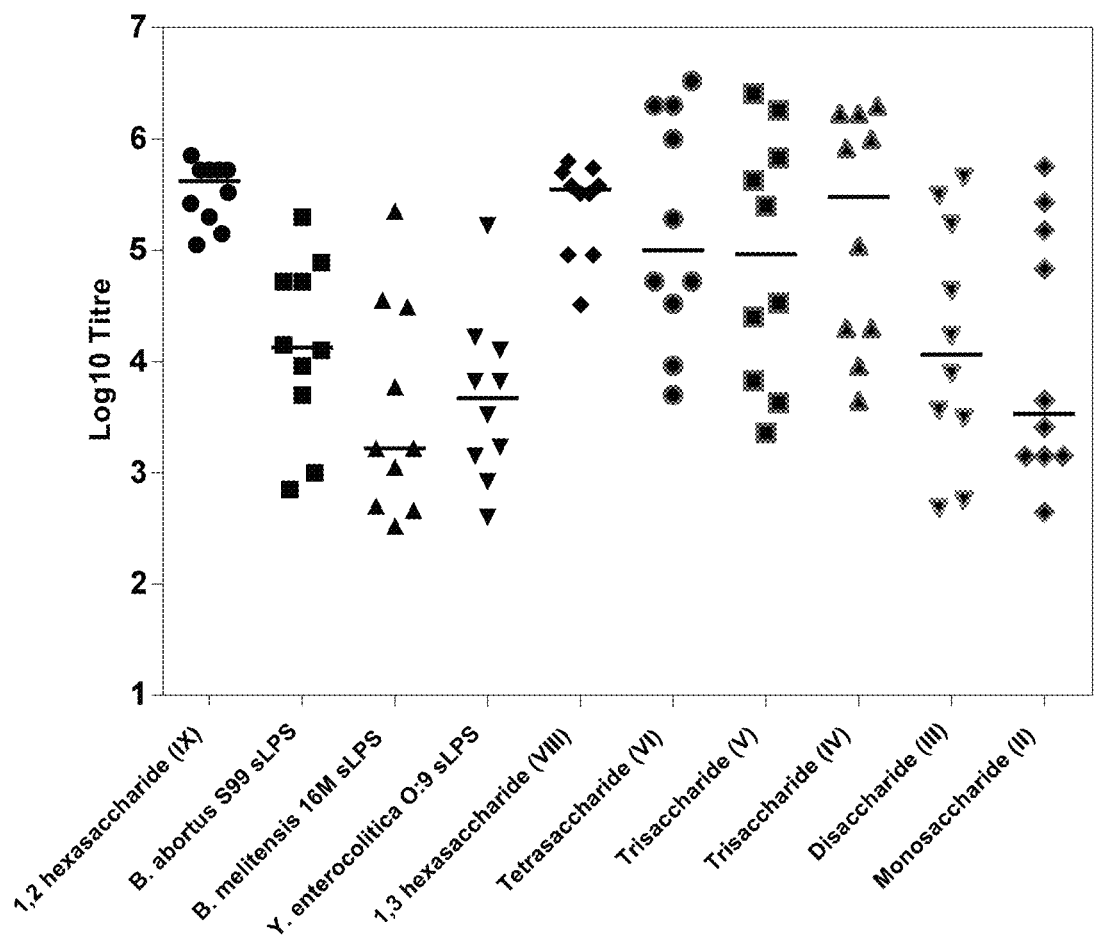
FIG. 1 shows the antibody binding profile, shown as end point titre on iELISA, of sera from mice vaccinated with TT-dsg-1,2hexa (Structure I) against different synthetic oligosaccharide BSA conjugates (1-2 hexasaccharide=Structure IX; 1-3 hexasaccharide=Structure VIII; Tetrasaccharide=Structure VI; Trisaccharide=Structure V; Trisaccharide=Structure IV; Disaccharide=Structure III; Monosaccharide=Structure II), as well as against different sLPS antigens (*B. abortus* S99; *B. melitensis* 16M sLPS; *Y. enterocolitica* O:9 sLPS)

Example 1: Initial Work to Develop a Possible Vaccine Candidate

The work disclosed in WO2014/170681 and in (Ganesh et al (2014) Journal of the American Chemical Society 136: 16260-16269) and (McGiven et al (2015) Journal of Clinical Microbiology 53:1204-1210) suggested that it may be possible to develop a vaccine formed by chains of 4,6-dideoxy-4-formamido-α-D-mannopyranose units which are exclusively $C_1$-$C_2$ linked. This is because the shorter oligosaccharides described in those publications (such as di- or tetra-saccharides), that contain a single $C_1$-$C_3$ link and a limited number of $C_1$-$C_2$ links, were observed to be less likely to bind to antibodies induced by polysaccharides that are exclusively $C_1$-$C_2$ linked. It was suggested that vaccination with an exclusively $C_1$-$C_2$ linked polysaccharide would then be capable of discrimination from an animal infected with an organism having an OPS where $C_1$-$C_3$ links are present.

Therefore, initial experiments were carried out in which mice were immunised with an exclusively $C_1$-$C_2$ linked hexasaccharide, conjugated to tetanus toxoid, via a disuccinimidyl glutarate (DSG) linker (Structure I). Structure I is referred to as "TT-dsg-1,2hexa".

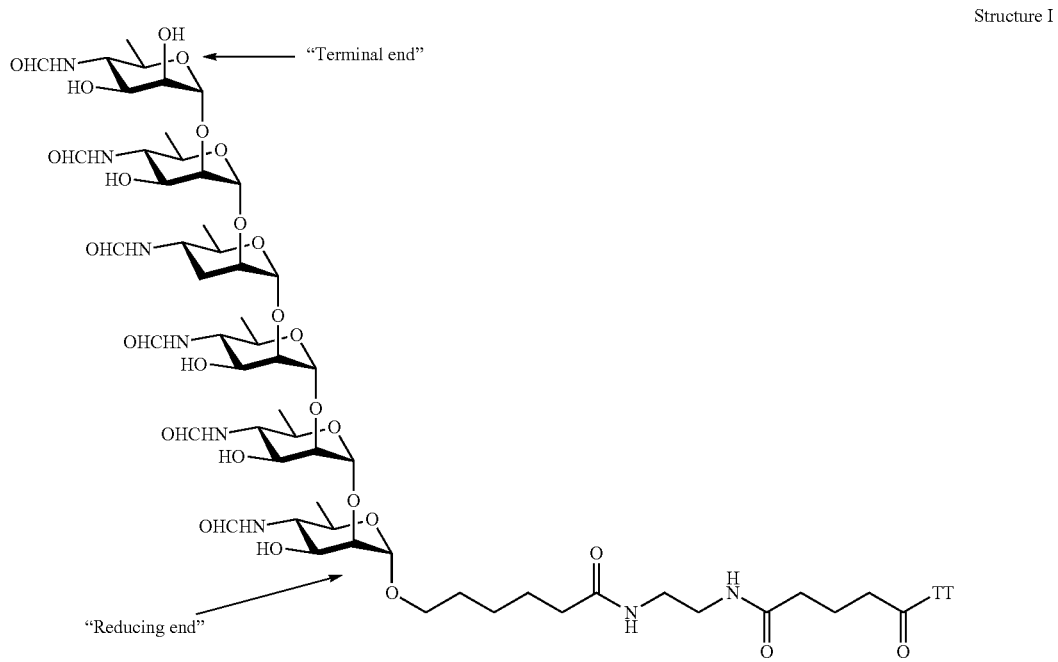

Structure I

It was expected that these constructs would only raise antibodies against A and C/Y epitopes, but not against M epitopes, because of the lack of a $C_1$-$C_3$ link.

After immunising mice with TT-sq-1,2hexa and TT-dsg-1,2hexa, sera from the animals was tested against BSA-conjugated 1,2 hexasaccharide (Structure IX) and, as expected, showed a good response. The sera was also tested against the native bacterial antigens of lipopolysaccharides (LPS) from *Brucella abortus, Brucella melitensis* and *Yersinia enterocolitica* O:9 and, again, good responses were observed.

Sera were then tested with various synthetic oligosaccharide conjugate antigens as previously described, shown as Structures II, III, IV, V, VI, VII and IX in Table 2 below (in which, in the third column, "S" indicates a 4,6-dideoxy-4-formamido-α-D-mannopyranose unit, S2S indicates neighbouring units linked by $C_1$-$C_2$ and S3S indicates neighbouring units linked by $C_1$-$C_3$).

Surprisingly, it was found that the immunised sera were recognising the antigens including a $C_1$-$C_3$ glycosidic linkage, although there was no $C_1$-$C_3$ linkage present in the immunising antigen (FIG. 1).

The unexpected antibody response to even the monosaccharide antigen (Structure II) led the inventors to conclude that development of the originally proposed DIVA vaccine would fail, since any oligosaccharide, irrespective of the presence or absence of $C_1$-$C_3$ links, would induce such a response as a minimum.

TABLE 2 synthetic oligosaccharide BSA conjugates

| | Structure number | Pattern of sugars/ linkages | Structure |
|---|---|---|---|
| Mono-saccharide | II | S | 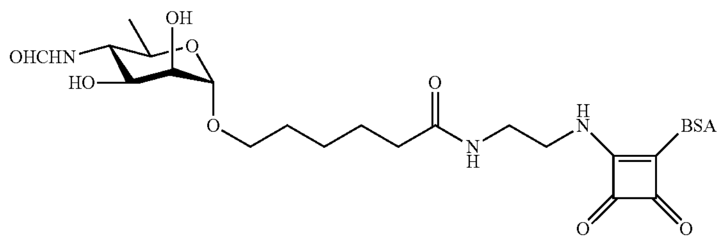  |
| Disaccharide ($C_1$-$C_3$ linked) | III | S3S | 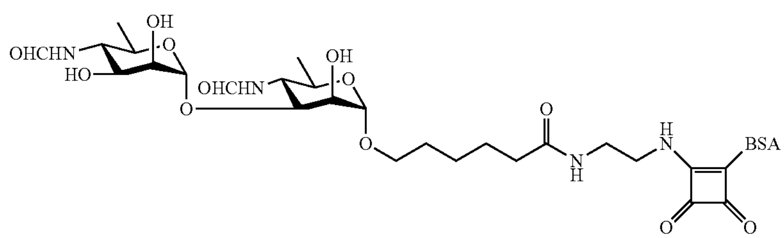  |
| Trisaccharide | IV | S2S3S | 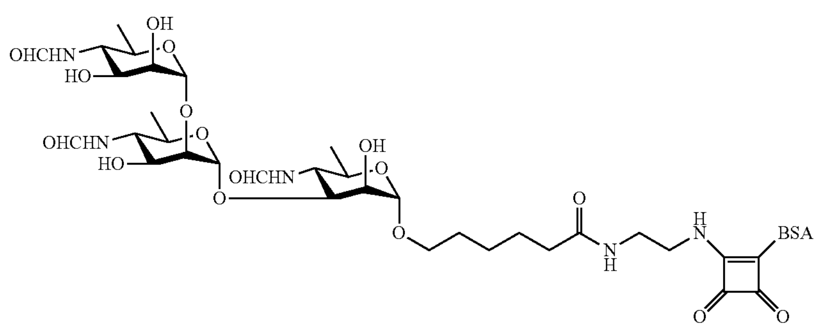  |
| Trisaccharide | V | S3S2S | 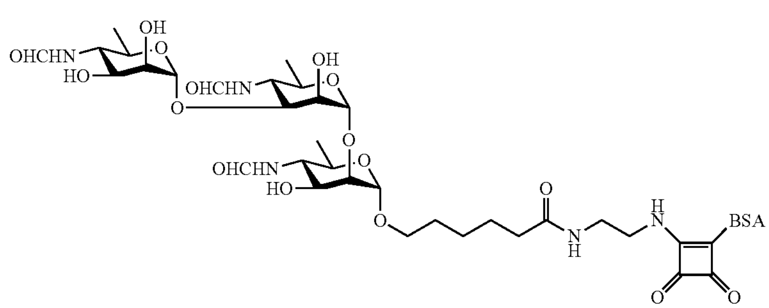  |

TABLE 2-continued synthetic oligosaccharide BSA conjugates

| | Structure number | Pattern of sugars/ linkages | Structure |
| --- | --- | --- | --- |
| Tetra-saccharide | VI | S2S3S2 S | 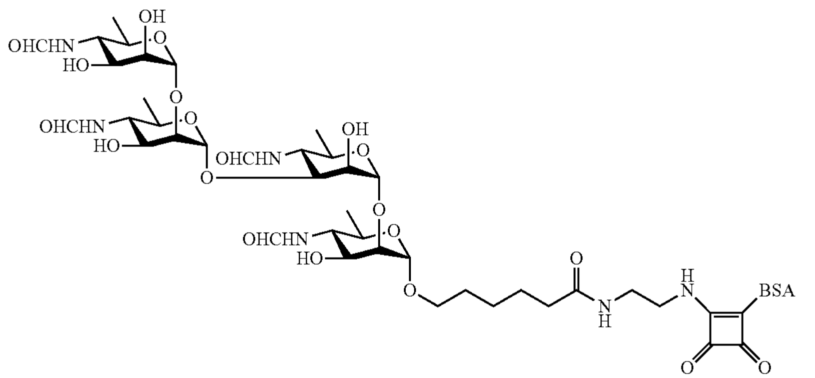 |
| Penta-saccharide | VII | S2S3S2 S2S | 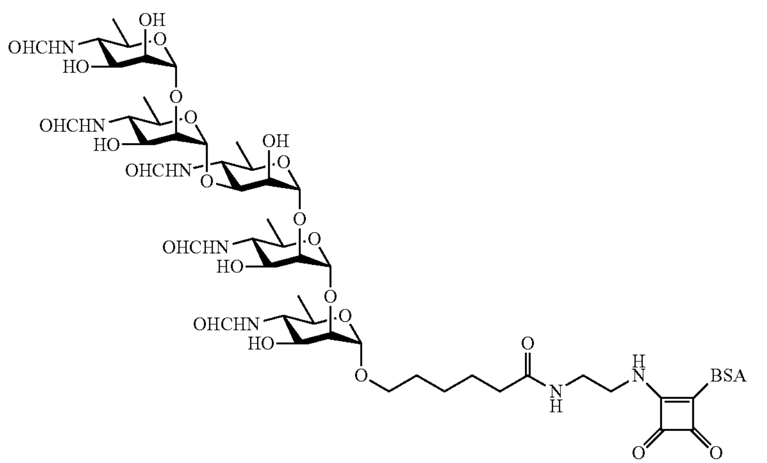 |
| Hexa-saccharide | VIII | S2S3S2 S2S2S | 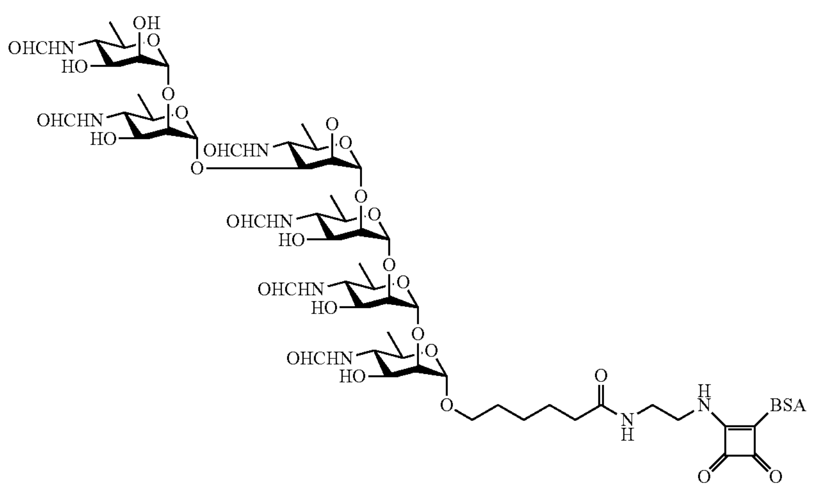 |

TABLE 2-continued
synthetic oligosaccharide BSA conjugates
| | Structure number | Pattern of sugars/ linkages | Structure |
|---|---|---|---|
| Hexa-saccharide | IX | S2S2S2 S2S2S | 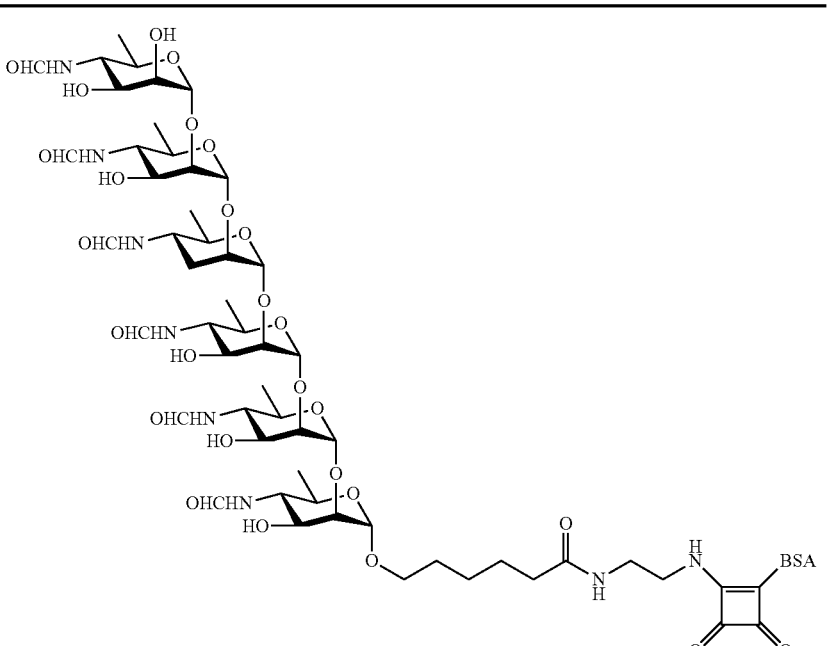 |
| Trisaccharide (DSG linked) | X | S2S3S | 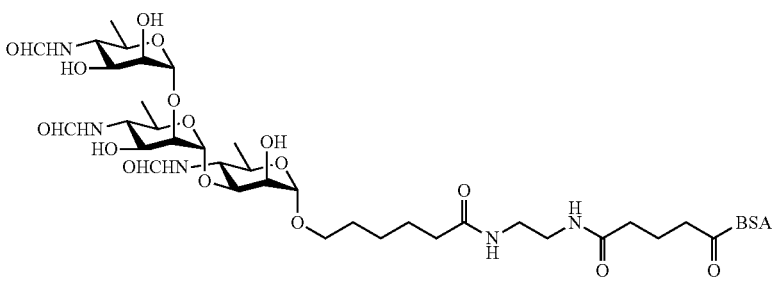 |
| Disaccharide ($C_1$-$C_2$ linked) | XI | S2S | 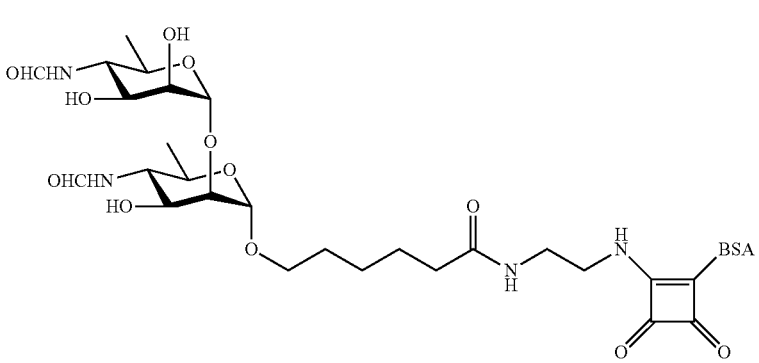 |

TABLE 2-continued synthetic oligosaccharide BSA conjugates

| | Structure number | Pattern of sugars/ linkages | Structure |
|---|---|---|---|
| Trisaccharide (exclusively $C_1$-$C_2$ linked) | XII | S2S2S | 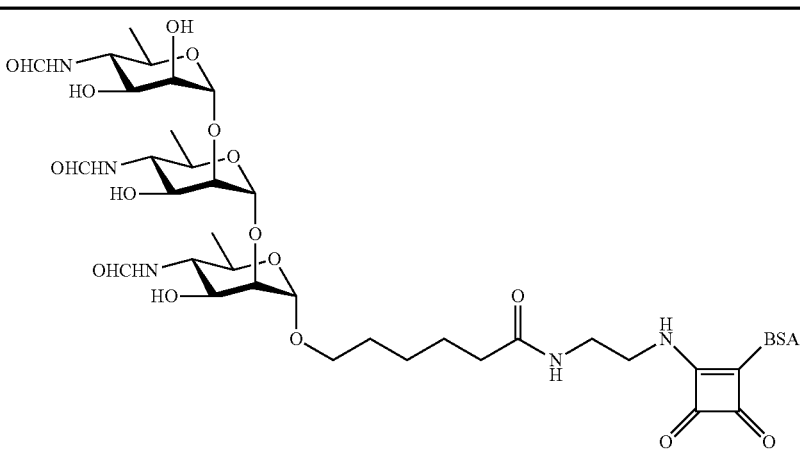 |

Methods Used for Example 1

Animal: Female CD1 mice (Charles River, Canada) of 6-8 weeks old were used to study the immune response. All the procedures and experiments involving animals were carried out using a protocol approved by the Animal Care Committee, Faculty of Bioscience, University of Alberta. The protocol was approved as per the Canadian Council on Animal Care (CCAC) guidelines.

Antigen: All synthetic oligosaccharide antigens were produced as described previously (Ganesh et al (2014) Journal of the American Chemical Society 136:16260-16269) or in the Appendix below. For animal experiments, a hexasaccharide of six units of perosamine all linked via 1,2 glycosidic bonds were conjugated to Tetanus toxoid (TT) using dsg-linker (disuccinimidyl glutarate), to form the molecule having Structure I above (also referred to as "TT-dsg-1,2hexa"). The hexasaccharide was synthesised with a reducing end amine terminated linker (Ganesh et al (2014) Journal of the American Chemical Society 136:16260-16269). A mixture of hexasaccharide and DSG (15 eq.) in DMF and 0.1 M PBS buffer (4:1, 0.5 mL) was stirred at room temperature for 6 h. The reaction mixture was concentrated under vacuum and the residue was washed with EtOAc 10 times to remove the excess DSG. The resultant solid was dried under vacuum for 1 h to obtain DSG activated oligosaccharide. Activated hexasaccharide (0.518 μmol) was added to the solution of tetanus toxoid (0.025 μmol) in 0.5 M borate buffer pH 9 and stirred slowly at 21° C. for 3 days. Then the reaction mixture was washed with PBS buffer, filtered through a millipore filtration tube (10,000 MWCO, 4×10 mL) and the resulting tetanus toxoid-conjugate was stored in PBS buffer. The MALDI-TOF mass spectrometry analysis indicated the conjugate had an average of 11.7 hexasaccharides per tetanus toxoid.

For screening the immune response via ELISA, the same hexasaccharide was conjugated to a different carrier protein, namely, bovine serum albumin (BSA), using squarate chemistry (Ganesh et al (2014) Journal of the American Chemical Society 136:16260-16269) as described previously (e.g., WO2014/170681), to form Structure IX. Additionally, immune responses were also screened using different synthetic oligosaccharides (Structures II-VI and Structure VIII in Table 1). Different native sLPS from *Brucella abortus*, *Brucella melitensis* and *Yersinia enterocolitica* were also used.

Vaccine formulation: Alum was prepared freshly at the very beginning of the immunization by following a published protocol (Lipinski et al (2012) Vaccine 30:6263-6269). Briefly, the solutions of 0.2 molar $KAl(SO_4)_2 \cdot 12H_2O$ and 1.0 molar $NaHCO_3$ were prepared separately and filter sterilised. Then 10 mL of the second solution (bicarbonate solution) was added quickly to a 20 mL of the first solution with vigorous shaking. To avoid any material loss due to effervescence, the mixing step was carried out in a 200 mL beaker. The resulting alum precipitate was washed with PBS (which had previously been filtered and sterilised by autoclave) and spun down at 4000 g for 7 min. This washing cycle was continued till the pH of the supernatant was identical with PBS (pH 7.3). Finally, the alum was suspended in PBS at 50 mg/mL concentration, thimerosal (0.01% w/v) was added and the mixture stored at 4° C.

Alum was mixed with the TT-conjugate in 5:1 weight ratio and the mixture was allowed to rock overnight before administering on animals.

Immunization: Animals were immunised thrice at an interval of 21 days. A total volume of 250 μl comprising 12 μg TT-dsg-1,2hexa (equivalent to 1 μg of 1,2 hexasaccharide) was injected on each mouse of which 150 μl was injected inter peritoneally and the rest 100 μl was injected subcutaneously. Pre bleed were collected before the immunisation started. The animals were euthanized at the 10th day after final injection and final bleed was collected.

Serum processing: After collection, murine blood was incubated at 37° C. for one hour then spun at 1500 g for 10 min. Clear serum form the top was collected and stored at −20° C. until use.

Immunoassays: Antibody levels in the murine sera were studied using enzyme linked immuno-sorbent assay (ELISA). A published protocol (Bundle et al (2014) Bioconjugate Chemistry 25:685-697) was followed with little modification. Briefly, polystyrene microtiter plates were incubated with the coating antigen (1 μg/mL, 100 μL/well) at 4° C. overnight, then washed (5×) with PBST (0.05% Tween-20 in phosphate buffer saline, PBS). Then murine sera were added to the coated well at a serial √10 fold dilutions (100 μL/well). The starting dilution for the sera was 1:100. After incubation at room temperature for 2 h, the plates were washed (5×) with PBST. Then the plate was incubated with 100 μL/well of 1:5000 diluted goat anti-mouse IgG antibody, tagged with HRPO (KPL, 1.0 mg/mL stock) for 30 min at room temperature, then washed (5×) with PBST. A peroxidase substrate, 3,3',5,5'-Tetramethyl-benzidine (TMB) with $H_2O_2$, was added. After 15 min the reaction was quenched by addition of phosphoric acid (1M, 100 μL/well). The plates were read at 450 nm and the data were processed using Origin software. 0.1% BSA in PBST was used to dilute all sera. End point dilution ($x_0$) was recorded as the serum dilution giving an absorbance 0.2 above background and serum titer was calculated as reciprocal of $x_0$. All the data were processed using Origin 9 and GraphPad Prism softwares.

Example 2: Investigation of Possible Epitope at Non-Reducing End of 4,6-dideoxy-4-formamido-α-D-mannopyranose Chain Since the inventors were observing binding of antibodies raised against Structure I to even a monosaccharide antigen (Structure II), it was suspected that the terminal sugar provided an epitope for antibody binding (referred to herein as a "terminal epitope"). To investigate whether the binding potential of a single perosamine (4,6-dideoxy-4-formamido-α-D-mannopyranose) was dependent upon the specific structural features possessed only by the terminal perosamine (for example, the hydroxyls located on both C2 and C3), various synthetic oligosaccharides comprising a "cap" structure at the non-reducing end were prepared as shown below in Table 3. Some oligosaccharides were linked to BSA using squarate chemistry and some via DSG, as above.

TABLE 3 further synthetic oligosaccharide BSA conjugates, providing "cap" structures on the terminal perosamine

| | Structure number | Pattern of sugars/ linkages | Structure |
|---|---|---|---|
| Mannose-linked mono-saccharide | XIII | S | 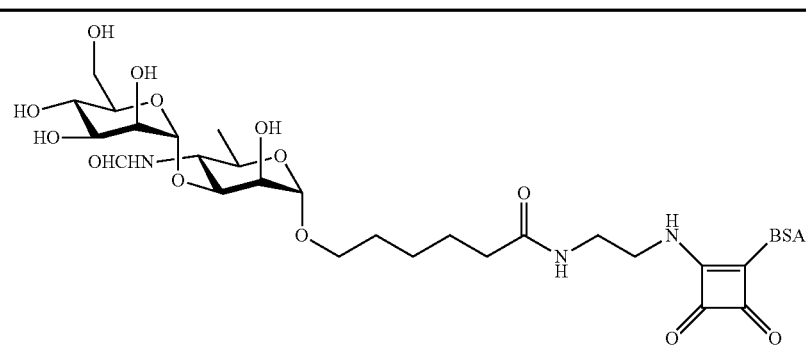 |
| Mannose-linked trisaccharide | XIV | S3S2S | 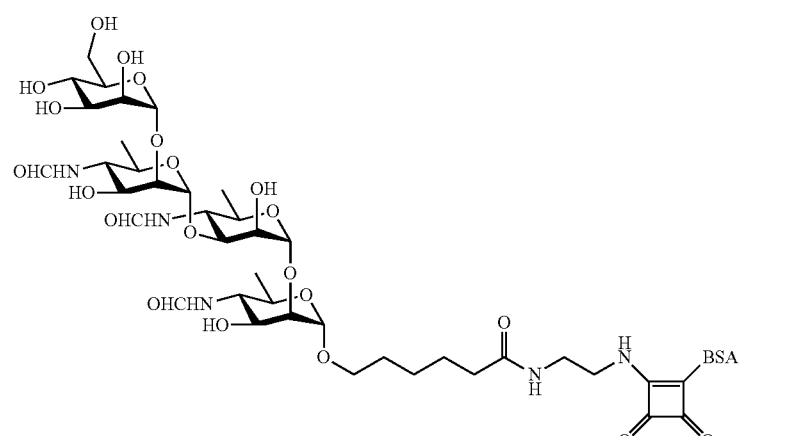 |
| Methoxy-modified disaccharide | XV | S3S | 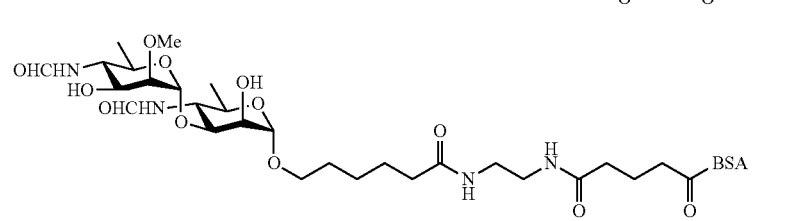 |

TABLE 3-continued further synthetic oligosaccharide BSA conjugates, providing "cap" structures on the terminal perosamine

| | Structure number | Pattern of sugars/ linkages | Structure |
|---|---|---|---|
| Double methoxy-modified disaccharide | XVI | S3S | [structure image] |
| Methoxy-modified trisaccharide | XVII | S2S3S | [structure image] |
| Mannose-linked penta-saccharide | XVIII | S2S2S2S2S | [structure image] |

Figure 2:
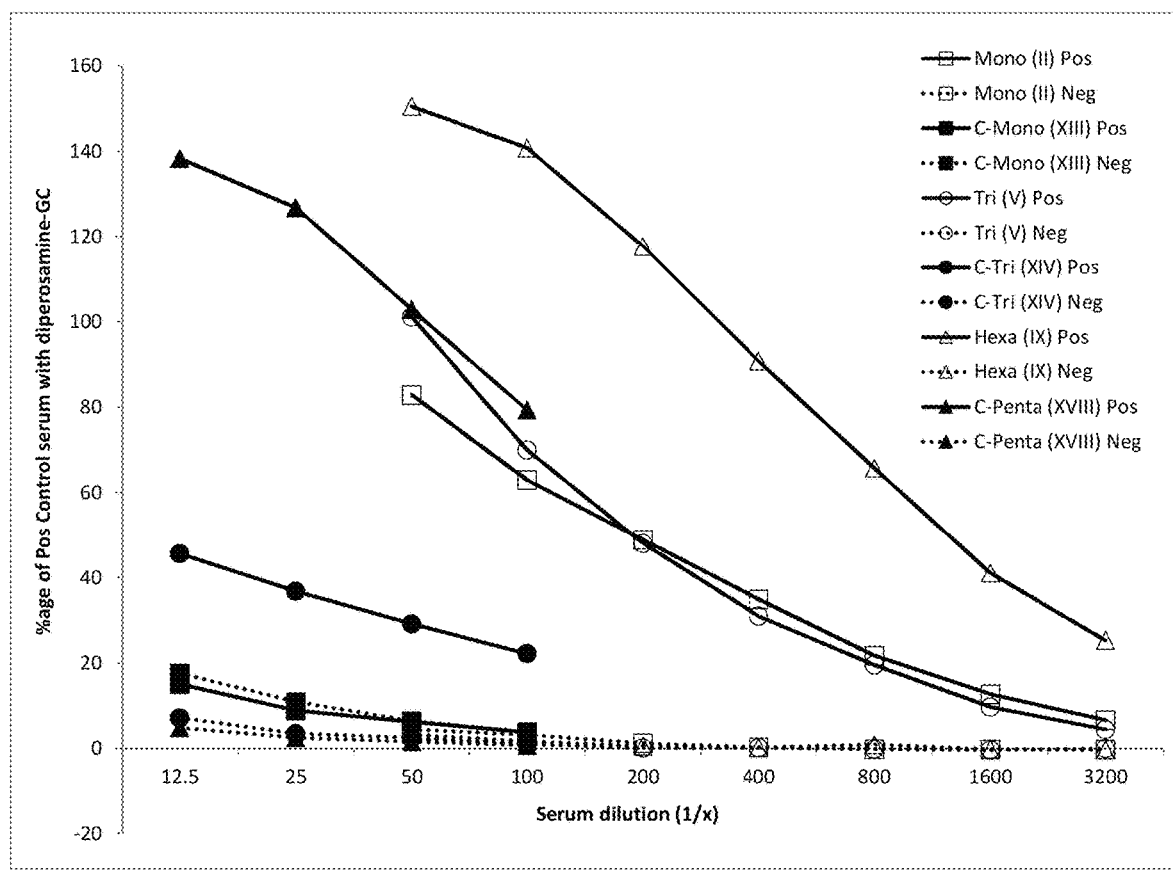
FIG. 2 shows serological iELISA titres of cattle sera using mannose modified and equivalent non-modified oligoperosamine BSA conjugates (Mono=Structure II; C-Mono=Structure XIII; Tri=Structure V; C-Tri=Structure XIV, Hexa=Structure IX; C-Penta=Structure XVIII; "Pos" indicates sera from a known infected animal and "neg" indicates sera from a known uninfected animal)

Sera from field infected cattle were tested with a selection of the above structures (FIG. 2). This showed that modifying the non-reducing end of the sugar chain did have an impact on the serological reactivity of the oligosaccharide antigen. This effect was greater with shorter oligosaccharides, suggesting that, as the linear epitope becomes longer, the impact on antibody binding of losing the terminal epitope is proportionally reduced.

The "positive" data points in FIG. 2 represent the average result from 6 serum samples from infected animals that are positive to conventional serological assays. The "negative" data points represent the average result from 2 serum samples that are negative in such assays. In the positive samples, the average result for the monosaccharide (Structure II) antigen at 1/100 serum dilution was approximately 60%. The equivalent result for the modified monosaccharide (Structure XIII) was approximately 5%. The reduction in titre was at least 64 fold and there was no difference between the negative and the positive sera when the modified monoperosamine (Structure XIII) was used. In contrast, when the non-modified monoperosamine (Structure II) was used, a difference was observed. Therefore, it appeared that none of the antibodies that bound to Structure II could bind the modified version, Structure XIII. The inventors concluded that the anti-*Brucella* OPS antibody repertoire within these samples included antibodies that bind to a single 4,6-dideoxy-4-formamido-α-D-mannopyranose unit, but this binding is only possible when the sugar unit is at the terminal position. The ability of these antibodies to bind is severely impeded, once 4,6-dideoxy-4-formamido-α-D- mannopyranose is no longer available as a terminal sugar unit, but only within a linear arrangement.

There was a similar picture when the trisaccharides were evaluated although the contrast between the modified (Structure XIV) and non-modified (Structure V) antigens was not so extreme (a 4-8 fold reduction in titre). Presumably, the less extreme contrast reflects the increased capability of the trisaccharide within Structure XIV to act as a linear antigen. This pattern is also observed with the 1-2 hexasaccharide (Structure IX) and modified 1-2 pentasaccharide (Structure XVIII).

On the basis of this evidence, the inventors concluded that there was a significant subset of anti-OPS antibodies whose antigen binding to short oligosaccharides was dramatically affected by the presence or absence of a terminal 4,6-dideoxy-4-formamido-α-D-mannopyranose unit.

Similar experiments were carried out using the same serum from *B. abortus* infected cattle, using various oligosaccharide antigens modified by replacement of the $C_2$—OH (hydroxyl) group on the terminal perosamine by an —OMe group. The overall results are summarised in Table 4 below.

Table 5 below shows more serological data from the application of the synthetic antigens to sera from cattle infected with *B. abortus* (n=20), "infected" samples, and sera from uninfected cattle (n=20) "non-infected" samples. The mannose-linked monosaccharide (Structure XIII) and mannose-linked trisaccharide (Structure XIV) antigens have poor diagnostic properties (low AUC [Area Under the dose response Curve] values), as they ineffectually differentiate between the "infected" and "non-infected" samples. Structure XIII is especially poor, set against the remarkable and completely unexpected diagnostic attributes of the non-modified (i.e., un-capped) monosaccharide (Structure II).

TABLE 4

Results from 6 serum samples from *B. abortus* infected cattle

| Antigen | Strong pos | Weak pos | Negative |
| --- | --- | --- | --- |
| monosaccharide squarate (Structure II) | 6 | 0 | 0 |
| 1-3 disaccharide squarate (Structure III) | 6 | 0 | 0 |
| t1-2 trisaccharide squarate (Structure IV) | 6 | 0 | 0 |
| t1-2 trisaccharide dsg (Structure X) | 6 | 0 | 0 |
| t1-3 trisaccharide squarate (Structure V) | 6 | 0 | 0 |
| Exclusively 1-2 hexasaccharide squarate (Structure IX) | 6 | 0 | 0 |
| mannose-linked exclusively 1-2 pentasaccharide squarate (Structure XVIII) | 5 | 1 | 0 |
| mannose-linked t1-3 trisaccharide squarate (Structure XIV) | 2 | 2 | 2 |
| OMe-modified t1-2 trisaccharide dsg (Structure XVII) | 2 | 2 | 2 |
| OMe-modified 1-3 disaccharide dsg (Structure XV) | 1 | 2 | 3 |
| mannose-linked monosaccharide squarate (Structure XIII) | 0 | 1 (very weak) | 5 |

On the basis of the results shown in Table 5, the inventors concluded that even the inclusion of a single OMe group to the C2 of the terminal monosaccharide was sufficient to abrogate much of the antibody response. This supported the concept that the terminal 4,6-dideoxy-4-formamido-α-D-mannopyranose was a specific structure distinct, in terms of antibody recognition, from a linear polymer of 4,6-dideoxy-4-formamido-α-D-mannopyranose units.

TABLE 5

Diagnostic performance attributes ($YI_{max}$ with DSn, DSp and AUC) for samples from animals culture Positive for *B. abortus* vs random field non-infected samples

| Antigen | YImax | DSn | DSp | AUC |
| --- | --- | --- | --- | --- |
| Mannose-linked monosaccharide (Structure XIII) | 26.16 | 75 | 51.16 | 0.5558 |
| Mannose-linked trisaccharide (Structure XIV) | 53.02 | 60 | 93.02 | 0.7733 |
| Mannose-linked pentasaccharide (Structure XVIII) | 78.72 | 95 | 83.72 | 0.9605 |
| Monosaccharide (Structure II) | 83.02 | 90 | 93.02 | 0.9663 |
| Hexasaccharide (Structure IX) | 95 | 95 | 100 | 0.9942 |
| Pentasaccharide (Structure VII) | 100 | 100 | 100 | 1.00 |
| Nonasaccharide (Structure XIX below) | 100 | 100 | 100 | 1.00 |
| Disaccharide (Structure III) | 100 | 100 | 100 | 1.00 |
| Tetrasaccharide (Structure VI) | 100 | 100 | 100 | 1.00 |

(DSn = Diagnostic Sensitivity (%); DSP = Diagnostic Specificity (%); AUC = Area Under the (ROC) Curve; ROC = Receiver Operator Characteristic; YI = Youden Index (DSn + DSp − 100); YImax = the maximum YI value that can be achieved with variation of the +/− cut-off.)

Therefore, the inventors proposed that the response to the modified oligosaccharides from serum from infected animals might be similar to the response to the non-modified oligosaccharides from serum from animals immunised with antigens that possessed no tip epitope (i.e., no terminal 4,6-dideoxy-4-formamido-α-D-mannopyranose). In the first case, only the anti-linear antibodies would bind and the response would be low (very low with the short oligosaccharides). In the second case, there would be no anti-tip antibodies to bind and, therefore, the only response observed would be due to anti-linear antibodies. The response of these antibodies against the short oligosaccharides would also be low.

Methods Used for Example 2

Antigen: Oligosaccharides of perosamine were conjugated to Tetanus toxoid (TT) using dsg-linker (disuccinimidyl glutarate) or using squarate chemistry, as described above.

Bovine serology studies: Antibody levels in bovine sera were studied using enzyme linked immuno-sorbent assay (ELISA) as described previously (McGiven et al (2015) Journal of Clinical Microbiology 53:1204-1210).

Figure 3:
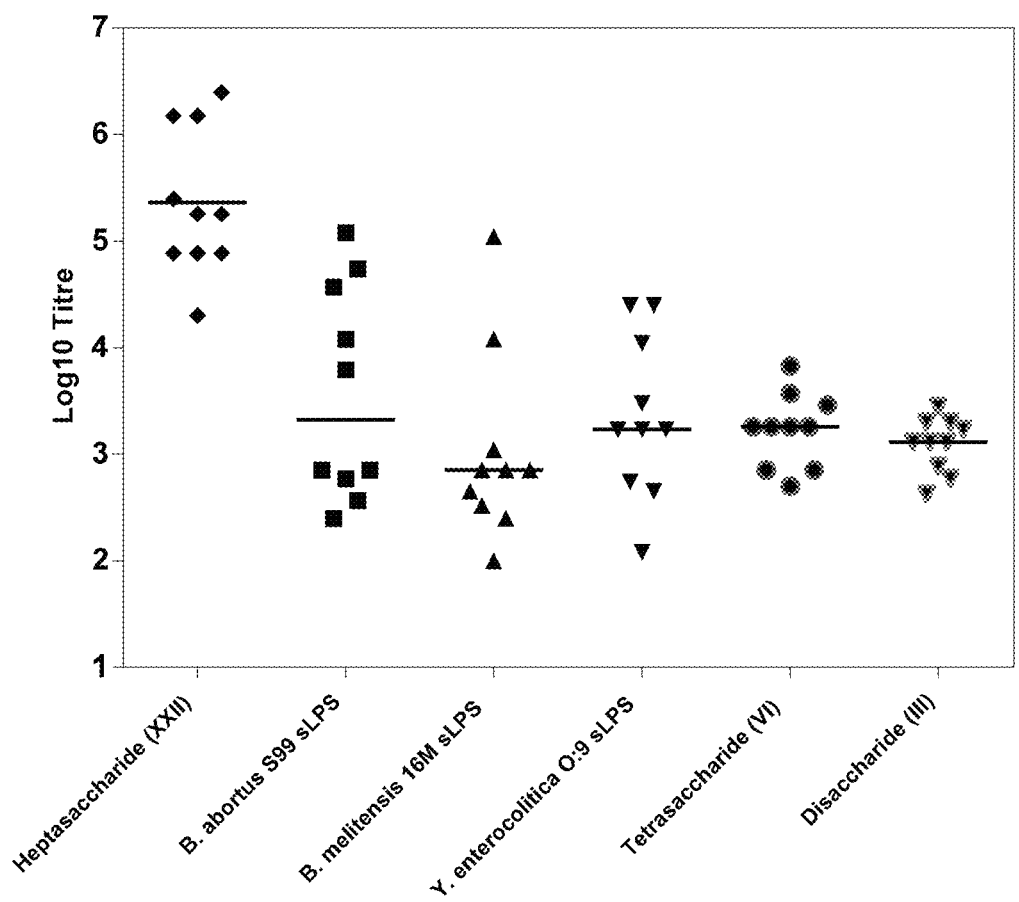
FIG. 3 shows the antibody binding profile, shown as end point titre on iELISA, of sera from mice vaccinated with TT-dsg-1,2-hepta$_{(non-red)}$ (Structure XXI) against different synthetic oligosaccharide conjugates (Heptasaccharide=Structure XXII; Tetrasaccharide=Structure VI; Disaccharide=Structure III) and different sLPS antigens (*B. abortus* S99; *B. melitensis* 16M sLPS; *Y. enterocolitica* O:9 sLPS)
Figure 5:
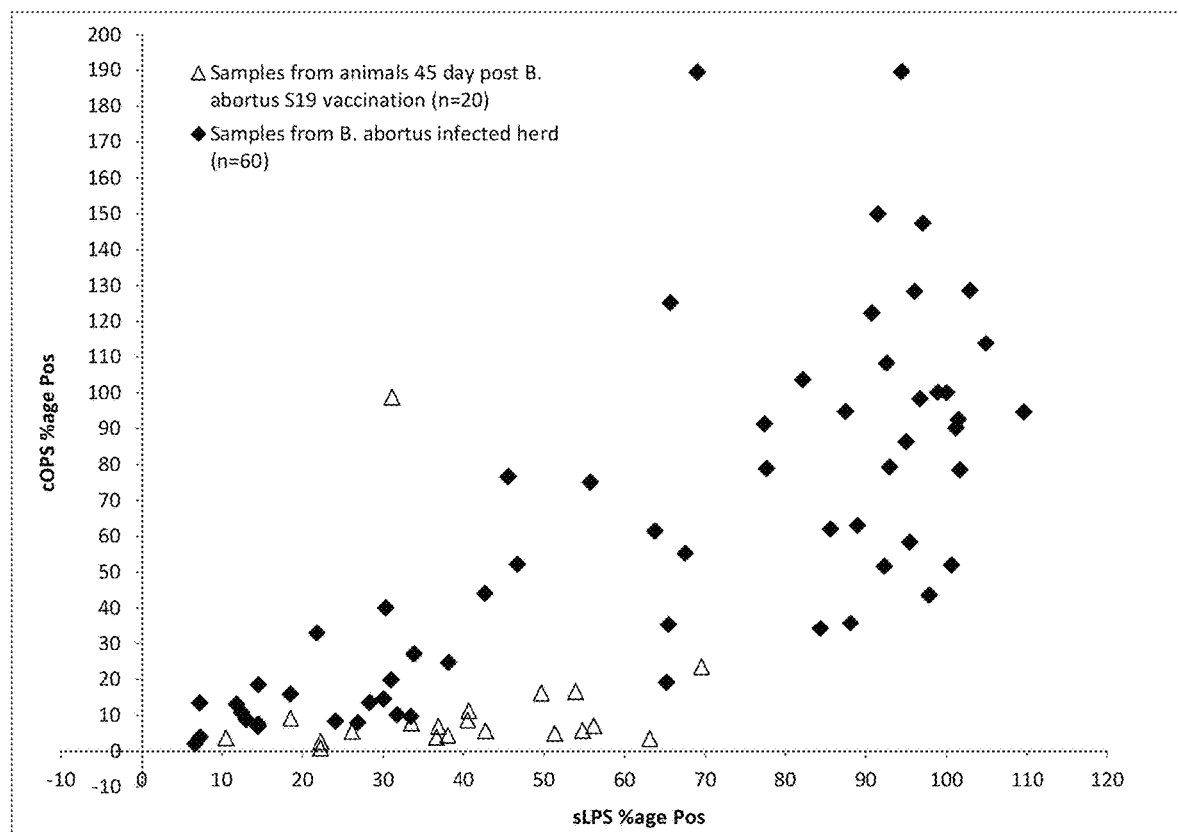
FIG. 5 shows iELISA results using *B. abortus* S99 sLPS (x-axis) and conjugated (c) *B. abortus* S99 OPS (y-axis) antigens (the process of conjugation having applied a cap to the OPS antigen) for 20 serum samples collected from cattle 45 days after vaccination with *B. abortus* S19 (open triangles) and 60 samples from cattle from herds infected with field strains of *B. abortus* (closed diamonds)

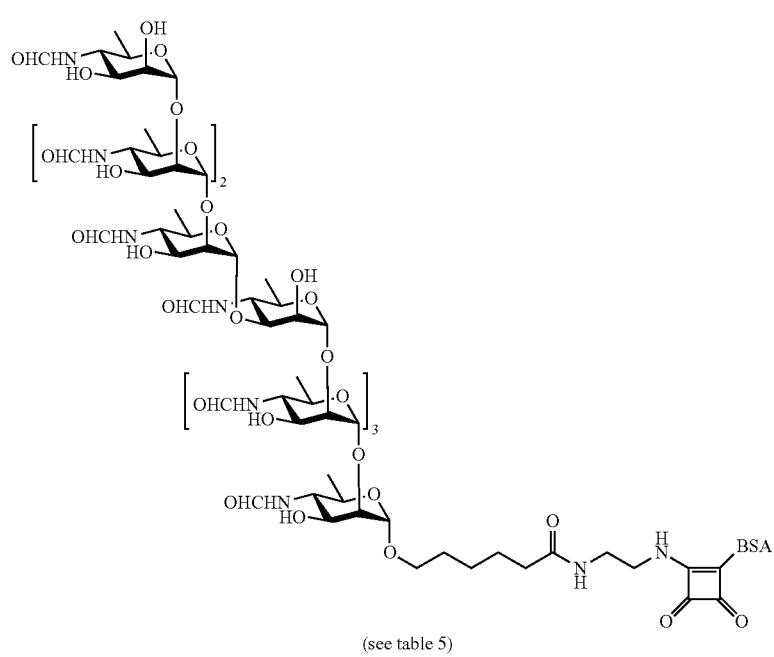

Structure XIX (see table 5)

Example 3: Oxidation of OPS Terminal End Sugar to Disrupt Terminal Epitope

The inventors adapted the disclosure of Stefanetti et al. (Stefanetti et al (2014) Vaccine 32:6122-6129) to disrupt the structure of the terminal sugar in *Brucella* OPS. These workers subjected the OPS of *Salmonella Typhimurium* to mild oxidation with sodium metaperiodate. This opens the rhamnose ring to generate aldehydes, which can then be conjugated to the amines on CRM197 (genetically detoxified Diphtheria toxin) via reductive amination. The rhamnose sugar in that method is an internal sugar, rather than a terminal sugar. Therefore, the oxidation is possible because the polymer is linked via $C_1$ and $C_4$, so that the cis vicinal hydroxyl groups on $C_2$ and $C_3$ are available for oxidation. In the case of *Brucella*, the perosamines have a D-rhamnose framework (like D-mannose, but lacking OH on $C_6$) but, because each non-terminal rhamnose in *Brucella* OPS is linked to its terminal end neighbour through either $C_2$ or $C_3$, the only rhamnose with cis vicinal hydroxyl groups on $C_2$ and $C_3$ is the terminal one.

Therefore, use of a similar method on the *Brucella* OPS can be used to generate a terminal structure shown below (Structure XX).

Methods Used for Example 3

*Brucella* OPS (from *B. abortus* S99 and *B. suis* biovar 2 [strain Thomsen]) was purified by hot-phenol extraction (Westphal et al (1952) Uber die Extraction von Bakterien mit Phenol/Wasser. Z. Naturforsch. 7:148-155) followed by mild acid hydrolysis and size exclusion chromatography (Meikle et al (1989) Infect Immun 57:2820-2828). The OPS for TT conjugation was oxidised at 2 mg/ml conc in 10 mM sodium metaperiodate (SMP) & 50 mM sodium acetate buffer (pH 5.5) for 1 hr in the dark. This was sufficient to oxidise the vicinal diol hydroxyl groups on the $2^{nd}$ and $3^{rd}$ carbons of the terminal sugar. Residual SMP was removed by desalting using a PD-10 column (Sephadex-G25 column) according to the manufacturer's instructions (GE Healthcare). A suitable volume of elution buffer allowed the OPS to flow through.

Structure XX

Example 4: Vaccination with Capped Hexasaccharide

In view of the apparent importance of the tip epitope in antibody generation, a heptasaccharide linked to TT via the non-reducing terminal end of the sugar chain was prepared (TT-dsg-1,2-hepta$_{(non\text{-}red)}$) (Structure XXI). This conjugation method disrupts the tip epitope, as no terminal 4,6-dideoxy-4-formamido-α-D-mannopyranose is available. The structure is Structure XXI below.

Therefore, this is a hexasaccharide capped with a structure which is not 4,6-dideoxy-4-formamido-D-mannopyranose.

Mice were immunised using this conjugate and sera were evaluated by iELISA against various antigens. FIG. 3 shows the results. Comparative results from Example 1, for the TT-dsg-1,2hexa (Structure I) vaccinated animals, are shown in FIG. 1. This demonstrates that vaccination with Structure XXI, with the tip epitope disrupted, produces antibodies with significantly reduced binding affinity for the proposed diagnostic conjugate antigens (di- and tetra-saccharides, Structures III and VI respectively). However, a reaction is still present against the disaccharide and tetrasaccharide antigens, indicating that TT-dsg-1,2-hepta$_{(non-red)}$ (Structure XXI) is also not suitable for use as a vaccine within a DIVA test system.

Structure XXI

Methods Used for Example 4

Animals; Vaccine formulation; Immunization; Serum processing; Immunoassays: All as described above for Example 1.

Antigen: The 4,6-dideoxy-4-formamido-α-D-mannopyranose hexasaccharide was prepared according to methods described previously (Eis & Ganem (1988) Carbohydrate Research 176:316-323).

For screening the immune response via ELISA, the same heptasaccharide was conjugated to bovine serum albumin (BSA), as described previously (e.g., WO2014/170681). The resulting heptasaccharide (in fact, a "capped" hexasaccharide) has the following structure:

Structure XXII

The further synthesis and conjugation methods used to prepare the TT-dsg-1,2-hepta$_{(non-red)}$ (Structure XXI) and BSA-dsg-1,2-hepta$_{(non-red)}$ (Structure XXII) can be found in the Appendix below.

Additionally, immune responses were also screened using different synthetic oligosaccharides (Structures III, VI and IX), as well as different native bacterial cell wall antigens from *Brucella abortus* and *Yersinia enterocolitica* O:9.

Example 5: Vaccination with Tip-Conjugated Polysaccharide

The inventors next attempted vaccination using a much longer polysaccharide, conjugated to the protein carrier via the non-reducing tip end, in a further attempt to obtain a vaccine which would be useable within a DIVA testing system. The object was to obtain a vaccine molecule which would generate antibodies which will not bind to the proposed diagnostic conjugate antigens (di- and tetra-saccharides, Structures III and VI respectively). As described in WO2014/170681, these antigens are already useful to distinguish between animals infected with *Brucella* and animals which are uninfected or infected with *Yersinia enterocolitica* O:9 (or strains of *Brucella* which have an OPS lacking α1,3 glycosidic linkages).

Mice were immunised, as outlined below, with OPS from *B. abortus* S99 (which has approximately 2% α1,3 linkages) and OPS from *B. suis* by 2 strain Thomsen (a strain with exclusively α1,2 linked polysaccharide), both conjugated to TT via the terminal sugar. Therefore, the *B. abortus* S99-derived structure was Structure XXIII below, in which conjugation to TT is achieved via $C_3$, or a related structure in which conjugation to TT is achieved via $C_2$, or via both $C_2$ and $C_3$.

Structure XXIII
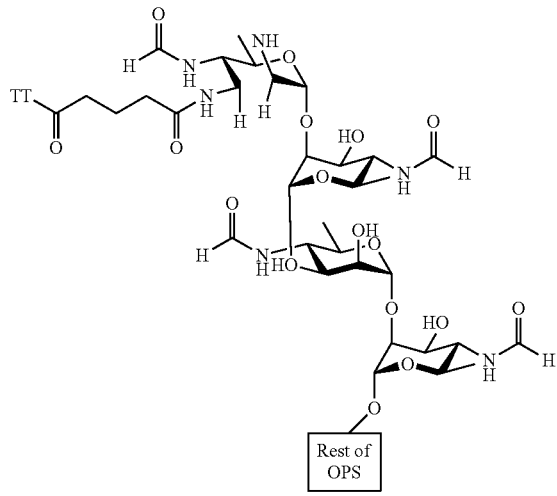

The *B. suis* by 2-derived structure was Structure XXIV, below. Again, in Structure XXIV conjugation to TT shown as achieved via $C_3$, but the *B. suis* by 2-derived structure may be a related structure in which conjugation to TT is achieved via $C_2$, or via both $C_2$ and $C_3$.

Structure XXIV

Final bleed sera from the animals were tested then against the bacterial antigens of lipopolysaccharides (LPS) from *B. abortus* S99 and *Brucella melitensis* strain 16M (about 20% α1,3 linkages), whole cell antigens from *B. abortus* S99, *B. melitensis* 16M and *B. suis* biovar 2, as well as against tetanus toxoid. The results are shown in FIG. 4. The sera were also tested against the synthetic antigens having Structure IX ("1,2 Hexasaccharide"), Structure VIII ("1,3 Hexasaccharide"), Structure VI ("Tetrasaccharide"), Structure XII ("exclusively 1,2 linked trisaccharide") and Structure III ("Disaccharide").

The trisaccharide (Structure XII) was included in the analysis so that, together with the exclusively 1,2 linked hexasaccharide (Structure IX), an evaluation could be made of how the length of the exclusively 1,2 linked oligosaccharide impacts upon the binding of antibodies induced by the glycoconjugate immunogens having Structures XXIII and XXIV. When the sera was tested at a 1/100 dilution the there was no reaction against the trisaccharide (Structure XII). The results showed at least a ten-fold difference in average titre between the hexasaccharide (Structure IX) and the trisaccharide (Structure XIII). The magnitude of this difference was greater than expected, in view of the fact that the exclusively 1,2 linked trisaccharide antigen is considered to be an anti-C/Y antibody epitope (Table 1) and that these antibodies were considered likely to be those responsible for the observed cross reactions between A-dominant (e.g. *B. abortus* S99) and M-dominant (e.g. *B. melitensis* 16M) serotypes of *Brucella* antigen.

In order to demonstrate that the antigens are capable of detecting antibodies induced by infection with *Brucella*, these trisaccharide (Structure XIII) and hexasaccharide antigens (Structure IX) were evaluated against sera from naturally and experimentally infected animals. The ELISA results for both antigens when tested against sera from 12 naturally *B. abortus* infected cattle and 4 non-*Brucella* infected cattle are shown in FIG. 6. This shows that both antigens are capable of detecting all of the sera from the infected animals, without reaction against the sera from the non-infected animals, indicating that they are useful as DIVA antigens. Furthermore, it shows that the difference in the results between the two antigens was very small; the average results were 138.6% for the hexasaccharide (Structure IX) compared to 125.9% for the trisaccharide (Structure XIII). The figure also shows the results for the monosaccharide (112.2%) (Structure II). The magnitude of these results was unexpected.

The results from the immunisations in mice with Structures XXIII and XXIV suggest that anti-tip epitope rather than anti-linear epitope antibodies are the primary types that bind to the short, exclusively 1,2-linked antigens. Prior to this evaluation, the absence of binding of antibodies induced by these structures to the shorter oligosaccharides containing the 1,3 link was thought to be primarily because the 1,3 link prevented antibodies against linear sequences of 1,2 links from binding; the tip epitope was thought to play an important but lesser role. The data now generated with the exclusively 1,2 linked trisaccharide shows that the tip epitope plays a more prominent role in serodiagnosis than previously thought.

Two of the exclusively 1,2 linked antigens (Structures VIII and XII, hexasaccharide and trisaccharide, respectively) were also tested against sera taken from four cattle experimentally infected with *Brucella abortus* strain 544 (an A-dominant strain); samples were taken on weeks 3, 7, 16, 24 and 53 weeks post infection. The average titres from these samples are shown in FIG. 7. For four of the five sampling dates the average results for the trisaccharide were higher than those for the hexasaccharide, and the results on the other date were very close. These results show that the exclusively 1,2 linked trisaccharide and hexasaccharide antigens have very similar, and very good, sensitivities when applied to sera taken from experimentally and naturally *Brucella*-infected cattle. The at least 10-fold difference observed between these two antigens when they are applied to sera from the mice immunised with Structure XXIII is therefore likely to be due to the nature of the antibodies induced by this immunisation, rather than any inherent differences in diagnostic sensitivity between the two antigens (as these are equal). The inclusion of the cap structure in the OPS, via the modification process, prevents antibodies to the tip epitope of the OPS being formed. Therefore, only antibodies against the liner epitopes are generated; the greater length of the hexasaccharide antigen allows more of these antibodies to bind, whereas the shorter length of the trisaccharide does not. These results support the conclusion that much of the sensitivity of the exclusively 1,2 linked trisaccharide antigen is dependent upon the detection of anti-tip epitope antibodies generated during infection. These differences make the exclusively 1,2 linked trisaccharide (Structure XII) an effective DIVA diagnostic antigen.

Figure 6:
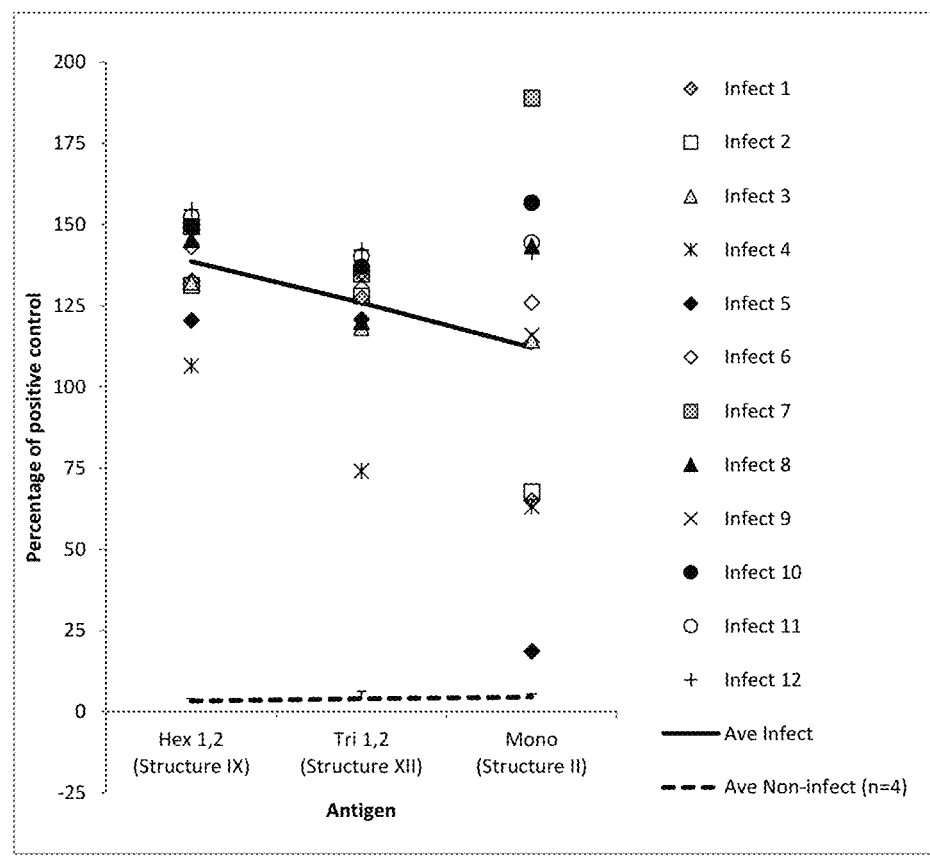
FIG. 6 shows the average (solid line) and individual (markers) iELISA results (y-axis) for 12 sera from 12 cattle naturally infected with *B. abortus* and the average (dashed line) ELISA results for 4 sera from 4 non-infected cattle, from three different ELISAs (x-axis), one with the exclusively 1,2 linked hexasaccharide (Hex 1,2=Structure IX), one with the exclusively 1,2 linked trisaccharide (Tri 1,2=Structure XII) and one with the monosaccharide (Mono=Structure II)
Figure 7:
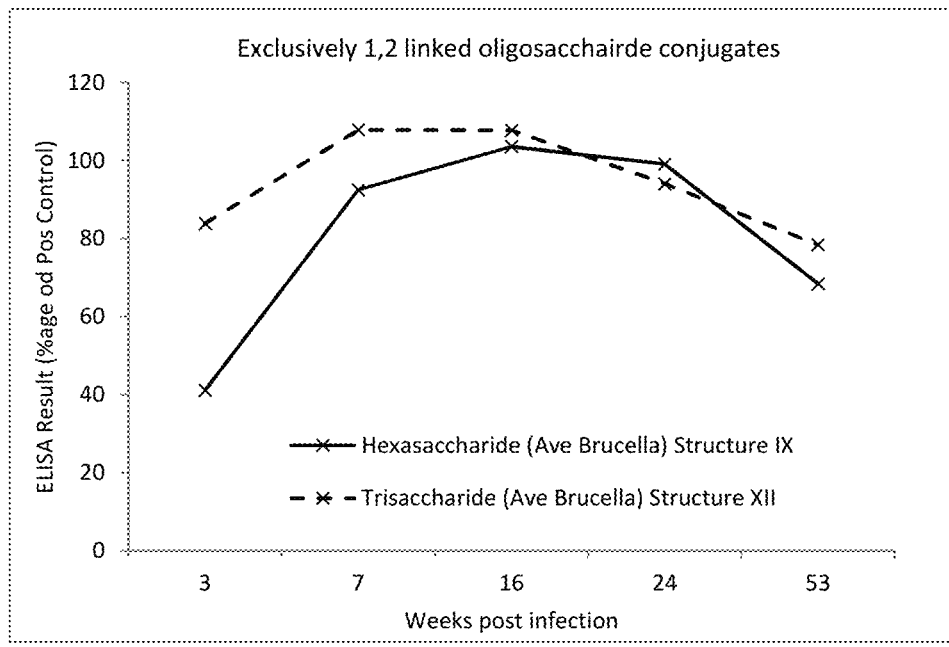
FIG. 7 shows the average iELISA result for serum samples from 4 animals experimentally infected with *B. abortus* strain 544 (A dominant) at each of the sampled time points (3, 7, 16, 24 and 53 weeks post-infection, x-axis), from two ELISAs, one with the exclusively 1,2 linked hexasaccharide (Structure IX) and one with the exclusively 1,2 linked trisaccharide (Structure XII)

For the same reasons, an exclusively 1,2 linked disaccharide (Structure XI) antigen is also an effective DIVA diagnostic. It is evident that it would not bind antibodies induced by a molecule comprising a cap structure, as described herein, for example Structures XXIII and XXIV. This is supported by the diagnostic data shown for the monosaccharide (Structure II) in FIG. 6 and Table 5 (DSn=90%, DSP=93.02%). This shows that even this small antigen has an unexpectedly high diagnostic sensitivity and specificity.

Figures 8, 9:
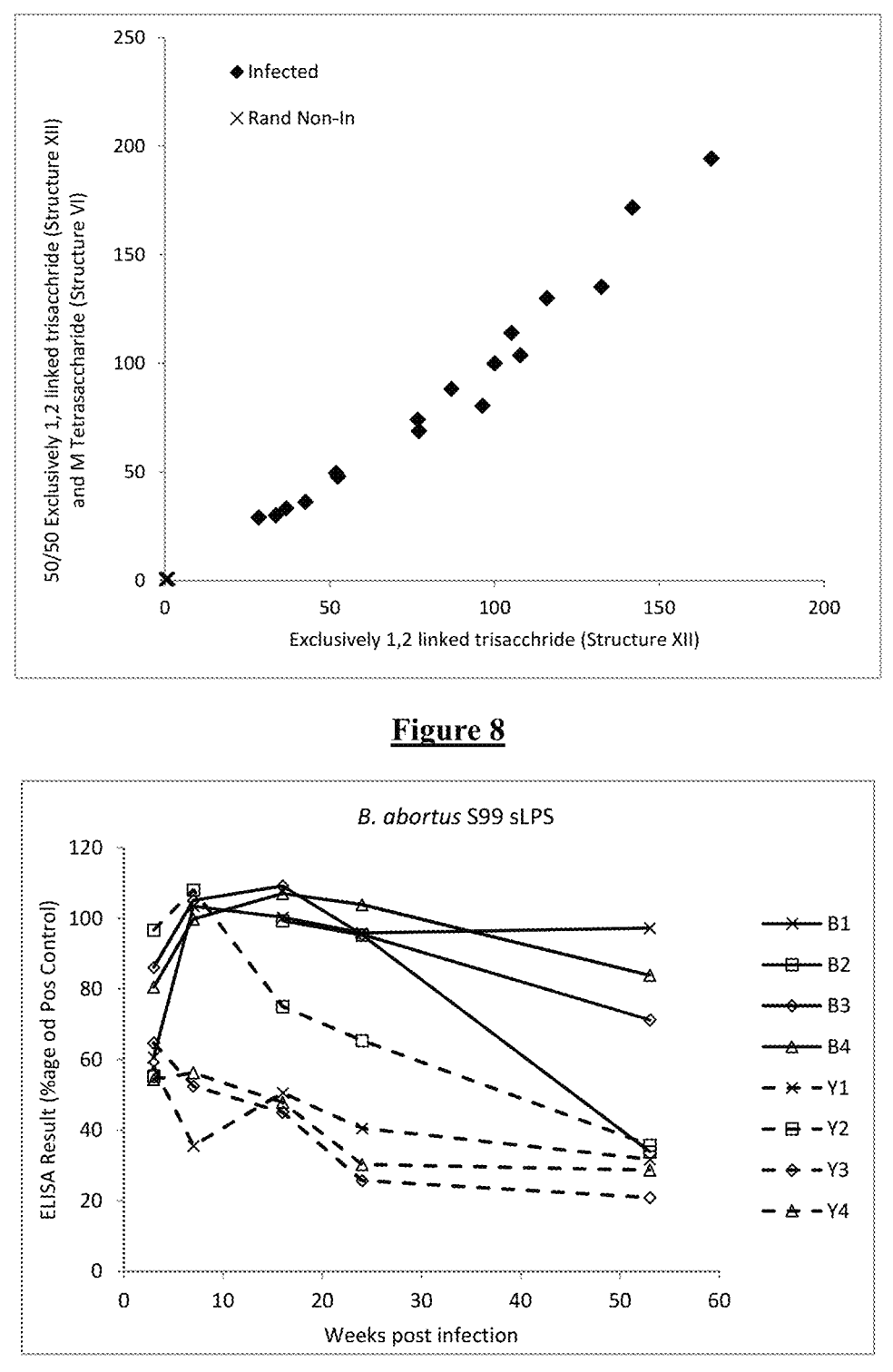

By way of further demonstration of its utility as a DIVA antigen, the exclusively 1,2 linked trisaccharide antigen (Structure XII) was used for the detection of anti-*Brucella* OPS antibodies in sera from 17 pigs infected with *B. suis* biovar 2 and in sera from 12 pigs that were not infected with *Brucella*. These samples were also tested with an equal mix (by mass of the conjugate diagnostic antigen) of the specific M-antigen tetrasaccharide (Structure VI) and the exclusively 1,2 linked trisaccharide conjugate (Structure XII). These results are presented by scatter plot in FIG. 8. This shows that the trisaccharide (Structure XII) detects all of the samples from the 17 infected pigs and shows no reaction to any of the samples from the 12 non-infected pigs. The mixed antigen preparation shows almost identical results. The biovar 2 OPS contains no 1,3 links (Zacchus et al. (2015) PLoS One 8, e53941), so antibodies raised against it would not be expect to bind so well to specific M-antigen oligosaccharides conjugates such as the tetrasaccharide (Structure VI) and disaccharide (Structure III). However, these antibodies do bind well to the exclusively 1,2 linked trisaccharide (Structure XII); this is the case when it is used on its own or when in combination with the tetrasaccharide (Structure VI). These results demonstrate that the DIVA vaccine and diagnostics concept described herein can also be applied against infection with *B. suis*, including infection with *B. suis* biovar 2.

From this, is can be seen that vaccination with an OPS conjugated to the carrier protein via the non-reducing terminal end raises antibodies capable of binding to the bacterial sLPS antigens, to whole *Brucella* cells, to an exclusively α1,2 hexasaccharide antigen (Structure IX) and also to a universal antigen (for example as described in WO2014/170681; Structure VIII). However, no binding is observed to the shorter antigens (Structures III, IV, V, VI and XII).

Comparing the results of this Example with the results of Example 4, for a DIVA vaccine to be provided the inventors concluded that a longer polymer of at least seven 4,6-dideoxy-4-formamido-α-D-mannopyranose units is required. The antibodies raised against such a polysaccharide, lacking the terminal tip epitope (disrupted as a result of conjugation to vaccine carrier protein through the non-reducing end of the polymer), are not detected by the short antigenic structures having Structures III, IV, V, VI and XII, so that these structures may be used as DIVA agents to distinguish between an animal which has been vaccinated using the modified polysaccharide and an animal which has been infected with *Brucella*.

Methods Used for Example 5

Preparation of Oxidised and TT-Conjugated OPS:
*Brucella* OPS was purified by hot-phenol extraction (Westphal et al (1952) Z. Naturforsch. 7:148-155) followed by mild acid hydrolysis and size exclusion chromatography (Meikle et al (1989) Infect Immun 57:2820-2828). The OPS for TT conjugation was oxidised at 2 mg/ml conc in 10 mM sodium metaperiodate (SMP) and 50 mM sodium acetate buffer (pH 5.5) for 1 hr in the dark. This was sufficient to oxidise the vicinal diol hydroxyl groups on the $2^{nd}$ and $3^{rd}$ carbons of the terminal sugar. Residual SMP was removed by desalting using a PD-10 column (Sephadex-G25 column) according to the manufacturer's instructions (GE Healthcare). A suitable volume of elution buffer allowed the OPS to flow through.

Oxidised OPS was then subjected to reductive amination. Oxidised OPS was incubated in PBS at final concentrations of 5 mg/ml OPS and 0.5 M ammonium chloride and 0.1 M sodium cyanoborohydride at 37° C. for 24 hours, before desalting into water with a Sephadex G-25 column and then freeze drying.

OPS was then incubated at 5 mg/ml with 5 mg/ml DSG in PBS for 45 mins on a rotary shaker before desalting with a Zeba 40 kDa column into fresh PBS. The OPS-DSG samples were then incubated with tetanus toxoid (TT) at final concentrations of approximately 2.5 and 0.5 mg/ml respectively. This was done for 2 hours at room temperature (in the dark) on a rotary shaker. Glycine was then added at a final concentration of 2 mg/ml and incubated for a further 15 mins. The samples were then subjected to fractionation by SEC-HPLC to separate the glycoconjugate from the unincorporated OPS. Binding of the glycoconjugates to anti-*Brucella* antibodies was confirmed by SDS-PAGE silver stain and Western blot.

Animals and immunisation: Three groups of 8 female CD1 mice were used, aged 7 weeks at the time of pre-bleed. A pre-bleed (100 µl) was taken from each mouse (from the tail vein) to prepare serum from which a baseline antibody titre against the native and proposed DIVA antigens was established. Antibody titre was evaluated by indirect ELISA assays.

Two days later the mice were immunised with 5 µg of the designated glycoconjugate antigen, suspended in physiological PBS without adjuvant. The dose was administered subcutaneously in a 100 µl volume. At 19 days post immunisation, a 100 µl blood sample were taken from each mouse via the tail vein. After another 2 days (21 days from the $1^{st}$ immunisation) the mice were immunised a $2^{nd}$ time with the same antigen, formulation, dose, volume and via the same route as for the $1^{st}$ immunisation. After 33 days from the $1^{st}$ immunisation, a 100 µl blood sample was taken from the mice via the tail vein. After another 2 days (35 days from the $1^{st}$ immunisation) the mice were immunised for the $3^{rd}$ time with the same antigen, formulation, dose, volume and via the same route as for the 1st immunisation. Two weeks after this (49 days from the first immunisation), the mice were euthanised, then dissected in order to extract blood from the chest cavity after cutting the aorta.

Immunoassays: The smooth LPS antigens *B. abortus* S99 and *B. melitensis* 16M were diluted 0.6 µg/ml and TT was diluted 2.5 µg/ml in carbonate buffer (Sigma). The whole cell antigens *B. abortus* S99, *B. melitensis* 16M and *B. suis* biovar 2 (Thomsen) were diluted 15.6 µg/ml in carbonate buffer (Sigma). Synthetic antigens (Structures III, VI, VII, VIII) were diluted 2.5 µg/ml in carbonate buffer (Sigma).

100 µl per well of each antigen was added to Standard bind ELISA plates (Nunc). The plates were incubated overnight at 4-8° C. then washed four times with PBS-Tween, 200 µl per well and tapped dry on blotting paper.

Mouse sera were diluted in log dilutions at 1/100, 1/316.22, 1/1000, 1/3162.27, 1/10000, 1/31622.7, 1/100000, 1/316227, 1/1000000 and 1/3162270 in casein buffer and 100 µl per well was added to the antigen coated plates. Monoclonal antibody BM40 was diluted 5 µg/ml in casein buffer (Sigma) and added to the plates, 100 µl per well, as a control. A positive serum control, mouse sera from a mouse immunised with Hexasaccharide Structure I, and a negative serum control from a normal (non-immunised) mouse were also included, 100 µl per well, as controls.

The plates were incubated for 30 minutes at room temperature, on a rotator at 120 rpm, then washed four times with PBS-Tween, 200 µl per well and tapped dry on blotting paper. Anti-mouse immunoglobulins:HRP (Dako) was diluted 1 in 1000 in casein buffer (Sigma) and 100 µl/well was added to the plates. The plates were incubated for 60 minutes for the synthetic antigens and 30 minutes for sLPS and whole cell antigens at room temperature, on a rotator at 120 rpm, then washed four times with PBS-Tween, 200 µl per well and tapped dry on blotting paper. Substrate buffer (pH4.0) (Fluka) with 2,2'-Azino-bis(3-ethylbenzothiazoline-6-sulfonic acid) diammonium salt (ABTS) (Sigma) and 3% hydrogen peroxide (Sigma) was added to the plates, 100 µl per well, and incubated at room temperature for 20 minutes. The reaction was slowed with 0.1M sodium azide, 100 µl per well, and the plates were read at 405 nm absorbance. Data was calculated as the blanked mean of duplicate wells as a percentage of the BM40 control wells tested with Disaccharide Structure III, as this was added to every test plate.

The optical densities (ODs) for each sample and dilution were blanked by subtracting the OD for control wells to which no sera had been added but were otherwise processed as described above. The quantitative data for the samples were then normalised by expressing the ODs as a percentage of the positive control. The end titres were calculated (using GraphPad Prism 6) as the dilution at which the signal (expressed as a percentage of the positive control) was equal to the positive/negative threshold. This threshold was calculated as the mean of the pre-bleed samples plus 1.96 times the standard deviation of the pre-bleed samples.

iELISAs on cattle and pig sera: To perform ELISA the oligosaccharide BSA conjugates (Structures II, VI, IX, XII) were immobilised onto the surface of standard polystyrene ELISA plates passively via overnight incubation in carbonate buffer at 4° C. at 2.5 µg/ml (1.25 µg each for mixed antigen coating), 100 µl/well. The plates were washed 4 times with 200 µl/well PBST (PBS containing 0.05% (v/v) Tween 20), tapped dry. Sera was diluted 1/50 in buffer (in duplicate) and 100 µl added per well. The plates were incubated for 30 mins at room temperature at 160 rpm, after which time they were washed and tapped dry as described above. For bovine sera, an HRP-conjugated mouse anti-bovine IgG1 conjugate was used. For porcine sera an HRP-conjugated recombinant protein A/G was used. The conjugates were diluted to working strength in buffer and the plates incubated, washed and tapped dry as for the serum incubation stage. The plates were then developed with ABTS (2,2'-Azino-bis(3-ethylbenzothiazoline-6-sulfonic acid) diammonium salt) and hydrogen peroxide substrate for 10-15 mins, stopped with 0.4 mM sodium azide and read at 405 nm wavelength. The optical density for the duplicates was averaged and the blank OD (buffer only instead of sera) was subtracted. This value was then expressed as a percentage of a common positive control serum sample from a *B. abortus* infected cow (for testing of cattle sera) or a positive control serum sample from a *B. suis* infected pig (for testing of porcine samples). In each case a negative control sample was always run in order to ensure the quality of the data.

The same ELISA method was used for testing using sLPS antigen. The sLPS was diluted to working strength and passive coated to standard polystyrene ELISA plates as described for the oligosaccharide conjugates. The rest of the procedure was conducted as described for the oligosaccharide conjugates.

Several populations of field sera were evaluated by iELISA using the antigens described above. The specific numbers of samples are described above. All samples classified as infected were from animals that had been confirmed as infected by bacteriological culture of *B. abortus* (cattle) or *B. suis* (pigs) from tissues derived from the animals themselves (most cattle samples and all swine samples) or the animals were serologically positive for brucellosis (using conventional serology) and were members of a herd that had been confirmed by bacteriological culture of *B. abortus* to be infected. The randomly collected samples from non-*Brucella* infected animals (cattle and pigs) have been collected from within Great Britain from 2007 onwards.

The oligosaccharide BSA conjugates (Structures II, VI, IX and XII), *B. abortus* sLPS and modified (i.e., capped) *B. abortus* OPS ELISAs were assessed against a panel of serum from cattle experimentally infected with either *B. abortus* or *Y. enterocolitica* O:9. Two groups of four Holstein/Fresian cross cattle were infected independently with either *B. abortus* strain 544 (109 colony forming units) via the ocular route, or *Y. enterocolitica* O:9 (1012 colony forming units) orally on 4 occasions on alternate days. The two animal groups were then kept apart to prevent cross infection. All cattle were confirmed free of both *Yersinia* and *Brucella* prior to experimental infection and microbiological investigations confirmed that subsequent infection had taken place. Serum from each animal was tested by at 3, 7, 16, 24, and 53 weeks post infection. All animal procedures were conducted in accordance with the United Kingdom Animal (Scientific Procedures) Act 1986.

Example 6: Use of Capped OPS as a Diagnostic Antigen

A study was carried out in cattle to evaluate the potential of novel OPS based antigens to differentiate between antibodies induced by field strains of *B. abortus* or *B. abortus* S19 vaccine.

Two OPS based antigens were evaluated using standard iELISA methods. These were a standard preparation of smooth lipopolysaccharide (sLPS) from *B. abortus* S99 and purified OPS derived from *B. abortus* S99 which had been modified and conjugated to a carrier to assist attachment to the ELISA plate surface (cOPS). This modification and conjugation capped the OPS, i.e., disrupted the terminal epitope.

These antigens were evaluated against the following serum panel (there was no multiple sampling of animals: 20 samples taken 45 days after vaccination, 60 samples taken from herds confirmed by culture as infected with a field strains of *B. abortus*. Results are presented in FIG. 5. In addition, 7 negative and 7 positive controls were applied.

Vaccination was performed via the conjunctival route using a dose of 5-10×10$^9$ CFUs of *B. abortus* S19.

The sLPS antigen was the most effective at differentiating between the samples from the infected and non-infected animals. As might be expected, it was also the most susceptible to reaction with sera from vaccinated animals. The cOPS antigen also detected sera from the infected herds. The principle finding was that the cOPS antigen was less sensitive in detecting vaccine-induced antibodies whilst retaining sensitivity against field-induced antibodies due to true infection. This is demonstrated by the AUC values (for differentiation between the sera from infected herds and vaccinated animals) which were 0.8817 for the cOPS antigen and 0.6800 for the sLPS antigen. There was a highly significant difference between these two AUC values (P<0.01). This study indicates that the capped OPS antigen is a superior serological tool in areas where vaccination with *B. abortus* S19 is taking place.

Methods Used for Example 6

Preparation of antigens: *Brucella* sLPS, derived from *B. abortus* S99, was purified by hot-phenol extraction (Westphal et al (1952) Uber die Extraction von Bakterien mit Phenol/Wasser.Z.Naturforsch.7:148-155). The OPS was derived from this by mild acid hydrolysis and size exclusion chromatography (Meikle et al (1989) Infect Immun 57:2820-2828). The OPS was oxidised at 2 mg/ml conc in 10 mM sodium metaperiodate (SMP) and 50 mM sodium acetate buffer (pH 5.5) for 1 hr in the dark. This was sufficient to oxidise the vicinal diol hydroxyl groups on the 2$^{nd}$ and 3$^{rd}$ carbons of the terminal sugar. Residual SMP was removed by desalting using a PD-10 column (Sephadex-G25 column) according to the manufacturer's instructions (GE Healthcare). A suitable volume of elution buffer allowed the OPS to flow through.

Oxidised OPS was then subjected to reductive amination. Oxidised OPS was incubated in PBS at final concentrations of 5 mg/ml OPS and 0.5 M ammonium chloride and 0.1 M sodium cyanoborohydride at 37° C. for 24 hours, before desalting into water with a Sephadex G-25 column and then freeze drying. OPS was then activated by incubation at 5 mg/ml with 5 mg/ml DSG in PBS for 45 mins on a rotary shaker before desalting with a Zeba 40 kDa MWCO column into fresh PBS. Palmitic acid hydrazide (PAH) was dissolved to 10 mg/ml in DMSO and 1 part of this was added to 9 parts of OPS in PBS for a final dilution of 4.5 mg/ml OPS and 1 mg/ml PAH. The samples reacted for 2 hours at room temperature on a rotary shaker before excess PAH was removed by desalting into H$_2$O with a Zeba 40 kDa MWCO column. The PAH conjugated OPS was then freeze dried.

Immunoassays: The sLPS and cOPS were diluted to 0.5 and 5 µg/ml respectively in carbonate buffer (pH 10). 100 µl per well of each antigen was added to standard bind ELISA plates. The plates were incubated overnight at 4-8° C. then washed 5 times with wash solution (0.0014% w/v di-sodium hydrogen orthophosphate and 0.1% Tween-20 in H$_2$O) and tapped dry.

Cattle sera was diluted 1/50 in PBS containing 0.1% Tween-20 and 100 µl per well was added to the antigen coated plates. The plates were incubated for 1 hour at room temperature on a rotary shaker and then washed and tapped dry as described above. Protein A/G-HRP conjugate was diluted to 0.05 µg/ml in PBS containing 0.1% Tween 20 and 100 µl of this was added to every well. The plates were then incubated, washed and dried as above for the serum incubation. Substrate buffer was citric acid dibasic sodium phosphate at pH 5.5. One 10 mg tablet of OPD (o-phenylenediamine dihydrochloride) and 100 µl of 3% H$_2$O$_2$ was added per 25 mls of substrate buffer and 100 µl of this was added per well. Plates are developed for between 15-30 minutes and then optical densities (ODs) are read at 450 nm. The ODs for samples and controls are blanked by subtraction of the OD of a well to which buffer only was added (no sera). The blanked OD for each sample is expressed as a percentage of the blanked OD of a common positive control.

Vaccination studies: The protective efficacy of the vaccine formulation is tested in accordance with the OIE (World Organisation for Animal Health) requirements for the immunogenicity testing of *B. abortus* S19 and *B. melitensis* Rev1 vaccines (as described in the 2009 chapters on Bovine Brucellosis (chapter 2.4.3) and Caprine and Ovine Brucellosis (chapter 2.7.2) within the OIE Manual of Diagnostic Tests and Vaccines for Terrestrial Animals. The mice are immunised as described previously for Example 5, except that on day 49 they are challenged with a 100 µl dose, delivered intraperitoneally, containing 2×10$^5$ CFU of *B. abortus* strain 544 (or *B. melitensis* strain 16M). Mice are killed 15 days later.

Reference lots of vaccines *B. abortus* S19 and *B. melitensis* Rev1 and a negative (PBS only) control are evaluated at the same time to demonstrate that the procedure has been conducted correctly and to provide reference points against which the protective efficacy of the novel vaccine will be assessed. The procedure for quantification of protective efficacy, by deriving the spleen weights and bacterial load, is described below.

Each spleen is excised aseptically, the fat is removed, and the spleen is weighed and homogenised. Alternatively, the spleens can be frozen and kept at −20° C. for from 24 hours to 7 weeks. Each spleen is homogenised aseptically with a glass grinder (or in adequate sterile bags in stomacher) in nine times its weight of PBS, pH 6.8 and three serial tenfold dilutions (1/10, 1/100 and 1/1000) of each homogenate made in the same diluent. 0.2 ml of each dilution is spread in quadruplicate in agar plates; two of the plates are incubated in a 10% CO$_2$ atmosphere (allows the growth of both vaccine and challenge strains) and the other two plates are incubated in air (inhibits the growth of the *B. abortus* 544 CO$_2$-dependent challenge strain), both at 37° C. for 5 days.

Colonies of *Brucella* are enumerated on the dilutions corresponding to plates showing fewer than 300 CPU. When no colony is seen in the plates corresponding to the 1/10 dilution, the spleen is considered to be infected with five bacteria. These numbers of *Brucella* per spleen are first recorded as X and expressed as Y, after the following transformation: Y=log (X/log X). Mean and standard deviation, which are the response of each group of six mice, are then calculated.

The conditions of the control experiment are satisfactory when: i) the response of unvaccinated mice (mean of Y) is at least of 4.5; ii) the response of mice vaccinated with the reference S19 vaccine is lower than 2.5; and iii) the standard deviation calculated on each lot of six mice is lower than 0.8.

Example 7: Intact Whole Cell Diagnostic Antigen (Rose Bengal Test) Comprising a Cap Structure The process of eliminating the tip of the OPS can be performed when the OPS is also attached to other molecules. Through these attachments, the OPS may form a part of a larger entity including the whole bacterial cell from which it naturally extends.

The terminal perosamine in an OPS chain can be degraded by mild oxidation, thereby creating a cap structure at the distal end of the OPS chain, as described herein. This reaction, if maintained at the appropriate conditions, is very specific for the chemical groups that exist as part of the terminal perosamine of the OPS. Therefore, it is feasible that the degradation (capping) can be carried out on the OPS where this exists within a more complex combination of molecules and components without any significant or deleterious upon the non-OPS components. In consequence, it is possible to derive the diagnostic benefits from a capped OPS, as described in Example 6 above, even when the OPS is in an impure state.

Figure 16:
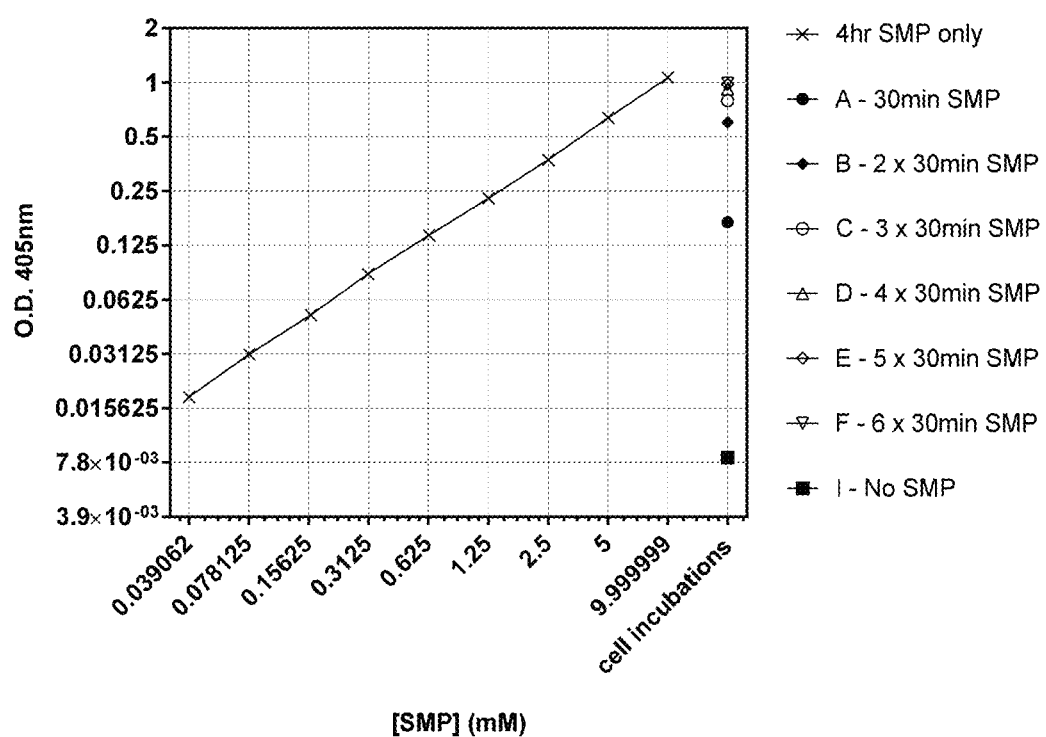
FIG. 16 shows the results of oxidation reagent (sodium metaperiodate [SMP]) consumption when applied to RBT antigen; the figure shows a standard curve of known SMP concentration (x-axis) against optical density (OD) at 405 nm (y-axis), with individual data points shown as black crosses and OD values of the oxidation reagents extracted at different points from the onset of the oxidation process shown on the right hand side of the x-axis ('cell incubations').

This approach was evaluated using the diagnostic whole cell agglutination assay known as the Rose Bengal test (RBT). This test is commonly used as a screening assay for the serodiagnosis of brucellosis and is described as suitable for this purpose by the OIE (World Organisation for Animal Health). The diagnostic antigen consists of intact whole cells of *B. abortus* (stains S99 or S1119-3, both biovar 1 and A-dominant) that have been stained pink with rose bengal stain and then suspended in a pH 3.65 buffer (±0.05). This stain greatly assists the visualisation of the agglutination that occurs when the antigen is mixed with test sera that contains anti-*Brucella* antibodies. As with all the conventional diagnostic tests used for serodiagnosis of brucellosis caused by smooth *Brucella* strains (those from the species *B. abortus, B. melitensis* and *B. suis*), the principle diagnostic molecule within the antigen is the OPS, as this is the molecule against which most of the antibodies induced during infection are raised (Ducrotoy et al. (2016) Veterinary Immunology and Immunopathology 171:81-102).

To cap (i.e., de-tip) the OPS within the RBT antigen, which exists on the surface of the cells, the antigen was separated from the assay buffer by centrifugation and suspended in cold (4° C.) oxidation reagents (10 mM sodium metaperiodate in 0.1 M sodium acetate buffer pH 5.5). The cells were incubated in with these reagents in the dark at 4° C. until the mild oxidation reaction had been completed. This was verified by measuring the consumption of sodium metaperiodate over time and reaching a stage where replenishment of sodium metaperiodate back to 10 mM resulted in no further consumption. At this stage, it was considered that all the OPS on the surface of the cells had been capped (i.e., de-tipped). The cells were centrifuged to separate them from the oxidation buffer and resuspended in test buffer for serological evaluation.

The analytical sensitivity of the oxidised (capped) and non-oxidised (non-capped) antigens was compared using a dilution series (in negative bovine serum) of a known positive bovine sample from a *B. abortus* infected animal: neat, ½, ¼, ⅛, 1/16, 1/32, 1/64 and 1/128. The negative serum used for dilution was also tested. The results showed that the two antigens (before and after oxidation) performed the same, agglutination was observed down to a 1/64 dilution. The 1/128 dilution of the positive serum and the neat negative serum were negative with both antigens.

To evaluate the diagnostic sensitivity, the oxidised (capped) and non-oxidised (non-capped) antigens were applied to 17 sera from non-*Brucella* infected cattle and 17 sera from *B. abortus* infected cattle. The results showed that all samples from the *Brucella* infected cattle agglutinated with both antigens and all samples from the non-infected cattle did not agglutinate with either antigen. The positive and negative controls used in this evaluation also gave the correct results for both antigens.

This study shows that relatively crude antigens that contain OPS can be oxidised to completion under mild conditions and remain effective serodiagnostic antigens. It has already been shown that this reaction provides a cap structure to the OPS. In the findings from this study, the ability of the oxidised antigen to differentiate between samples from *Brucella* infected and non-infected animals was unchanged. This is in accordance with data presented in Example 6 where the diagnostic attributes of the oxidised (capped/detipped) OPS against these sample types was excellent. In this example, the capped OPS showed a reduced sensitivity to samples from animals vaccinated with *B. abortus* S19. The oxidised (i.e., capped) RBT antigen also exhibits this property and will, therefore, be superior than the non-oxidised antigen at differentiating between sera from animals infected with smooth *Brucella* strains and those vaccinated with smooth *Brucella* vaccines (such as *B. abortus* S19 and *B. melitensis* Rev1).

This method of capping (detipping) the OPS can also be applied to other *Brucella* OPS containing diagnostic antigens such as the sLPS used for ELISA (where the OPS is attached to core sugars which are in turn attached to the Lipid A), other antigens (whole cells, cell lysates or fractions) used in agglutination assays (such as the Serum Agglutination Assay, the Buffered Plate Agglutination Test, and the Complement Fixation Test).

Methods Used for Example 7

The RBT is performed was performed as described in the OIE manual (OIE 2016 Brucellosis Chapter 2.1.4. Manual of Diagnostic Tests and Vaccines for Terrestrial Animals. OIE, Paris). The test (and control) sera is added to the side of RBT test antigen, 30 μl of each, upon a smooth white surface. The two are then mixed together to produce an oval or circle approximately 2 cm in diameter. This mix is gently rocked at room temperature (18-26° C.) for 4 minutes. After this time the mix is observed and any visible agglutination is considered positive. All the samples that were tested, as described above, were done so using this method. Positive and negative control sera were run with every test.

To oxidise the RBT antigen a volume of working strength antigen was centrifuged at 3000 g in order to pellet the cells. The supernatant, the test buffer, was removed and the cells resuspended in an equal volume, as was removed, of cold (+4° C.) oxidation reagent (10 mM sodium metaperiodate in 0.1 M sodium acetate buffer pH 5.5). The cells were incubated for 30 mins in the dark and then centrifuged as before. The supernatant was removed and replaced with fresh oxidation reagent. This process was repeated four more times so the antigen has undergone 6 times 30 mins of oxidation in total with replenishment of oxidation reagent each hour. After the fifth hour the cells were centrifuged as describe above, the supernatant removed and replaced with the original volume of fresh test buffer. The replenishment process allowed the reaction to progress without limitation due to consumption of sodium metaperiodate and without deviating from the mild oxidation conditions that facilitate the specific reaction with the vicinal cis diols on the terminal perosamine of the OPS.

The sodium metaperiodate content within the extracted supernatant was measured by dispensing 100 μl of the oxidation reagent into separate wells of a 96 well ELISA plate. Then 100 μl of a 0.5 mg/ml concentration of ABTS (2,2-azinobis-3-ethylbenzthiazoline-6-sulfonic acid) in a pH 4.0 buffer was added to each test well. In the presence of sodium metaperiodate this drove a colour change that was proportional to the concentration of this oxidising agent. The colour change after 15 mins was measured using an ELISA plate reader set to measure optical density at 405 nm. The molarity of sodium metaperiodate in the test sample was calculated by reference to a standard curve which was established by using control wells containing a known concentration of sodium metaperiodate. The results of the oxidation reagent consumption are presented in FIG. 16, with "A" being an indication of the consumption after the first 30 minute period, "B" the indication of the consumption after two 30 minute periods, and so on. The Figure therefore shows a standard curve of known sodium metaperiodate concentration against optical density (O.D. at 405 nm) and the OD values of the oxidation reagents extracted at different points from the onset of the oxidation process (on the right hand side). As can be seen, after 30 mins most of the sodium metaperiodate has been consumed. The first replenishment (2×30 mins) is not as depleted but just over half of the sodium metaperiodate has been consumed. The second replenishment (3×30 mins) has more than half (approximately 7 mM) of the sodium metaperiodate remaining. The third replenishment (4×30 mins) has approximately 8 mM concentration of sodium metaperiodate remaining and the fourth (5×30 mins) and fifth (6×30 mins) replenishments have approximately 9 mM of sodium metaperiodate remaining.

It is clear from this data that sodium metaperiodate is being consumed and that consumption slows and then effectively stops when cells that have already been subjected to sodium metaperiodate are introduced. The graph in the figure shows that, after five rounds of oxidation, no more significant reagent consumption is taking place. It was concluded from this that the antigen had been completely oxidised, all molecules capable of being oxidised by this mild process had been. After this oxidation process, the cells were centrifuged as described above, the supernatant removed, and resuspended in test buffer. These cells were then evaluated for diagnostic efficacy by application to the test sera described above. The oxidised RBT antigen was run in parallel with the original RBT antigen that had not been oxidised.

Example 8: Use of Exclusively 1,2 Linked Trisaccharide (Structure XII) and Disaccharide Antigens (Structure XI) as Serodiagnostic Antigens for Brucellosis The properties of the exclusively 1,2 linked trisaccharide (Structure XII) and disaccharide antigens (Structure XI) as DIVA diagnostics has been described above in Example 5. The effectiveness of these antigens was shown by demonstration of their good diagnostic sensitivity for detection of *B. abortus* infection in cattle and *B. suis* (biovar 2) infection in pigs. The value of these antigens within the DIVA context is therefore well established.

A further study was carried out to assess the suitability and merits of these antigens for routine serology, in the presence or absence of vaccination. As the role of the tip epitope has been demonstrated, during the work described herein, to be an important aspect of the diagnostic sensitivity of these antigens, there was an expectation that the presence of an identical epitope on the OPS of *Y. enterocolitica* O:9 (an exclusively 1,2 linked 4,6-dideoxy-4-formamido-mannopyranosyl polymer) would lead to the generation of cross reactions and false positive results that could be excessive. This expectation was reinforced by the strong reactions exhibited against the exclusively 1,2 linked trisaccharide (Structure XII) antigen by the sera from pigs infected with *B. suis* biovar 2 (as the long repeating element of the OPS from this biovar is identical to that of *Y. enterocolitica* O:9).

Figure 10:
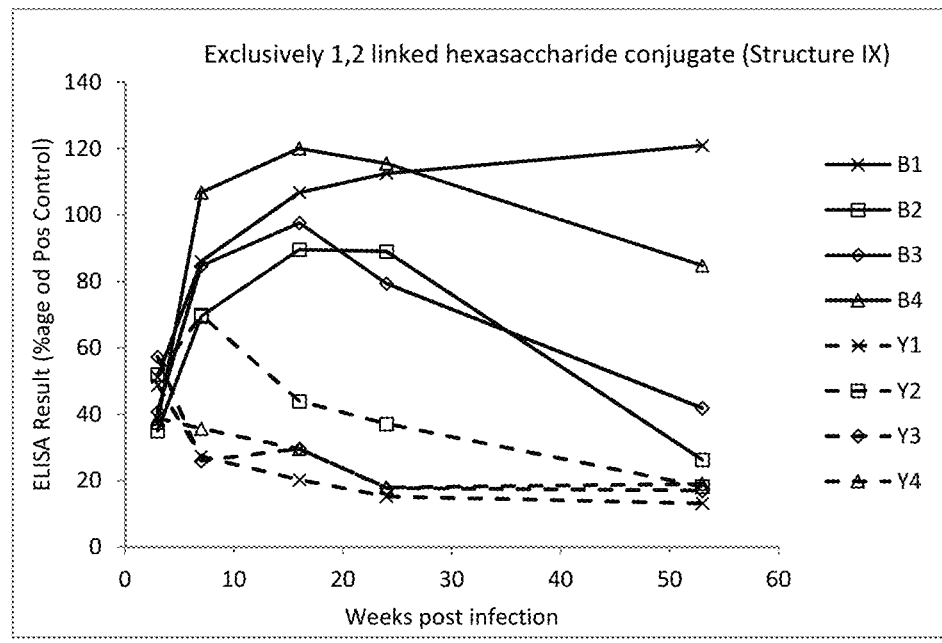
FIG. 10 shows iELISA results (y-axis), using exclusively 1,2 linked hexasaccharide (Structure IX) antigen, for 20 sera from 4 cows experimentally infected with *B. abortus* 544 (solid lines) that were each sampled at 3, 7, 16, 24 and 53 weeks post-infection (x-axis) and for 20 sera from 4 cows experimentally infected with *Y. enterocolitica* O:9 that were also sampled at 3, 7, 16, 24 and 53 weeks post-infection.
Figure 11:
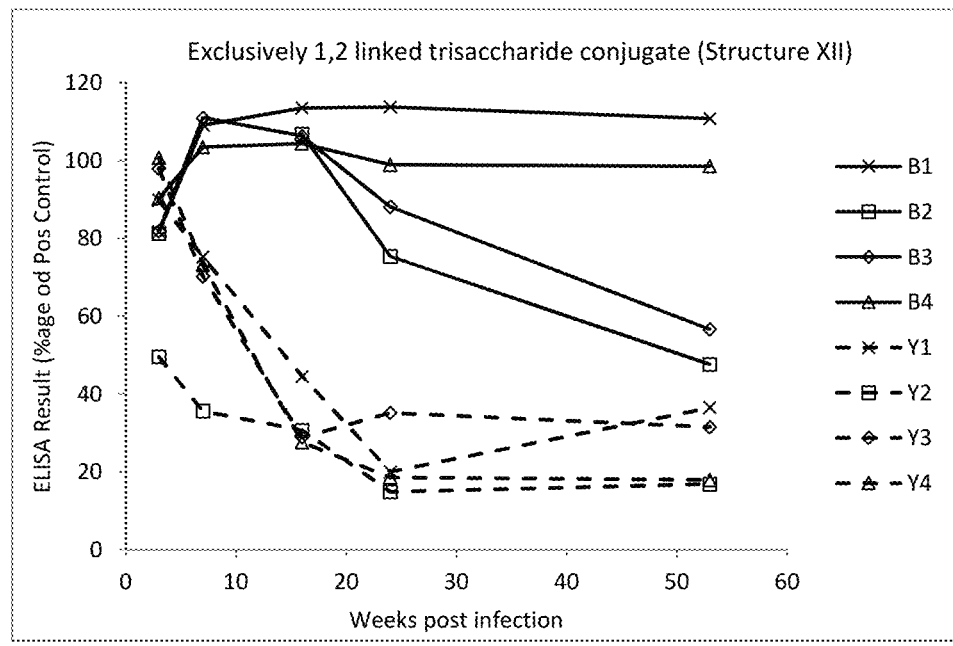
FIG. 11 shows iELISA results (y-axis), using exclusively 1,2 linked trisaccharide (Structure XII) antigen, for 20 sera from 4 cows experimentally infected with *B. abortus* 544 (solid lines) that were each sampled at 3, 7, 16, 24 and 53 weeks post-infection (x-axis) and for 20 sera from 4 cows experimentally infected with *Y. enterocolitica* O:9 that were also sampled at 3, 7, 16, 24 and 53 weeks post-infection.
Figures 12, 13:
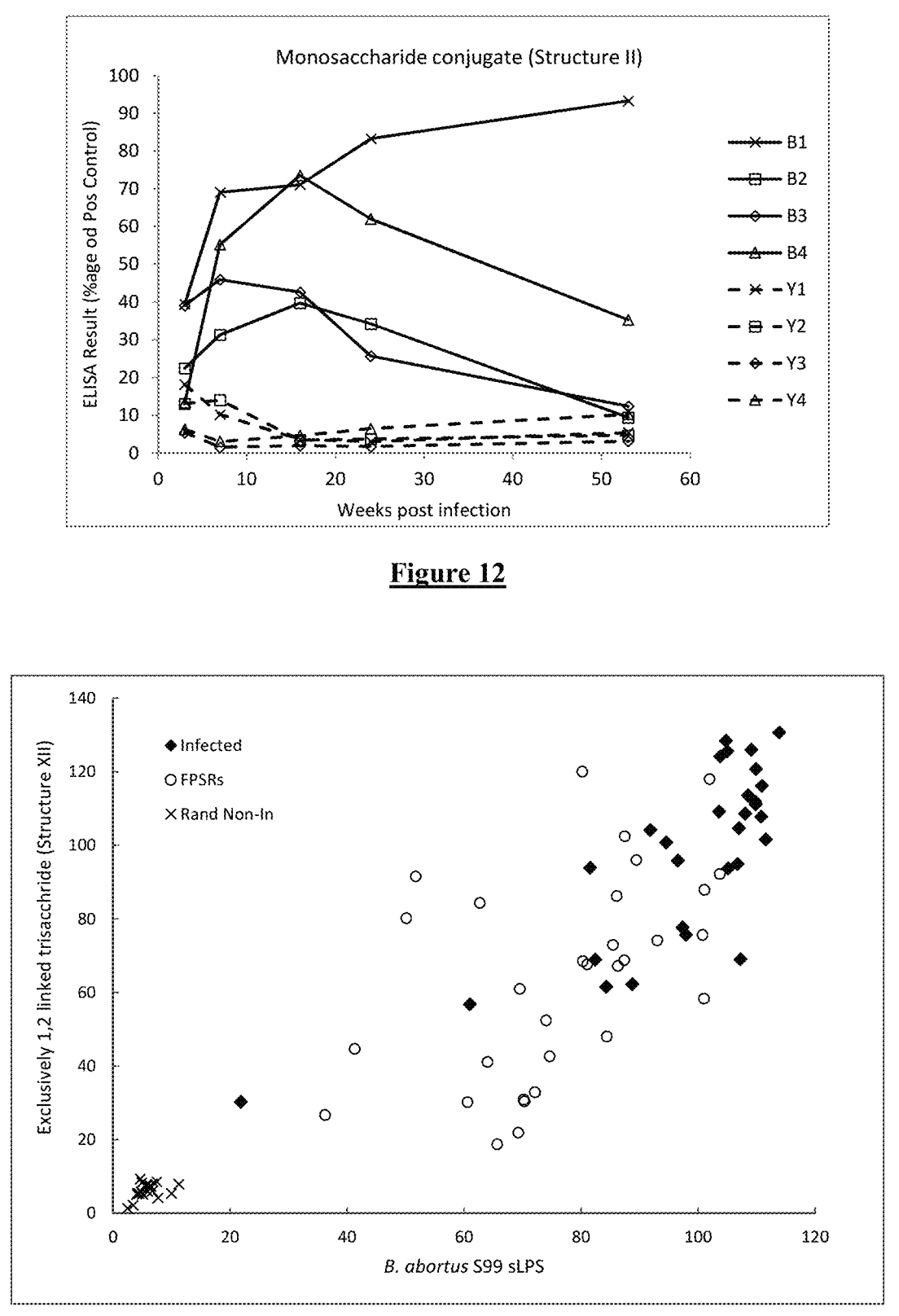
Figure 15:
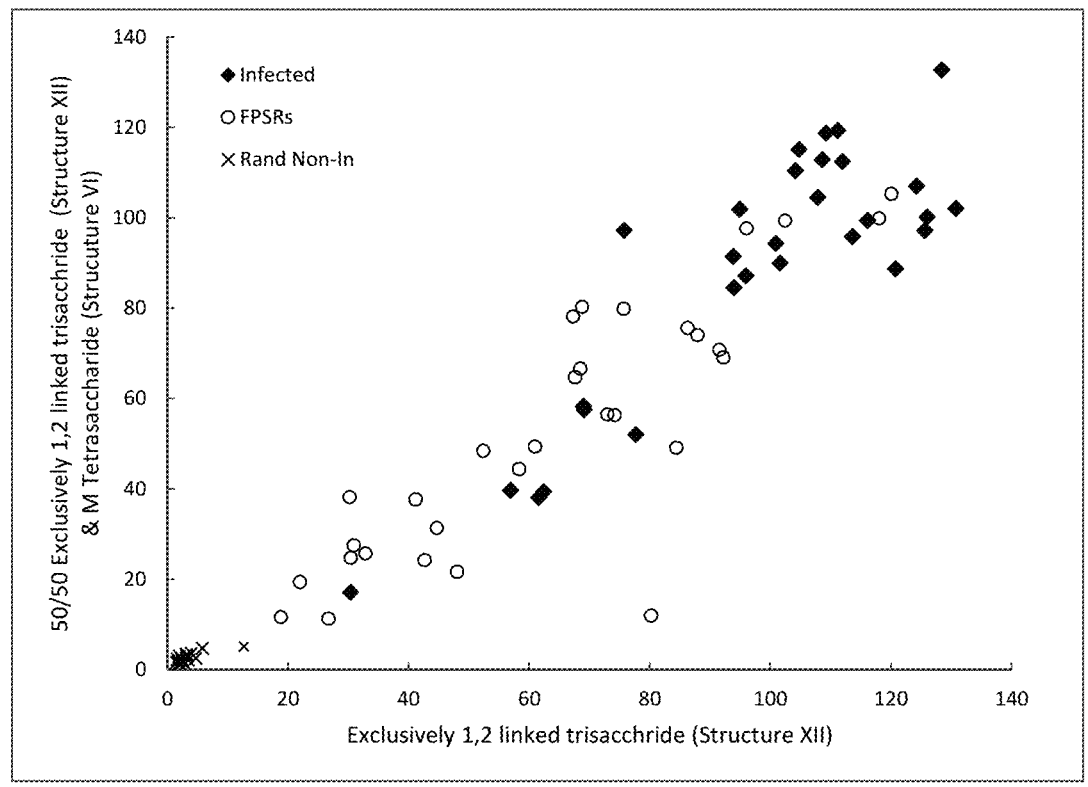
FIG. 15 is a scatter plot showing the iELISA results using the exclusively 1,2 linked trisaccharide BSA conjugate (Structure XII) (x-axis) against iELISA results using an even mix by mass (1.25 µg/ml coating concentration of each antigen, total concentration=2.5 µg/ml) of the exclusively 1,2 linked trisaccharide BSA conjugate (Structure XII) and the M tetrasaccharide BSA conjugate (Structure VI) (y-axis), with data points showing the results for 29 serum samples from 29 *B. abortus* infected cattle ('Infected', solid diamonds), 31 serum samples from 31 non-*Brucella* infected cattle that were false positive for conventional serodiagnostic assays for brucellosis ('FPSRs', open circles) and 20 serum samples from 20 randomly selected non-infected cattle ('Rand Non-In', crosses)

To evaluate the extent of this cross reaction the sera from four cattle experimentally infected with *Brucella abortus* strain 544 and four cattle experimentally infected with *Y. enterocolitica* O:9 (using samples taken on weeks 3, 7, 16, 24 and 53 post infection) were evaluated. To measure the reactions relative to other diagnostic antigens serological tests were performed using several different antigens and the results for these are presented as line graphs: *B. abortus* S99 sLPS (FIG. 9), exclusively 1,2 linked hexasaccharide (Structure IX) (FIG. 10), exclusively 1,2 linked trisaccharide (Structure XII) (FIG. 11) and monosaccharide (Structure II) (FIG. 12). Table 6 shows the number of samples from *Y. enterocolitica* O:9 infected cattle with serological results greater than the lowest serological result from the samples from the *B. abortus* 544 infected cattle. This provides a measure of the number of false positive results that occur within this sample set using the method of the invention, if the criteria for sensitivity is set at 100% (as all animals have been infected with *Brucella*). 100% assay sensitivity is desirable in a *Brucella* testing system, because failure to detect a *Brucella*-positive animal can be devastating.

TABLE 6

Number of samples from *Y. enterocolitica* O:9 infected cattle with serological results greater than the lowest serological result from the samples from the *B. abortus* 544 infected cattle.

| Antigen | Tip present/absent | No. of positive *Y. enterocolitica* O:9 samples |
|---|---|---|
| *B. abortus* S99 sLPS | Present | 15 |
| Exclusively 1,2 linked hexasaccharide BSA conjugate (Structure IX) | Present | 11 |
| Exclusively 1,2 linked trisaccharide BSA conjugate (Structure XII) | Present | 7 |
| Monosaccharide BSA conjugate (Structure II) | Present | 4 |

The results show that when the diagnostic antigens possess the tip epitope, the number of *Y. enterocolitica* O:9 positive samples decreases, and so the specificity increases, as the length of the antigen becomes smaller: sLPS>hexasaccharide>trisaccharide>monosaccharide. This occurs even though the terminal perosamine of the *B. abortus, B. melitensis, B. suis* and the *Y. enterocolticia* O:9 OPS is exactly the same. The shorter the (exclusively 1,2 linked) oligosaccharide, the greater the boost to specificity; this could not have been predicted.

A detailed evaluation of the serological results shows that although the results for the samples from the *Y. enterocolitica* O:9 infected animals are initially high against the exclusively 1,2 linked trisaccharide (Structure XII), they then fall rapidly for all four animals. By week 16 the results for all four animals remain lower than the lowest result for the *Brucella* infected animals. The results for the *Brucella* infected animals do not begin to fall significantly until after week 16, even then two animals remain high. The serological profiles obtained with the *B. abortus* S99 sLPS antigen (the antigen recommended by the OIE for *Brucella* iELISA) show the results from the *Y. enterocolitica* O:9 infected animals falling immediately in 3 out of 4 cases (but not as dramatically as is the case for the exclusively 1,2 linked trisaccharide) and with one sample, from *Brucella* infected animal number 2, becoming relatively low at week 53. The results for *Y. enterocolitica* O:9 infected animal number 2 increase to week 7 and stay high until week 24.

The results from the exclusively 1,2 linked hexsaccharide (Structure IX) antigen show attributes of both the trisaccharide (Structure XII) and S99 sLPS antigens as befitting its intermediate length. Although the results for the samples from the *Y. enterocolitica* O:9 infected animals fall relatively quickly the result for animal 2 increases from week 2 to 7. The results for the monosaccharide show a good distinction between the infection types although some of the results for the samples from the *Brucella* infected animals are quite low, which reflects the more limited sensitivity of this antigen.

The exclusively 1,2 linked trisaccharide (Structure XII), the *B. abortus* S99 sLPS and a mix (50/50 by mass) of the exclusively 1,2 linked trisaccharide (Structure XII) and the tetrasaccharide (Structure VI) antigens were tested against 29 serum samples from cattle field infected with *B. abortus*, 20 serum samples from randomly selected non-*Brucella* infected cattle, and 31 samples from cattle that are false positive to conventional *Brucella* serodiagnostic assays. The data is presented in 3 scatter plots: *B. abortus* S99 sLPS against exclusively 1,2 linked trisaccharide (Structure XII) (FIG. 13), *B. abortus* S99 sLPS against a 50/50 mix of exclusively 1,2 linked trisaccharide (Structure XII) and specific M-antigen tetrasaccharide (Structure VI) (FIG. 14), and the exclusively 1,2 linked trisaccharide (Structure XII) against the 50/50 mix of exclusively 1,2 linked trisaccharide (Structure XII) and specific M-antigen tetrasaccharide (Structure VI) (FIG. 15).

The scatter plots (FIGS. 13 to 15 show that all three antigen preparations fully distinguish between the samples from infected animals and those from randomly selected non-infected animals. However, in all cases there is considerable overlap with the samples from the FPSR population. The capability of the antigens to differentiate between the samples from the *Brucella* infected animals and those from the FPSR populations when the sensitivity is high is shown in Table 7. The need for a high sensitivity reflects both the sample populations and the testing requirement. The results show that at a 100% and 96.6% diagnostic sensitivity the exclusively 1,2 linked trisaccharide (Structure XII) and the 50/50 mix of exclusively 1,2 linked trisaccharide (Structure XII) and the M-antigen tetrasaccharide (Structure VI) both outperform the native *B. abortus* S99 sLPS (the current standard antigen as recommended by the OIE).

TABLE 7

Specificity against FPSR population when the test positive/negative cut-off is adapted to different antigen sensitivities (number of positive samples shown in brackets)

| Diagnostic Sensitivity | *B. abortus* S99 sLPS | Exclusively 1,2 linked trisaccharide | Mix |
|---|---|---|---|
| 100.0% | 0.0% (0) | 12.9% (4) | 9.7% (3) |
| 96.6% | 16.1% (5) | 38.7% (12) | 35.5% (11) |
| 93.1% | 58.1% (18) | 45.2% (14) | 38.7% (12) |

The results and conclusions from the field sera and from the experimentally infected sera are in agreement. At the highest levels of diagnostic sensitivity, the specificity obtained with the exclusively 1,2 linked trisaccharide (Structure XII) is superior to that obtained with the natural sLPS antigen (the current standard antigen). Lowering the sensitivity requirement leads to a superior performance from the sLPS although the sensitivity compromise is unfavourable. The data from the experimental infections suggests that the specificity of the different antigens depends upon how close to the point of infection with a cross-reacting organism, such as *Y. enterocolitica* O:9, the sample is taken.

Therefore, not only are the exclusively 1,2 linked trisaccharide (Structure XII), disaccharide (Structure XI), and the monosaccharide (Structure II) unexpectedly highly sensitive diagnostic sensitivity antigens for brucellosis but they also have unexpectedly high diagnostic specificity.

In the present example, serology was performed on samples taken from infected animals where the infective *Brucella* biovar is an A-dominant strain. Such infections would be expected to give rise to a greater proportion of antibodies that react to sequences of exclusively 1,2 linked perosamines (4,6-dideoxy-4-formamido-mannopyranosyl), rather than antibodies against sequences containing 1,3 linked perosamines. The ability of the exclusively 1,2 linked trisaccharide (Structure XII) and the specific M-antigen tetrasaccharide (Structure VI) antigens to detect anti-OPS antibodies induced by such infections has been shown above or previously (WO2014/170681). The antigens may be useful when used on their own their own or, as shown above, work well when used together.

When infections with M-dominant strains occur, then the antibodies induced would likely shift towards a higher proportion of antibodies against sequences of perosamines containing 1,3 linkages. Under such circumstances, the specific M-antigen tetrasaccharide (Structure VI) would be a more sensitive diagnostic. The use of the two antigens in combination (Structures XII or XI in combination with Structure VI, for example applied as a mix) gives optimal sensitivity under both scenarios, namely, infection with A-dominant or M-dominant strains of *B. abortus, B. melitensis* and *B. suis.*

In sum, the work described herein provides an antigen combination which is a universal antigen that is sensitive, DIVA-compatible, more specific than native antigens such as the OIE-recommended antigen *B. abortus* S99 sLPS, and is cheaper to produce and use than a longer synthetic "universal" antigen.

Methods Used for Example 8

The serological methods and the samples used are the same as described for Example 5 with the addition of the false positive serological reactor samples (FPSRs). These sera were collected from within Great Britain between 1996 and 1999, more than 10 years since the declaration of its officially brucellosis-free status. These sera were all positive for at least one of four conventional serodiagnostic assays for bovine brucellosis, CFT, SAT, cELISA, or iELISA, that are approved by the OIE. Other than serology, there was no cultural or epidemiological evidence of the disease.

APPENDIX: POLYSACCHARIDE SYNTHESIS METHODS

Synthesis of Heptasaccharide

The synthesis uses three key build blocks a known protected methyl glycoside S12. Two glycosyl donors 11 and 13 (below) are used to extend the 1,2 linked oligosaccharide, donor 11 and a capping residue 13 bearing a tether to conjugate to protein. Compound 11 allows the chain extension one residue at a time and the temporary acetate protecting group at O-2 allows for easy removal revealing the hydroxyl group for further chain extension. The preformed capping residue with attached tether 13 is prepared from the known methyl 2,3-O-isopropylidene-6-deoxy-α-D-mannopyranoside S5 and the protected tether 12 which is in turn prepared from commercially available benzyl (5-hydroxypentyl) carbamate in a two-step conversion to S13 and then 12 (Scheme 4S). A series of transformation allows for the reaction of S5 with 12 and then further reactions provide the thioglycoside 13.

The detailed construction of these intermediates proceeds as described below

Synthesis of thioglycoside donors 11

Methyl 4-azido-3-O-benzyl-4,6-dideoxy-a-D-mannopyranoside (S11)

Analytical data for the title compound was essentially the same as previously described (Bundle et al (1988) Carbohydr Res 174:239-251).

1,2-di-O-acetyl-4-azido-4,6-dideoxy-a-D-mannopyranose (S12)

A solution of S11 (5 g, 17.05 mmol) in acetic anhydride/acetic acid/sulfuric acid (50:20:0.5, 50 mL) was stirred at 21° C. for 3 h, and then poured into ice-cold 1M $K_2CO_3$ solution (80 mL). The mixture was then diluted with $CH_2Cl_2$ (~100 mL) and washed with water (2×30 mL), sat. aq. $NaHCO_3$ (35 mL), and brine (15 mL). The organic phase was separated, dried over $MgSO_4$, and concentrated in vacuo. The residue was purified by column chromatography on silica gel (ethyl acetate-hexane gradient elution) to afford the title compound S12 (5.6 g, 91%) as a sticky liquid. Analytical data for S12: Rf=0.35 (ethyl acetate/hexane, 1/4, v/v); $[\alpha]D^{21}$=+30.71 (c=1.51, $CHCl_3$); $^{13}C$ NMR (176 MHz, $CDCl_3$): δ: 169.8, 168.3, 136.9, 128.5, 128.3, 128.1, 91.0, 75.7, 71.8, 69.3, 66.3, 63.5, 20.8 (×2), 18.5 ppm; HRMS (ESI): m/z calcd for $C_{17}H_{21}N_3O_6Na$ [M+Na]+: 386.1323, found: 386.1322.

p-Tolyl 2-O-acetyl-4-azido-3-O-benzyl-4,6-dideoxy-1-thio-a-D-mannopyranoside (11)

To the stirred solution of S12 (0.78 g, 2.15 mmol) and p-toluenethiol (0.4 g, 3.22 mmol) in anhydrous $CH_2Cl_2$ (15 mL) at 0° C., $BF_3 \cdot Et_2O$ (0.32 mL, 2.57 mmol) was added drop wise. When TLC showed the reaction was completed, the mixture was then diluted with $CH_2Cl_2$ (~50 mL) and washed with water (2×10 mL), sat. aq. $NaHCO_3$ (15 mL), and brine (10 mL). The organic phase was separated, dried over $MgSO_4$, and concentrated in vacuo. The residue was purified by flash column chromatography (Ethyl acetate-hexane gradient elution) to give 11 as a sticky liquid (0.854 g, 92.9%). Analytical data for 11: Rf=0.7 (Ethyl acetate/hexane, 1/3, v/v); $[\alpha]D^{21}$=+135.5 (c=2.25, $CHCl_3$); $^{13}C$ NMR (176 MHz, $CDCl_3$): δ: 170.0, 138.1, 137.0, 132.4, 132.3, 129.9, 129.8, 129.6, 128.5, 128.5, 128.4, 128.1, 86.4, 76.4, 71.7, 69.1, 68.2, 64.2, 21.1, 21.0, 18.4 ppm; HRMS (ESI): m/z calcd for $C_{22}H_{25}N_3O_4SNa$ [M+Na]+: 450.1458, found: 450.1465.

Synthesis of Linker Bromoalkane 12

5-(N-benzyl((benzyloxy)carbonyl)amino)pentanol benzoate (S13)

Benzoyl chloride (0.88 mL, 7.59 mmol) was added dropwise to a stirred solution of benzyl (5-hydroxypentyl) carbamate (commercially available) (1.5 g, 6.32 mmol) in anhydrous $CH_2Cl_2$ (15 mL) containing $Et_3N$ (1.76 mL, 1.26 mmol) at 0° C. After 1 minute DMAP (1.7 g, 13.9 mmol) in anhydrous $CH_2Cl_2$ (10 mL) was added dropwise to the reaction mixture and stirred at rt overnight. The resulting mixture was diluted with $CH_2Cl_2$ (~30 mL) and washed with aq. HCl (1M, 1×10 mL), water (60 mL), sat. aq. $NaHCO_3$ (30 mL), and brine (30 mL). The organic phase was separated, dried over $MgSO_4$, and concentrated in vacuo. The residue was quickly filtered off on silica gel (ethyl acetate-hexane gradient elution) to afford the almost pure compound as oil. This crude material was directly used for benzylation.

To the solution of benzoyl protected compound (0.9 g, 2.63 mmol) dissolved in anhydrous DMF (10 mL) was added NaH (0.12 g, 2.89 mmol) at 0° C. The mixture was stirred at 0° C. for 45 min, and then BnBr (0.37 mL, 3.16 mmol) were added. After stirring for another 12 h when TLC showed that the reaction was completed, it was quenched with $H_2O$ at 0° C., and the mixture was diluted with EtOAc. The aqueous layer was extracted with EtOAc (5×25 mL), and the organic phases were combined and dried over $Na_2SO_4$. The desired product S13 (1.093 g, 96.1%) was obtained upon flash column chromatography (ethyl acetate-hexane gradient elution) of the condensed product. Analytical data for S13: Rf=0.6 (ethyl acetate/hexane, 1/3.5, v/v $^{13}C$ NMR (176 MHz, $CDCl_3$): δ: 166.6, 156.7, 156.2, 137.9, 136.8, 132.8, 130.4, 129.5, 128.5, 128.4, 128.3, 127.8, 127.3, 127.2, 67.2, 64.8, 64.7, 50.5, 50.2, 47.0, 46.0, 28.4, 27.8, 27.4, 23.3 ppm; HRMS (ESI): m/z calcd for $C_{27}H_{29}NO_4Na$ [M+Na]+: 454.1989, found: 454.1986.

Benzyl N-benzyl(5-bromopentanyl)carbamate (12)

Sodium methoxide (~0.8 mL, 0.5 M solution) was added to a solution of S13 (1.0 g, 2.32 mmol) in $CH_3OH$ (15 mL) until pH~9 and the resulting mixture was stirred under argon for 6 h at 21° C. After that, the reaction mixture was neutralized with Amberlite IR 120 (H+) ion exchange resin, the resin was filtered off and rinsed successively with $CH_3OH$. The combined filtrate was concentrated in vacuo and this crude material was directly used for bromination. To the solution of deprotected compound (0.96 g, 2.92 mmol) dissolved in anhydrous $CH_2Cl_2$ (15 mL) were added $CBr_4$ (1.85 g, 5.55 mmol) and $PPh_3$ (1.54 g, 5.86 mmol) at 0° C. The reaction was allowed to warmup to room temperature and stirring for another 3 h. When TLC showed the reaction was completed, it was quenched with $H_2O$ at 0° C., mixture was then diluted with $CH_2Cl_2$ (~50 mL) and washed with water (2×10 mL), sat. aq. $NaHCO_3$ (15 mL), and brine (15 mL). The organic phase was separated, dried over $MgSO_4$, and concentrated in vacuo. The residue was purified by column chromatography on silica gel (ethyl acetate-hexane gradient elution) to afford the title compound 12 (1.085 g, 94.8%) as a liquid. Analytical data for 12: Rf=0.85 (ethyl acetate/hexane, 1/4, v/v); $^{13}C$ NMR (176 MHz, $CDCl_3$): δ: 156.7, 156.2, 137.8, 136.7, 128.5 (×2), 128.4, 128.0, 127.9, 127.4, 127.3, 127.2, 67.3, 67.2, 50.6, 50.3, 46.9, 46.0, 33.6, 33.4, 32.3 (×2), 27.2, 26.8, 25.3 ppm; HRMS (ESI): m/z calcd for $C_{20}H_{24}NO_2BrNa$ [M+Na]+: 412.0883, found: 412.0878.

Synthesis of p-tolyl Thioglycoside Donor 13

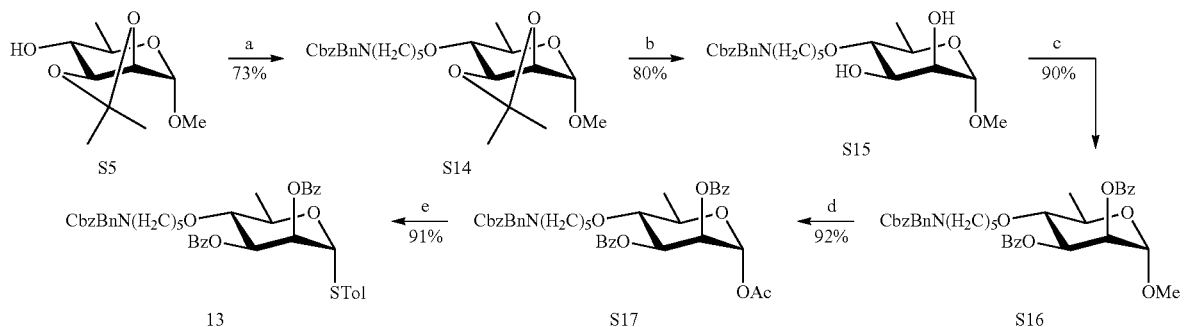

Scheme 4S. Conditions: a) CbzBnN(CH$_2$)$_5$Br, NaH, DMF, 0° C. to rt, 18 h; b) TFA/H$_2$O (9:1), CH$_2$Cl$_2$, rt, 10 min; c) BzCl, DMAP, Et$_3$N, CH$_2$Cl$_2$, 0° C. to rt, 12 h; d) Ac$_2$O, AcOH, H$_2$SO$_4$, rt, 4 h; e) BF$_3$:Et$_2$O, p-Toluenethiol, CH$_2$Cl$_2$, 0° C. to rt, 10 h.

Methyl 2,3-O-isopropylidene-6-deoxy-a-D-mannopyranoside (S5)

Analytical data for the title compound was essentially the same as previously described (Eis & Ganem (1988) Carbohydrate Research 176:316-323).

Methyl 4-O-(5'-N-benzyl-5'-N-carboxybenzyl-pentanyl) 2,3-O-isopropylidene-6-deoxy-a-D-mannopyranoside (S14)

To the solution of S5 (2.0 g, 9.17 mmol) dissolved in anhydrous DMF (15 mL) was added NaH (0.4 g, 10.08 mmol) at 0° C. The mixture was stirred at 0° C. for 45 min, and then CbzBnN(CH$_2$)$_5$Br (4.5 g, 11.01 mmol) were added. After stirring for another 12 h when TLC showed that the reaction was completed, it was quenched with H$_2$O at 0° C., and the mixture was diluted with EtOAc. The aqueous layer was extracted with EtOAc (5×25 mL), and the organic phases were combined and dried over Na$_2$SO$_4$. The desired product S14 (3.26 g, 73.2%) along with eliminated alkene and small amount unreacted starting material S5 (0.16 g) were obtained upon flash column chromatography (ethyl acetate-hexane gradient elution) of the condensed product. Analytical data for S14: Rf=0.6 (ethyl acetate/hexane, 1/4, v/v); [α]D$^{21}$=+20.48 (c=2.11, CHCl$_3$); $^{13}$C NMR (176 MHz, CDCl$_3$): δ: 156.7, 156.1, 137.9, 136.9, 136.8, 128.5, 128.4, 127.9, 127.8, 127.3, 127.2, 109.0, 98.0, 82.0, 78.5, 75.9, 71.3, 67.1, 64.5, 54.7, 50.4, 50.1, 47.1, 46.1, 29.8, 28.0, 27.9, 27.5, 26.3, 23.4, 17.7 ppm; HRMS (ESI): m/z calcd for C$_{30}$H$_{41}$NO$_7$Na [M+Na]+: 550.2775, found: 550.2785.

Methyl 4-O-(5'-N-benzyl-5'-N-carboxybenzyl-pentanyl)-6-deoxy-a-D-mannopyranoside S15

A solution of S14 (1.0 g, 1.89 mmol) in TFA:H$_2$O (9:1, 10 mL) was stirred at 21° C. for 30 min, and then poured into ice-cold 1M K$_2$CO$_3$ solution (50 mL). The mixture was then diluted with CH$_2$Cl$_2$ (~50 mL) and washed with water (2×30 mL), sat. aq. NaHCO$_3$ (25 mL), and brine (15 mL). The organic phase was separated, dried over MgSO$_4$, and concentrated in vacuo. The residue was purified by column chromatography on silica gel (ethyl acetate-hexane gradient elution) to afford the title compound S15 (0.742 g, 80.3%) as oil. Analytical data for S15: Rf=0.4 (ethyl acetate/hexane, 1/1, v/v); [α]D$^{21}$=+38.31 (c=1.27, CHCl$_3$); $^{13}$C NMR (176 MHz, CDCl$_3$): δ: 156.7, 156.3, 137.8, 136.6, 129.6, 128.5, 128.4, 127.9, 127.8, 127.3, 127.2, 100.3, 81.7, 71.4, 71.3, 71.2, 67.2, 67.1, 54.8, 50.5, 50.3, 47.1, 46.1, 30.0, 29.8, 27.9, 27.2, 23.2, 17.9 ppm; HRMS (ESI): m/z calcd for C$_{27}$H$_{37}$NO$_7$Na [M+Na]+: 510.2462, found: 510.2462.

Methyl 2,3-di-O-benzoyl-4-O-(5'-N-benzyl-5'-N-carboxybenzyl-pentanyl)-6-deoxy-a-D-mannopyranoside (S16)

Benzoyl chloride (0.23 mL, 1.97 mmol) was added dropwise to a stirred solution of S15 (0.4 g, 0.82 mmol) in anhydrous CH$_2$Cl$_2$ (10 mL) containing Et$_3$N (0.46 mL, 3.28 mmol) at 0° C. After 2 minute DMAP (0.451 g, 3.69 mmol) in anhydrous CH$_2$Cl$_2$ (5 mL) was added dropwise to the reaction mixture and stirred at rt overnight. The resulting mixture was diluted with CH$_2$Cl$_2$ (~20 mL) and washed with aq. HCl (1M, 2×5 mL), water (20 mL), sat. aq. NaHCO$_3$ (10 mL), and brine (10 mL). The organic phase was separated, dried over MgSO$_4$, and concentrated in vacuo. The residue was purified by column chromatography on silica gel (ethyl acetate-hexane gradient elution) to afford the title compound S16 (0.513 g, 90%) as oil. Analytical data for S16: Rf=0.7 (ethyl acetate/hexane, 1/3.5, v/v); [α]D$^{21}$=−70.58 (c=1.71, CHCl$_3$); $^{13}$C NMR (176 MHz, CDCl$_3$): δ: 165.5, 165.2, 156.7, 156.3, 137.9, 133.3, 133.0, 129.9, 129.8, 129.8, 129.6, 128.5, 128.4, 128.3, 127.9, 127.8, 127.1, 98.5, 79.5, 73.1, 72.9, 72.1, 71.1, 67.6, 67.1, 55.0, 50.4, 50.1, 47.0, 46.0, 29.9, 27.8, 27.4, 23.3, 18.0 ppm; HRMS (ESI): m/z calcd for C$_{41}$H$_{45}$NO$_9$Na [M+Na]+: 718.2987, found: 718.298.

1-O-acetyl-2,3-di-O-benzoyl-4-O-(5'-N-benzyl-5'-N-carboxybenzyl-pentanyl)-6-deoxy-a-D-mannopyranose (S17)

A solution of S16 (0.5 g, 0.716 mmol) in acetic anhydride/acetic acid/sulfuric acid (50:20:0.5, 10 mL) was stirred at 21° C. for 3 h, and then poured into ice-cold 1M K$_2$CO$_3$ solution (50 mL). The mixture was then diluted with CH$_2$Cl$_2$ (~20 mL) and washed with water (2×30 mL), sat. aq. NaHCO$_3$ (15 mL), and brine (10 mL). The organic phase was separated, dried over MgSO$_4$, and concentrated in vacuo. The residue was purified by column chromatography on silica gel (ethyl acetate-hexane gradient elution) to afford the title compound S17 (0.485 g, 92.2%) as a liquid.

Analytical data for S17: Rf=0.55 (ethyl acetate/hexane, 1/4, v/v); $[\alpha]D^{21}$=−48.86 (c=1.51, CHCl$_3$); $^{13}$C NMR (176 MHz, CDCl$_3$): δ: 168.6, 165.4, 165.2, 137.8, 136.7, 133.5, 133.2, 129.8, 129.6, 129.4, 129.0, 128.5, 128.5, 128.4, 128.2, 127.9, 127.8, 127.2, 127.1, 90.8, 79.1, 73.4, 71.8, 70.1, 69.9, 67.1, 50.4, 50.1, 46.9, 45.9, 29.9, 27.8, 27.4, 23.3, 21.0, 18.1, ppm; HRMS (ESI): m/z calcd for C$_{42}$H$_{45}$NO$_{10}$Na [M+Na]+: 746.2936, found: 746.2931.

p-Tolyl 2,3-di-O-benzoyl-4-O-(5'-N-benzyl-5'-N-carboxybenzyl-pentanyl)-6-deoxy-1-thio-a-D-mannopyranoside (13)

To the stirred solution of S17 (1.2 g, 1.66 mmol) and p-toluenethiol (0.312 g, 2.48 mmol) in anhydrous CH$_2$Cl$_2$ (20 mL) at 0° C., BF$_3$·Et$_2$O (0.25 mL, 1.99 mmol) was added drop wise. When TLC showed the reaction was completed, the mixture was then diluted with CH$_2$Cl$_2$ (~30 mL) and washed with water (2×10 mL), sat. aq. NaHCO$_3$ (10 mL), and brine (20 mL). The organic phase was separated, dried over MgSO$_4$, and concentrated in vacuo. The residue was purified by flash column chromatography (ethyl acetate-hexane gradient elution) to give 13 as a white solid (1.18 g, 90.7%). Analytical data for 13: Rf=0.65 (ethyl acetate/hexane, 1/4, v/v); $[\alpha]D^{21}$=−1.02 (c=0.9, CHCl$_3$); $^{13}$C NMR (176 MHz, CDCl$_3$): δ: 165.4, 165.3, 156.7, 156.1, 138.1, 137.9, 136.9, 136.8, 133.4, 133.2, 132.7, 132.3, 130.0, 129.9 (×2), 129.8, 129.7 (×2), 129.6, 128.5 (×2), 128.4 (×2), 127.9, 127.8, 127.3 (×2), 127.2, 86.2, 79.7, 73.3, 73.1, 72.6, 72.4 (×2), 69.2, 67.1, 50.5, 50.2, 47.0, 46.0, 30.0, 27.9, 27.4, 23.3, 21.2, 18.0 ppm; HRMS (ESI): m/z calcd for C$_{47}$H$_{49}$NO$_8$SNa [M+Na]+: 810.3071, found: 810.3069.

Methyl 4-azido-3-O-benzyl-4,6-dideoxy-a-D-mannopyranoside

Analytical data for the title compound was essentially the same as previously described (Bundle et al (1988) Carbohydr Res 174:239-251), (Eis & Ganem (1988) Carbohydrate Research 176:316-323).

Assembly of Heptasaccharide

Glycosylation of the methyl glycoside by the activated thioglycoside 11 provides disaccharide 14. This is subjected to a transesterification reaction to remove the acetate ester revealing the hydroxyl group for a repeated sequence of glycosylation and transesterification. This is repeated a further 4 times leading in turn to trisaccharide 16 and 17, tetrasaccharides 18 and 19, pentasaccharides 21 and 22, and hexasaccharides 22 and 23. Then in a final chain extension reaction the capping residue with tether is attached by reacting 13 with 23 to yield the heptasaccharide 24 and after removal of benzoate ester the partial deprotected alcohol 25. Deprotection is achieved in a series of steps involving reduction of azido groups to amine followed by their N-formylation and then a hydrogenolysis step to remove benzyl ethers and amino protecting groups (Ganesh et al (2014) Journal of the American Chemical Society 136: 16260-16269). Compound 8 is then conjugated to protein by selective activation of the tether amino group with bis-succinimide ester (DSG) or dibutyl squarate to give the activated intermediates S26 and S27. S26 was reacted with tetanus toxoid to provide the vaccine glyconconjugate 9 and S27 was reacted with BSA to provide the screening antigen 10.

Methyl 4-azido-2-O-acetyl-3-O-benzyl-4,6-dideoxy-a-D-mannopyranosyl (1→2) 4-azido-3-O-benzyl-4,6-dideoxy-α-D-mannopyranoside (14)

The glycosyl acceptor compound S11 (1.42 g, 4.84 mmol), and glycosyl donor compound 11 (2.27 g, 5.33 mmol), were combined, azeotroped twice with anhydrous toluene (5 mL), and placed under high vacuum for 2 h. The mixture was then dissolved in CH$_2$Cl$_2$ (20 mL), treated with freshly activated 4 A ° molecular sieves (1.5 g), stirred under an Ar atmosphere at rt for 1 h. To the mixture was added NIS (2.4 g, 9.71 mmol). After cooling to −10° C., TMSOTf (0.19 mL, 0.971 mmol) was added and the reaction was allowed to warmup to room temperature. When TLC showed the reaction was completed, saturated aqueous NaHCO$_3$ (15 mL) and CH$_2$Cl$_2$ were then added, and the resulting mixture was passed through celite to remove molecular sieves. The combined filtrates were washed with aqueous Na$_2$S$_2$O$_3$ (20%) and water. After extraction of the aqueous layer with CH$_2$Cl$_2$ (3×15), the combined organic phase was dried over Na$_2$SO$_4$, concentrated in vacuum, and purified by silica gel column chromatography (Ethyl acetate/Hexane gradient elution) to give disaccharide 14 (2.66 g, 92.1%) as a sticky liquid. Analytical data for 14: Rf=0.5 (Ethyl acetate/Hexane 1:4, v/v); $[\alpha]D^{21}$=+36.24° (c=1.92, CHCl$_3$); $^{13}$C NMR (176 MHz, CDCl$_3$): δ: 169.7, 137.6, 137.1, 128.5 (×2), 128.4, 128.0, 127.9, 127.8, 99.7, 99.4, 77.7, 75.4, 73.7, 72.0, 71.6, 67.6, 67.2, 66.9, 64.1, 63.8, 54.9, 20.9, 18.5 (×2) ppm; HRMS (ESI): m/z calcd for C$_{29}$H$_{36}$N$_6$O$_8$Na [M+Na]+: 619.2487, found: 619.2481.

Methyl 4-azido-3-O-benzyl-4,6-dideoxy-a-D-mannopyranosyl (1→2) 4-azido-3-O-benzyl-4,6-dideoxy-α-D-mannopyranoside (15)

Sodium methoxide (~1.2 mL, 0.5 M solution) was added to a solution of 14 (2.6 g, 4.36 mmol) in CH$_3$OH: THF [4:2] (20 mL) until pH~9 and the resulting mixture was stirred under argon for 6 h at 21° C. After that, the reaction mixture was neutralized with Amberlite IR 120 (H+) ion exchange resin, the resin was filtered off and rinsed successively with CH$_3$OH. The combined filtrate was concentrated in vacuo and purified by column chromatography on silica gel (Ethyl acetate-Hexane gradient elution) to deprotected disaccharide compound 15 (2.3 g, 95.4%) as white foam. Analytical data for 15: Rf=0.4 (Ethyl acetate/Hexane 1:4.5, v/v); $[\alpha]D^{21}$=+28.71 (c=1.56, CHCl$_3$); $^{13}$C NMR (176 MHz, CDCl$_3$): δ: 137.5, 137.1, 128.6, 128.5, 128.3, 128.2 (×2), 128.0, 100.8, 99.9, 77.8, 77.6, 73.6, 72.1 (×2), 67.3, 67.2, 66.9, 64.3, 63.8, 54.9, 18.6, 18.4 ppm; HRMS (ESI): m/z calcd for C$_{27}$H$_{34}$N$_6$O$_7$ [M+Na]+: 577.2381, found: 577.2381.

Methyl 2-O-acetyl-4-azido-3-O-benzyl-4,6-dideoxy-α-D-mannopyranosyl (1→2) 4-azido-3-O-benzyl-4,6-dideoxy-a-D-mannopyranosyl (1→2) 4-azido-3-O-benzyl-4,6-dideoxy-a-D-mannopyranoside (16)

The glycosyl acceptor compound 15 (2.25 g, 4.06 mmol), and glycosyl donor compound 11 (1.90 g, 4.46 mmol), were combined, azeotroped twice with anhydrous toluene (5 mL), and placed under high vacuum for 2 h. The mixture was then dissolved in CH$_2$Cl$_2$ (25 mL), treated with freshly activated 4 A ° molecular sieves (1.6 g), stirred under an Ar atmosphere at rt for 1 h. To the mixture was added NIS (1.83 g, 8.11 mmol). After cooling to −10° C., TMSOTf (0.16 mL 0.893 mmol) was added and the reaction was allowed to warmup to room temperature. When TLC showed the reaction was completed, saturated aqueous NaHCO$_3$ (15 mL) and CH$_2$Cl$_2$ were then added, and the resulting mixture was passed through celite to remove molecular sieves. The combined filtrates were washed with aqueous Na$_2$S$_2$O$_3$ (20%) [30 mL] and water (20 mL). After extraction of the aqueous layer with CH$_2$Cl$_2$ (3×15), the combined organic phase was dried over Na$_2$SO$_4$, concentrated in vacuum, and purified by silica gel column chromatography (Ethyl acetate/Hexane gradient elution) to give trisaccharide 16 (3.09 g, 88.9%) as a sticky liquid. Analytical data for 16: Rf=0.65 (Ethyl acetate/Hexane 1:5, v/v); $^{13}$C NMR (176 MHz, CDCl$_3$): δ: 169.7, 137.4, 137.3, 137.1, 128.5 (×2), 128.4, 128.1, 128.0 (×3), 100.3, 99.8, 99.1, 77.5, 76.8, 75.4, 73.5, 72.1, 72.0, 71.5, 67.8, 67.6, 67.1, 67.0, 64.4, 64.0, 63.8, 54.9, 21.0, 18.6 (×2), 18.3 ppm; HRMS (ESI): m/z calcd for C$_{42}$H$_{51}$N$_9$O$_{11}$Na [M+Na]+: 880.36, found: 880.3607.

Methyl 4-azido-3-O-benzyl-4,6-dideoxy-a-D-mannopyranosyl (1→2) 4-azido-3-O-benzyl-4,6-dideoxy-a-D-mannopyranosyl (1→2) 4-azido-3-O-benzyl-4,6-dideoxy-a-D-mannopyranoside (17)

Sodium methoxide (~1.5 mL, 0.5 M solution) was added to a solution of 16 (3.0 g, 3.5 mmol) in CH$_3$OH: THF [4:2] (20 mL) until pH~9 and the resulting mixture was stirred under argon for 6 h at 21° C. After that, the reaction mixture was neutralized with Amberlite IR 120 (H+) ion exchange resin, the resin was filtered off and rinsed successively with CH$_3$OH. The combined filtrate was concentrated in vacuo and purified by column chromatography on silica gel (Ethyl acetate-Hexane gradient elution) to afford the deprotected trisaccharide compound 17 (2.6 g, 91.2%) as white solid foam. Analytical data for 17: Rf=0.45 (Ethyl acetate/Hexane 1:5, v/v); $^{13}$C NMR (176 MHz, CDCl$_3$): δ: 137.3 (×2), 137.2, 128.6 (×3), 128.5, 128.3, 128.3, 128.2 (×2), 128.1 (×2), 128.0, 100.5, 100.4, 99.8, 77.6, 77.5, 76.8, 73.6, 73.3, 72.2, 72.1 (×2), 67.8, 67.3, 67.1, 67.0, 64.4, 64.2, 63.8, 54.9, 18.6 (×2), 18.3 ppm; HRMS (ESI): m/z calcd for C$_{40}$H$_{49}$N$_9$O$_{10}$Na [M+Na]+: 383.3495, found: 838.3501.

Methyl 2-O-acetyl-4-azido-3-O-benzyl-4,6-dideoxy-a-D-mannopyranosyl (1→2) 4-azido-3-O-benzyl-4,6-dideoxy-a-D-mannopyranosyl (1→2) 4-azido-3-O-benzyl-4,6-dideoxy-a-D-mannopyranosyl (1→2) 4-azido-3-O-benzyl-4,6-dideoxy-a-D-mannopyranoside (18)

The glycosyl acceptor compound 17 (2.05 g, 2.51 mmol), and glycosyl donor compound 11 (1.18 g, 2.76 mmol), were combined, azeotroped twice with anhydrous toluene (5 mL), and placed under high vacuum for 2 h. The mixture was then dissolved in CH$_2$Cl$_2$ (20 mL), treated with freshly activated 4 A ° molecular sieves (1.2 g), stirred under an Ar atmosphere at rt for 1 h. To the mixture was added NIS (1.13 g, 5.02 mmol). After cooling to −10° C., TMSOTf (0.1 mL, 0.553 mmol) was added and the reaction was allowed to warmup to room temperature.

When TLC showed the reaction was completed, saturated aqueous NaHCO$_3$ (10 mL) and CH$_2$Cl$_2$ were then added, and the resulting mixture was passed through celite to remove molecular sieves. The combined filtrates were washed with aqueous Na$_2$S$_2$O$_3$ (20%) and water. After extraction of the aqueous layer with CH$_2$Cl$_2$ (3×10), the combined organic phase was dried over Na$_2$SO$_4$, concentrated in vacuum, and purified by silica gel column chromatography (Ethyl acetate/Hexane gradient elution) to give tetrasaccharide 18 (2.49 g, 87.8%) as a syrup. Analytical data for 18: Rf=0.5 (Ethyl acetate/Hexane 1:4, v/v); $^{13}$C NMR (176 MHz, CDCl$_3$): δ: 169.8, 137.4, 137.3, 137.1 (×2), 128.6 (×2), 128.5 (×2), 128.4, 128.3, 128.2, 128.1, 128.0 (×3), 100.3, 100.1, 99.7, 99.1, 77.4, 76.6, 75.4, 73.6, 73.4 (×2), 72.2, 72.1, 72.0, 71.5, 67.8, 67.6, 67.1, 66.9, 64.3, 64.2, 64.0, 63.8, 54.9, 21.0, 18.6 (×2), 18.5, 18.4 ppm; HRMS (ESI): m/z calcd for C$_{55}$H$_{66}$N$_{12}$O$_{14}$Na [M+Na]+: 1141.4714, found: 1141.473.

Methyl 4-azido-3-O-benzyl-4,6-dideoxy-a-D-mannopyranosyl (1→2) 4-azido-3-O-benzyl-4,6-dideoxy-α-D-mannopyranosyl (1→2) 4-azido-3-O-benzyl-4,6-dideoxy-a-D-mannopyranosyl (1→2) 4-azido-3-O-benzyl-4,6-dideoxy-a-D-mannopyranoside (19)

Sodium methoxide (~1.2 mL, 0.5 M solution) was added to a solution of 18 (2.2 g, 1.95 mmol) in CH$_3$OH: THF [4:2] (15 mL) until pH~9 and the resulting mixture was stirred under argon for 6 h at 21° C. After that, the reaction mixture was neutralized with Amberlite IR 120 (H+) ion exchange resin, the resin was filtered off and rinsed successively with CH$_3$OH. The combined filtrate was concentrated in vacuo and purified by column chromatography on silica gel (Ethyl acetate-Hexane gradient elution) to afford the title compound 19 (1.86 g, 88.7%) as white solid. Analytical data for 19: Rf=0.4 (Ethyl acetate/Hexane 1:4, v/v); $^{13}$C NMR (176 MHz, CDCl$_3$): δ: 137.3 (×2), 137.1, 128.6 (×2), 128.5, 128.4, 128.3 (×2), 128.2 (×3), 128.1, 128.0, 100.4, 100.3, 100.2, 99.7, 77.7, 77.4, 76.6, 73.6, 73.5, 73.2, 72.2, 72.1 (×3), 67.8, 67.3, 67.1, 66.9, 64.3, 64.2 (×2), 63.8, 54.9, 18.6 (×2), 18.5, 18.3 ppm; HRMS (ESI): m/z calcd for C$_{53}$H$_{64}$N$_{12}$O$_{13}$Na [M+Na]+: 1099.4608, found: 1099.4625.

Methyl 2-O-acetyl-4-azido-3-O-benzyl-4,6-dideoxy-a-D-mannopyranosyl (1→2) 4-azido-3-O-benzyl-4,6-dideoxy-a-D-mannopyranosyl (1→2) 4-azido-3-O-benzyl-4,6-dideoxy-a-D-mannopyranosyl (1→2) 4-azido-3-O-benzyl-4,6-dideoxy-a-D-mannopyranosyl (1→2) 4-azido-3-O-benzyl-4,6-dideoxy-a-D-mannopyranoside (20)

The glycosyl acceptor compound 19 (1.63 g, 1.51 mmol), and glycosyl donor compound 11 (0.712 g, 1.66 mmol), were combined, azeotroped twice with anhydrous toluene (5 mL), and placed under high vacuum for 2 h. The mixture was then dissolved in CH$_2$Cl$_2$ (15 mL), treated with freshly activated 4 A ° molecular sieves (1 g), stirred under an Ar atmosphere at rt for 1 h. To the mixture was added NIS (0.681 g, 3.03 mmol). After cooling to −10° C., TMSOTf (0.06 mL, 0.33 mmol) was added and the reaction was allowed to warmup to room temperature. When TLC showed the reaction was completed, saturated aqueous NaHCO$_3$ (10 mL) and CH$_2$Cl$_2$ were then added, and the resulting mixture was passed through celite to remove molecular sieves. The combined filtrates were washed with aqueous Na$_2$S$_2$O$_3$ (20%) [15 mL] and water (15 mL). After extraction of the aqueous layer with CH$_2$Cl$_2$ (3×10), the combined organic phase was dried over Na$_2$SO$_4$, concentrated in vacuum, and purified by silica gel column chromatography (Ethyl acetate/Hexane gradient elution) to give pentasaccharide 20 (1.92 g, 91.9%) as a sticky liquid. Analytical data for 20: Rf=0.7 (Ethyl acetate/Hexane 1:4, v/v); $^{13}$C NMR (176 MHz, CDCl$_3$): δ: 169.8, 137.4, 137.3, 137.1, 128.6 (×3), 128.5 (×2), 128.4, 128.3 (×2), 128.2, 128.1 (×2), 128.0 (×3), 100.3, 100.2, 100.0, 99.7, 99.1, 77.4, 76.6, 76.5, 75.4, 73.7, 73.6, 73.4, 73.3, 72.2 (×2), 72.1, 72.0, 71.5, 67.8 (×2), 67.6, 67.1, 66.9, 64.3, 64.2 (×2), 64.1, 63.8, 54.9, 21.0, 18.6 (×2), 18.5 (×2), 18.4 ppm; HRMS (ESI): m/z calcd for $C_{68}H_{81}N_{15}O_{17}Na$ [M+Na]+: 1402.5827, found: 1402.5856.

Methyl 4-azido-3-O-benzyl-4,6-dideoxy-a-D-mannopyranosyl (1→2) 4-azido-3-O-benzyl-4,6-dideoxy-a-D-mannopyranosyl (1→2) 4-azido-3-O-benzyl-4,6-dideoxy-a-D-mannopyranosyl (1→2) 4-azido-3-O-benzyl-4,6-dideoxy-a-D-mannopyranosyl (1→2) 4-azido-3-O-benzyl-4,6-dideoxy-a-D-mannopyranoside (21)

Sodium methoxide (~1.2 mL, 0.5 M solution) was added to a solution of 20 (1.8 g, 1.31 mmol) in $CH_3OH$:THF [4:2] (15 mL) until pH~9 and the resulting mixture was stirred under argon for 6 h at 21° C. After that, the reaction mixture was neutralized with Amberlite IR 120 (H+) ion exchange resin, the resin was filtered off and rinsed successively with $CH_3OH$. The combined filtrate was concentrated in vacuo and purified by column chromatography on silica gel (Ethyl acetate-Hexane gradient elution) to afford the title compound 21 (1.57 g, 89.8%) as white foam. Analytical data for 21: Rf=0.55 (Ethyl acetate/Hexane 1:4, v/v); $^{13}C$ NMR (176 MHz, $CDCl_3$): δ: 137.3 (×2), 137.2, 129.0, 128.6 (×4), 128.4, 128.3 (×4), 128.2 (×2), 128.1, 128.0, 100.5, 100.3, 100.2 (×2), 99.7, 77.7, 77.4, 77.0, 76.6, 76.5, 73.7, 73.6, 73.4, 73.2, 72.2, 72.1 (×3), 67.8 (×2), 67.3, 67.1, 66.9, 64.4, 64.2, 63.8, 54.9, 18.6 (×2), 18.5 (×2), 18.3 ppm; HRMS (ESI): m/z calcd for $C_{66}H_{79}N_{15}O_{16}Na$ [M+Na]+: 1360.5721, found: 1360.5749.

Methyl 2-O-acetyl-4-azido-3-O-benzyl-4,6-dideoxy-a-D-mannopyranosyl (1→2) 4-azido-3-O-benzyl-4,6-dideoxy-a-D-mannopyranosyl (1→2) 4-azido-3-O-benzyl-4,6-dideoxy-a-D-mannopyranosyl (1→2) 4-azido-3-O-benzyl-4,6-dideoxy-a-D-mannopyranosyl (1→2) 4-azido-3-O-benzyl-4,6-dideoxy-a-D-mannopyranosyl (1→2) 4-azido-3-O-benzyl-4,6-dideoxy-a-D-mannopyranoside (22)

The glycosyl acceptor compound 21 (1.45 g, 1.08 mmol), and glycosyl donor compound 11 (0.556 g, 1.3 mmol), were combined, azeotroped twice with anhydrous toluene (5 mL), and placed under high vacuum for 2 h. The mixture was then dissolved in $CH_2Cl_2$ (15 mL), treated with freshly activated 4 A° molecular sieves (1 g), stirred under an Ar atmosphere at rt for 1 h. To the mixture was added NIS (0.488 g, 2.16 mmol). After cooling to −10° C., TMSOTf (43 µL, 0.24 mmol) was added and the reaction was allowed to warmup to room temperature. When TLC showed the reaction was completed, saturated aqueous $NaHCO_3$ (10 mL) and $CH_2Cl_2$ were then added, and the resulting mixture was passed through celite to remove molecular sieves. The combined filtrates were washed with aqueous $Na_2S_2O_3$ (20%) [10 mL] and water (15 mL). After extraction of the aqueous layer with $CH_2Cl_2$ (3×10), the combined organic phase was dried over $Na_2SO_4$, concentrated in vacuum, and purified by silica gel column chromatography (Ethyl acetate/Hexane gradient elution) to give hexasaccharide 22 (1.601 g, 90.1%) as a sticky liquid. Analytical data for 22: Rf=0.65 (Ethyl acetate/Hexane 1:4, v/v); $^{13}C$ NMR (176 MHz, $CDCl_3$): δ: 169.8, 137.4, 137.3, 137.2, 137.1 (×3), 128.6 (×4), 128.5 (×2), 128.4, 128.3 (×2), 128.2, 128.1 (×2), 128.0 (×3), 100.3, 100.1 (×2), 100.0, 99.7, 99.1, 77.4, 76.7 (×2), 76.5, 75.4, 73.6 (×2), 73.5, 73.4, 73.3, 72.2, 72.1, 72.0, 71.5, 67.8 (×4), 67.6, 67.1, 66.9, 64.3 (×2), 64.2 (×2), 64.1, 63.8, 54.9, 21.0, 18.6 (×2), 18.5 (×3), 18.4 ppm; HRMS (ESI): m/z calcd for $C_{81}H_{96}N_{18}O_{20}Na$ [M+Na]+: 1663.694, found: 1663.6982.

Methyl 4-azido-3-O-benzyl-4,6-dideoxy-a-D-mannopyranosyl (1→2) 4-azido-3-O-benzyl-4,6-dideoxy-a-D-mannopyranosyl (1→2) 4-azido-3-O-benzyl-4,6-dideoxy-a-D-mannopyranosyl (1→2) 4-azido-3-O-benzyl-4,6-dideoxy-a-D-mannopyranosyl (1→2) 4-azido-3-O-benzyl-4,6-dideoxy-a-D-mannopyranosyl (1→2) 4-azido-3-O-benzyl-4,6-dideoxy-a-D-mannopyranoside (23)

Sodium methoxide (~1.0 mL, 0.5 M solution) was added to a solution of 22 (1.3 g, 0.792 mmol) in $CH_3OH$: THF [4:2] (15 mL) until pH~9 and the resulting mixture was stirred under argon for 6 h at 21° C. After that, the reaction mixture was neutralized with Amberlite IR 120 (H+) ion exchange resin, the resin was filtered off and rinsed successively with $CH_3OH$. The combined filtrate was concentrated in vacuo and purified by column chromatography on silica gel (Ethyl acetate-Hexane gradient elution) to afford the title compound 23 (1.17 g, 92.3%) as oil. Analytical data for 23: Rf=0.5 (Ethyl acetate/Hexane 1:4, v/v $^{13}C$ NMR (126 MHz, $CDCl_3$): δ: 137.3, 137.2 (×2), 128.7 (×3), 128.6 (×2), 128.4 (×3), 128.3 (×2), 128.2, 128.1 (×3), 100.5, 100.3, 100.2 (×2), 100.1, 99.8, 77.7, 77.5, 76.6 (×2), 73.7, 73.6, 73.5 (×2), 73.3, 72.2 (×2), 72.1, 67.9, 67.8, 67.4, 67.2, 67.0, 64.4, 64.2, 63.9, 54.9, 18.7, 18.6 (×2), 18.5 (×2), 18.3 ppm; HRMS (ESI): m/z calcd for $C_{79}H_{94}N_{18}O_{19}Na$ [M+Na]+: 1621.6835, found: 1621.688.

Methyl 2,3-di-O-benzoyl-4-O-(5'-N-benzyl-5'-N-carboxybenzyl-pentanyl)-6-deoxy-a-D-mannopyranosyl (1→2) 4-azido-3-O-benzyl-4,6-dideoxy-a-D-mannopyranosyl (1→2) 4-azido-3-O-benzyl-4,6-dideoxy-a-D-mannopyranosyl (1→2) 4-azido-3-O-benzyl-4,6-dideoxy-a-D-mannopyranosyl (1→2) 4-azido-3-O-benzyl-4,6-dideoxy-a-D-mannopyranosyl (1→2) 4-azido-3-O-benzyl-4,6-dideoxy-a-D-mannopyranosyl (1→2) 4-azido-3-O-benzyl-4,6-dideoxy-a-D-mannopyranoside (24)

The glycosyl acceptor compound 23 (0.270 g, 0.169 mmol), and glycosyl donor compound 13 (0.146 g, 0.186 mmol), were combined, azeotroped twice with anhydrous toluene (5 mL), and placed under high vacuum for 2 h. The mixture was then dissolved in $CH_2Cl_2$ (10 mL), treated with freshly activated 4 A° molecular sieves (0.3 g), stirred under an Ar atmosphere at rt for 1 h. To the mixture was added NIS (0.076 g, 0.337 mmol). After cooling to −10° C., TMSOTf (6.4 µL, 0.037 mmol) was added and the reaction was allowed to warmup to room temperature. When TLC showed the reaction was completed, saturated aqueous $NaHCO_3$ (5 mL) and $CH_2Cl_2$ were then added, and the resulting mixture was passed through celite to remove molecular sieves. The combined filtrates were washed with aqueous $Na_2S_2O_3$ (20%) [10 mL] and water (10 mL). After extraction of the aqueous layer with $CH_2Cl_2$ (3×5), the combined organic phase was dried over $Na_2SO_4$, concentrated in vacuum, and purified by silica gel column chromatography (Ethyl acetate/Hexane gradient elution) to give heptasaccharide 24 (0.334 g, 87.4%) as a sticky liquid. Analytical data for 24: Rf=0.65 (Ethyl acetate/Hexane 1:4, v/v); $[α]D^{21}$=−6.71° (c=1.23, $CHCl_3$); $^{13}C$ NMR (126 MHz, $CDCl_3$): δ: 165.3, 165.1, 156.6, 156.1, 137.9, 137.5, 137.4, 137.3, 137.2 (×2), 136.8, 133.3, 133.0 (×2), 129.9, 129.8, 129.6, 129.1, 128.7 (×2), 128.6 (×2), 128.5 (×2), 128.4 (×2), 128.3 (×2), 128.2, 128.1, 127.9, 127.8, 127.3, 125.3, 100.4 (×3), 100.2 (×2), 99.8, 99.1, 79.8, 77.5, 76.7, 76.6, 73.7, 73.6, 73.5, 73.3, 72.2 (×2), 72.1 (×2), 71.9, 70.9, 68.5, 68.1, 67.9, 67.8, 67.1, 67.0, 64.4, 64.2, 63.9, 54.9, 50.5, 50.2, 47.0, 46.1, 29.7, 29.4, 27.8, 27.4, 23.3, 18.7, 18.6 (×3), 18.5 (×2), 18.0 ppm; HRMS (ESI): m/z calcd for $C_{119}H_{135}N_{19}O_{27}Na$ [M+Na]+: 2284.9667, found: 2284.9732.

Methyl 4-O-(5'-N-benzyl-5'-N-carboxybenzyl-pentanyl)-6-deoxy-a-D-mannopyranosyl (1→2) 4-azido-3-O-benzyl-4,6-dideoxy-a-D-mannopyranosyl (1→2) 4-azido-3-O-benzyl-4,6-dideoxy-a-D-mannopyranosyl (1→2) 4-azido-3-O-benzyl-4,6-dideoxy-a-D-mannopyranosyl (1→2) 4-azido-3-O-benzyl-4,6-dideoxy-a-D-mannopyranosyl (1→2) 4-azido-3-O-benzyl-4,6-dideoxy-a-D-mannopyranosyl (1→2) 4-azido-3-O-benzyl-4,6-dideoxy-a-D-mannopyranoside (25)

Sodium methoxide (~0.2 mL, 0.5 M solution) was added to a solution of 24 (0.26 g, 0.115 mmol) in $CH_3OH$: THF [2:3] (10 mL) until pH~9 and the resulting mixture was stirred under argon for 6 h at 21° C. After that, the reaction mixture was neutralized with Amberlite IR 120 (H+) ion exchange resin, the resin was filtered off and rinsed successively with $CH_3OH$. The combined filtrate was concentrated in vacuo and purified by column chromatography on silica gel (Ethyl acetate-Hexane gradient elution) to afford the title compound 25 (0.215 g, 91.2%) as oil. Analytical data for 25: Rf=0.25 (Ethyl acetate/Hexane 1:3.3, v/v); $[\alpha]D^{21}$=+79.2 (c=2.21, $CHCl_3$); $^{13}C$ NMR (176 MHz, $CDCl_3$): δ: 156.7, 156.3, 137.8, 137.4, 137.3, 137.2 (×2), 137.1 (×2), 136.7, 129.0, 128.6 (×2), 128.5, 128.4, 128.3 (×2), 128.2, 128.1, 128.0, 127.9, 127.8, 127.3, 100.8, 100.4, 100.3, 100.2, 100.1 (×2), 99.7, 81.6, 77.4, 76.5, 73.6, 73.6, 73.5, 73.5, 72.9, 72.2, 72.1, 72.1, 72.0, 71.7, 71.1, 68.2, 67.8, 67.7, 67.2, 66.9, 64.3, 64.2, 54.9, 50.5, 50.3, 47.1, 46.1, 29.7, 29.4, 27.9, 27.2, 23.3, 18.6 (×2), 18.5 (×4), 17.9 ppm; HRMS (ESI): m/z calcd for $C_{105}H_{131}N_{20}O_{25}$ [M+$NH_4$]+: 2071.9589, found: 2071.9639.

Methyl 4-O-(5'-aminopentanyl)-6-deoxy-a-D-mannopyranosyl (1→2) 4,6-dideoxy-4-formamido-a-D-mannopyranosyl (1→2) 4,6-dideoxy-4-formamido-a-D-mannopyranosyl (1→2) 4,6-dideoxy-4-formamido-a-D-mannopyranosyl (1→2) 4,6-dideoxy-4-formamido-a-D-mannopyranosyl (1→2) 4,6-dideoxy-4-formamido-a-D-mannopyranosyl (1→2) 4,6-dideoxy-4-formamido-a-D-mannopyranoside (8)

To a stirred solution of 25 (0.11 g, 0.054 mmol), in pyridine (5 mL) and water (2 mL) mixture, $H_2S$ was bubbled for 0.5 h at 40° C., and continued stirring for 16 h. After that, argon was bubbled for 10 min, solvents were removed in vacuo, and the residue was co-evaporated with toluene (3×10 mL) and dried. The mass spectrometry analysis showed completion of reaction to corresponding amine compound and no products arising from incomplete reduction. HRMS (ESI): m/z calcd for $C_{105}H_{140}N_7O_{25}$ [M+H]+: 1898.9893, found: 1898.99.

This crude material was directly used for formylation Amine compound in $CH_3OH$ (5 mL) at −20° C. was added a freshly prepared formic anhydride (5 mL, ethereal solution) and stirred for 3 h, then slowly allowed to warm to 21° C. After that, solvents were evaporated and the residue was passed through column chromatography on silica gel (methanol-dichloromethane gradient elution) to afford heptasaccharide. The high resolution mass spectrometry analysis showed completion of formylation reaction. HRMS (ESI): m/z calcd for $C_{111}H_{139}N_7O_{31}Na$ [M+Na]+: 2088.9408, found: 2088.9405.

Formylated compound was dissolved in $CH_3OH/H_2O$ (2:1, 10 mL), Pd(OH)$_2$ on carbon (20%, 0.060 g) was added. Then it was stirred under a pressure of hydrogen gas at 21° C. for 16 h. After filtration through celite pad and washed with $CH_3OH$ (3×10 mL), and solvents were removed in vacuo. The residue was purified by reversed phase HPLC on C18 column in gradient water-acetonitrile and lyophilized, to give the title compound 8 (0.0427 g, 61.2%, over 3 steps) as white foam. Analytical data for 8: $[\alpha]D^{21}$=+42.44 (c=1.02, $H_2O$); $^{13}C$ NMR (126 MHz, $CDCl_3$): δ: 168.8 (×2), 168.6, 165.9 (×4), 165.7, 103.2, 103.1 (×4), 102.7, 102.5, 101.5 (×2), 100.4, 100.3, 81.8, 78.2, 78.1 (×3), 78.0 (×2), 77.9, 73.5 (×2), 71.3, 70.8 (×2), 69.2, 68.7 (×2), 68.5, 68.4, 67.8, 57.9, 56.4, 55.9, 55.8 (×2), 52.9 (×2), 52.7 (×2), 40.4, 29.7, 27.5, 23.2, 17.9 (×2), 17.8 (×2), 17.7, 17.6 (×4) ppm; HRMS (ESI): m/z calcd for $C_{54}H_{92}N_7O_{29}$ [M+H]+: 1302.5934, found: 1302.5928.

Methyl 4-O-(5'-[N-succinimidyl]glutarylamidopentanyl)-6-deoxy-a-D-mannopyranosyl (1→2) 4,6-dideoxy-4-formamido-a-D-mannopyranosyl (1→2) 4,6-dideoxy-4-formamido-a-D-mannopyranosyl (1→2) 4,6-dideoxy-4-formamido-a-D-mannopyranosyl (1→2) 4,6-dideoxy-4-formamido-a-D-mannopyranosyl (1→2) 4,6-dideoxy-4-formamido-a-D-mannopyranosyl (1→2) 4,6-dideoxy-4-formamido-a-D-mannopyranoside (S26)

A mixture of heptasaccharide 8 (9 mg) and disuccinimidal glutarate (15 eq.) in DMF and 0.1 M PBS buffer (4:1, 1.5 mL) was stirred at rt for 6 h. The reaction mixture was concentrated under vacuum and the residue was washed with EtOAc 10 times to remove the excess disuccinimidal glutarate. The resultant solid was dried under vacuum for 1 h to obtain activated oligosaccharide S26 that was directly used for conjugation with BSA & tetanus toxoid. MALDI TOF MS (positive mode): calcd for $C_{63}H_{100}N_8O_{34}Na$ [M+Na]+ m/z, 1535.6342; found, 1535.9996.

1-[(2'-Aminoethylamido)carbonylpentyl)-6-deoxy-a-D-mannopyranosyl (1→2) 4,6-dideoxy-4-formamido-a-D-mannopyranosyl (1→2) 4,6-dideoxy-4-formamido-a-D-mannopyranosyl (1→2) 4,6-dideoxy-4-formamido-a-D-mannopyranosyl (1→2) 4,6-dideoxy-4-formamido-a-D-mannopyranosyl (1→2) 4,6-dideoxy-4-formamido-a-D-mannopyranosyl (1→2) 4,6-dideoxy-4-formamido-a-D-mannopyranoside] 2-butoxycyclobutene-3,4-dione (S27)

To a stirred solution of heptasaccharide 8 (0.006 g, 0.005 mmol) in water (0.5 mL) and EtOH (0.5 mL), a solution of 3,4-dibutoxy-3-cyclobutene-1,2-dione (20% in ethanol, 50 μL) was added and pH was adjusted to 8 by careful addition of aq.$NaHCO_3$ (1%) solution. After 1 h, mass spectrometry showed the reaction was complete; the reaction mixture was neutralized using $CH_3COOH$ (10%) and concentrated in vacuo. The residue was purified by reversed phase HPLC on C18 column in gradient water-acetonitrile and lyophilized, to give the title compound S27 (0.005 g, 72.6%) as white foam. Analytical data for S27: $^{13}C$ NMR (126 MHz, $CDCl_3$): δ: 190.3, 184.2, 183.8, 178.4, 178.0, 174.3, 168.8, 168.7, 168.6, 165.7, 165.9, 103.2 (×4), 102.8, 102.6, 101.6, 100.4, 100.3, 81.9, 78.2, 78.1 (×2), 78.0 (×2), 77.9, 73.4, 71.3, 70.7, 69.8, 69.2, 69.1, 68.8, 68.6, 68.5, 68.4, 57.9, 56.4, 55.9, 55.8, 52.9 (×2), 52.7, 40.4, 32.4, 30.7, 30.5, 29.7, 27.5, 23.3, 23.2, 19.2, 19.0, 17.9, 17.8 (×2), 17.7 (×4), 17.6, 13.9 ppm; HRMS (ESI): m/z calcd for $C_{62}H_{99}N_7O_{32}Na$ [M+Na]+: 1476.6335, found: 1476.6406.

Oligosaccharide Protein Conjugation:

Preparation of tetanus toxoid conjugate 9 (Structure XVI): Activated heptasaccharide S26 (0.8 mg, 0.518 µmol) was added to the solution of tetanus toxoid (4 mg, 0.026 µmol) in 0.5 M borate buffer pH 9 (1 mL) and stirred slowly at 21° C. for 3 days. Then the reaction mixture was washed with PBS buffer, filtered through millipore filtration tube (10,000 MWCO, 4×10 mL) and the resulting tetanus toxoid-conjugate 9 was stored in PBS buffer. The MALDI-TOF mass spectrometry analysis indicated the conjugate 9 had an average of 10.02 heptasaccharide per tetanus toxoid.

Preparation of BSA conjugate 10 (Structure XVII): BSA (10 mg) and activated heptasaccharide S27 (4.5 mg) were dissolved in 0.1 M PBS buffer pH 9 (1.2 mL) and stirred slowly at 21° C. for 3 days. Then the reaction mixture was diluted with Mili-Q water, filtered through millipore filtration tube (10,000 MWCO, 4×10 mL), lyophilized and the BSA-conjugate 10 was obtained as a white foam (12.2 mg). The MALDI-TOF mass spectrometry analysis indicated the conjugate 10 had an average of 10.27 heptasaccharide per BSA.

Synthesis of exclusively 1,2-linked trisaccharide

Ethyl 4-azido-2,3-di-O-benzoyl-4,6-dideoxy-α-D-mannopyranosyl (1→2) 4-azido-3-O-benzyl-4,6-dideoxy-1-thio-α-D-mannopyranoside (S18)

Analytical data for the title compound was essentially the same as previously described (Bundle et al (1988) *Carbohydr. Res.* 174, 239-251).

5'-Methoxycarbonylpentyl 4-azido-3-O-benzyl-4,6-dideoxy-α-D-mannopyranoside (S19)

Analytical data for the title compound was essentially the same as previously described (Ganesh et al (2014) *J. Amer. Chem. Soc.* 136,16260-16269.

5'-Methoxycarbonylpentyl 4-azido-2,3-O-benzoyl-4,6-dideoxy-α-D-mannopyranosyl (1->2) 4-azido-3-O-benzyl-4,6-dideoxy-α-D-mannopyranosyl (1->2) 4-azido-3-O-benzyl-4,6-dideoxy-α-D-mannopyranoside (S20)

The glycosyl acceptor compound S19 (0.2 g, 0.491 mmol), and glycosyl donor compound S18 (0.414 g, 0.589 mmol), were combined, azeotroped twice with anhydrous toluene (5 mL), and placed under high vacuum for 2 h. The mixture was then dissolved in $CH_2Cl_2$ (15 mL), treated with freshly activated 4 A ° molecular sieves (1 g), stirred under an Ar atmosphere at rt for 1 h. To the mixture was added NIS (0.221 g, 0.982 mmol). After cooling to −10° C., TMSOTf (19.5 µL, 0.108 mmol) was added and the reaction was allowed to warmup to room temperature. When TLC showed the reaction was completed, saturated aqueous $NaHCO_3$ (5 mL) and $CH_2Cl_2$ were then added, and the resulting mixture was passed through celite to remove molecular sieves. The combined filtrates were washed with aqueous $Na_2S_2O_3$ (20%) and water. After extraction of the aqueous layer with $CH_2Cl_2$ (3×5), the combined organic phase was dried over $Na_2SO_4$, concentrated in vacuum, and purified by silica gel column chromatography (ethyl acetate-Hexane gradient elution) to give disaccharide S20 (0.418 g, 81.3%) as a sticky liquid. Analytical data for S20: Rf=0.7 (ethyl acetate/Hexane 1:4.5, v/v); $[α]D^{21}$=−14.49° (c=1.79, $CHCl_3$); $^1H$ NMR (500 MHz, $CDCl_3$): δ 8.02-8.05 (m, 2H, ArH), 7.95-7.97 (m, 2H, ArH), 7.64-7.68 (m, 1H, ArH), 7.50-7.57 (m, 3H, ArH), 7.33-7.41 (m, 8H, ArH), 7.22-7.26 (m, 3H, ArH), 7.13-7.17 (m, 1H, ArH), 5.71 (dd, J=3.3, 1.5 Hz, 1H, H-2$_C$), 5.59 (dd, J=10.3, 3.3 Hz, 1H, H-3$_C$), 5.06 (d, J=1.8 Hz, 1H, H-1$_B$), 5.02 (d, J=1.8 Hz, 1H, H-1$_C$), 4.76 (d, J=11.7 Hz, 1H, C$\underline{H}$Ph), 4.62-4.69 (m, 4H, 3 C$\underline{H}$Ph, H-1$_A$), 3.95 (dd, J=2.2, 0.7 Hz, 1H, H-2$_B$), 3.90 (dd, J=2.2, 0.7 Hz, 1H, H-2$_A$), 3.76-3.81 (m, 2H, H-3$_B$, H-5$_B$), 3.74 (dd, J=9.9, 2.9 Hz, 1H, H-3$_A$), 3.71 (s, 3H), 3.69 (t, J=9.9 Hz, 1H, H-4$_C$), 3.55-3.65 (m, 3H, H-4$_B$, H-5$_C$, —O—C$\underline{H}_{2b}$), 3.43-3.49 (m, 1H, H-5$_A$), 3.38 (dt, J=9.7, 6.4 Hz, 1H, —O—C$\underline{H}_{2a}$), 3.27 (t, J=9.9 Hz, 1H, H-4$_A$), 2.33-2.39 (m, 2H, —C$\underline{H}_2$f), 1.64-1.72 (m, 2H, —C$\underline{H}_{2e}$), 1.56-1.64 (m, 2H, —C$\underline{H}_{2c}$), 1.35-1.42 (m, 2H, —C$\underline{H}_{2d}$), 1.38 (d, J=5.6 Hz, 3H, H-6$_C$), 1.32 (d, J=5.9 Hz, 3H, H-6$_B$), 1.29 (d, J=5.9 Hz, 3H, H-6$_A$); $^{13}C$ NMR (126 MHz, $CDCl_3$): δ 174.0, 165.2, 164.9, 137.5, 137.3, 133.4, 133.3, 129.8 (×2), 129.6, 129.3, 128.5 (×2), 128.4, 128.2, 128.1 (×2), 128.0, 100.3, 99.0, 98.8, 77.9, 73.9, 73.5, 72.3 (×2), 70.9, 69.5, 68.0, 67.5, 67.2, 64.5, 63.9, 63.5, 51.5, 34.0, 29.1, 25.7, 24.7, 18.6 (×2), 18.4 ppm; HRMS (ESI): m/z calcd for $C_{53}H_{61}N_9O_{14}Na$ [M+Na]+: 1070.423, found: 1070.4248.

5'-Methoxycarbonylpentyl 4-azido-4,6-dideoxy-α-D-mannopyranosyl (1->2) 4-azido-3-O-benzyl-4,6-dideoxy-α-D-mannopyranosyl (1->2) 4-azido-3-O-benzyl-4,6-dideoxy-α-D-mannopyranoside (S21)

Sodium methoxide (~0.3 mL, 0.5 M solution) was added to a solution of S20 (0.39 g, 0.372 mmol) in $CH_3OH$: THF [4:2] (12 mL) until pH~9 and the resulting mixture was stirred under argon for 6 h at 21° C. After that, the reaction mixture was neutralized with Amberlite IR 120 (H+) ion exchange resin, the resin was filtered off and rinsed successively with $CH_3OH$. The combined filtrate was concentrated in vacuo and purified by column chromatography on silica gel (ethyl acetate-Hexane gradient elution) to afford the title compound S21 (0.299 g, 95.6%) as white solid. Analytical data for S21: Rf=0.3 (ethyl acetate/Hexane 1:1.5, v/v); $[α]D^{21}$=+84.18 (c=1.55, $CHCl_3$); $^1H$ NMR (500 MHz, $CDCl_3$): δ 7.30-7.44 (m, 10H, ArH), 5.00 (d, J=1.8 Hz, 1H, H-1$_B$), 4.90 (d, J=1.5 Hz, 1H, H-1$_C$), 4.72 (d, J=11.4 Hz, 1H, C$\underline{H}$Ph), 4.61-4.67 (m, 4H, 3 C$\underline{H}$Ph, H-1$_A$), 3.93-3.97 (m, 2H, H-2$_B$, H-2$_C$), 3.81-3.87 (m, 2H, H-2$_A$, H-3$_A$), 3.76 (dd, J=9.9, 2.9 Hz, 1H, H-3$_B$), 3.73 (dd, J=10.0, 2.9 Hz, 1H, H-3$_C$), 3.70 (s, 3H), 3.51-3.64 (m, 3H, H-5$_B$, H-5$_C$, —O—C$\underline{H}_{2b}$), 3.43-3.49 (m, 1H, H-5$_A$), 3.40 (t, J=9.9 Hz, 1H, H-4$_C$), 3.36 (dt, J=9.7, 6.4 Hz, 1H, —O—C$\underline{H}_{2a}$), 3.27 (t, J=9.9 Hz, 1H, H-4$_B$), 3.40 (t, J=10.2 Hz, 1H, H-4$_A$), 2.49 (d, J=6.9 Hz, 1 OH$_{3C}$), 2.34 (t, J=7.4 Hz, 2H, —C$\underline{H}_2$f), 2.18 (d, J=3.9 Hz, 1 OH$_{2C}$), 1.63-1.70 (m, 2H, —C$\underline{H}_{2c}$), 1.54-1.61 (m, 2H, —C$\underline{H}_{2c}$), 1.33-1.40 (m, 2H, —C$\underline{H}_{2d}$), 1.30 (d, J=6.2 Hz, 6H, H-6$_B$, H-6$_C$), 1.20 (d, J=6.2 Hz, 3H, H-6$_A$); $^{13}C$ NMR (126 MHz, $CDCl_3$): δ 174.0, 137.4 (×2), 128.6 (×2), 128.3, 128.2 (×2), 128.1, 100.7, 100.4, 98.7, 77.7, 77.2, 77.2, 73.8, 73.2, 72.3, 72.2, 70.2, 69.9, 67.8, 67.5, 67.4, 67.1, 65.8, 64.4, 64.2, 51.6, 33.9, 29.1, 25.7, 24.7, 18.6 (×2), 18.2 ppm; HRMS (ESI): m/z calcd for $C_{39}H_{53}N_9O_{12}Na$ [M+Na]+: 862.3706, found: 862.3705.

5'-Methoxycarbonylpentyl 4,6-dideoxy-4-formamido-α-D-mannopyranosyl (1→2) 4,6-dideoxy-4-formamido-α-D-mannopyranosyl (1→2) 4,6-dideoxy-4-formamido-α-D-mannopyranoside (4)

To a stirred solution of S21 (0.2 g, 0.239 mmol), in pyridine (5 mL) and water (2 mL) mixture, $H_2S$ was bubbled for 0.5 h at 40° C., and continued stirring for 16 h. After that, argon was bubbled for 10 min, solvents were removed in vacuo, and the residue was co-evaporated with toluene (3×10 mL) and dried. The mass spectrometry analysis showed completion of reaction to corresponding amine compound and no products arising from incomplete reduction.

This crude material was directly used for formylation Amine compound in $CH_3OH$ (5 mL) at −20° C. was added a freshly prepared formic anhydride (5 mL, ethereal solution) and stirred for 3 h, then slowly allowed to warm to 21° C. After that, solvents were evaporated and the residue was passed through column chromatography on silica gel (methanol-dichloromethane gradient elution) to afford trisaccharide. The high resolution mass spectrometry analysis showed completion of formylation reaction. HRMS (ESI): m/z calcd for $C_{42}H_{59}N_3O_{15}Na$ [M+Na]+: 868.3838, found: 868.3837.

Formylated compound was dissolved in $CH_3OH/H_2O$ (2:1, 15 mL), $Pd(OH)_2$ on carbon (20%, 0.090 g) was added. Then it was stirred under a pressure of hydrogen gas at 21° C. for 16 h. After filtration through celite pad and washed with $CH_3OH$ (3×10 mL), and solvents were removed in vacuo. The residue was purified by reversed phase HPLC on C18 column in gradient water-acetonitrile and lyophilized, to give the title compound 4 (0.094 g, 59.3%, over 3 steps) as white foam. Analytical data for 4: $[α]D^{21}$=+31.58 (c=1.16, $H_2O$); $^1H$ NMR (700 MHz, $D_2O$): δ 8.20-8.24 (Z) and 8.03-8.06 07 (E) (m, 3H, NCHO), 5.16-5.22 (m, 1H, H-1$_B$), 5.05-5.08 (m, 1H, H-1$_C$), 4.89-4.93 (m, 1H, H-1$_A$), 4.13-4.19 (m, 1H, H-2$_B$), 4.06-4.13 (m, 2H, H-2$_C$, H-3$_C$), 3.92-4.03 (m, 6H, H-2$_A$, H-3$_A$, H-3$_B$, H-4$_C$, H-4$_B$, H-4$_A$), 3.87-3.92 (m, 2H, H-5$_A$, H-5$_C$), 3.80-3.84 (m, 1H, H-5$_B$), 3.71-3.75 (m, 1H, —O—C$\underline{H}_{2b}$), 3.71 (s, 3H), 3.56 (dt, J=9.9, 5.9 Hz, 1H, —O—C$\underline{H}_{2a}$), 2.42 (t, J=7.4 Hz, 2H, —C$\underline{H}_{2f}$), 1.60-1.68 (m, 4H, —C$\underline{H}_{2e}$, —C$\underline{H}_{2c}$), 1.40 (dq, J=14.8, 7.3 Hz, 2H, —C$\underline{H}_{2d}$), 1.20-1.30 (m, 9H, 3×H-6); $^{13}C$ NMR (176 MHz, $D_2O$): δ 178.4, 168.6 (×2), 165.7, 165.7 (×2), 102.9, 102.8, 101.5, 99.1, 78.5, 78.4, 78.2, 78.1, 78.0, 69.8, 69.1, 68.8, 68.7 (×2), 68.6, 68.5 (×2), 68.3 (×2), 67.9, 57.8, 52.9, 52.8, 52.7 (×2), 52.5, 34.4 (×2), 28.9, 25.7, 24.8, 17.8 (×2), 17.7 (×2), 17.6, 17.5 (×2) ppm. HRMS (ESI): m/z calcd for $C_{28}H_{47}N_3O_{15}Na$ [M+Na]+: 688.2899, found: 688.2908.

(2'-Aminoethylamido)carbonylpentyl 4,6-dideoxy-4-formamido-α-D-mannopyranosyl (1→2) 4,6-dideoxy-4-formamido-α-D-mannopyranosyl (1→2) 4,6-dideoxy-4-formamido-α-D-mannopyranoside (S24)

A solution of 4 (0.06 g, 0.09 mmol) in freshly distilled 1,2-diaminoethane (3.0 mL) was stirred at 65° C. for 48 h. After that, excess reagent was removed in vacuo, and the residue was co-evaporated with $CH_3OH$ (3×10 mL) and dried. The residue was purified by reversed phase HPLC on C18 column in gradient water-acetonitrile and lyophilized, to give the title compound S24 (0.052 g, 83.15%) as white foam. Analytical data for S24: $[α]D^{21}$=+37.05 (c=1.14, $H_2O$); $^1H$ NMR (500 MHz, $D_2O$): δ 8.24-8.33 (Z) and 8.05-8.12 (E) (m, 3H, NCHO), 5.23-5.26 (m, 1H, H-1$_B$), 5.12 (s, 1H, H-1$_C$), 4.93-4.97 (m, 1H, H-1$_A$), 4.19-4.24 (m, 1H, H-2$_B$), 4.10-4.18 (m, 2H, H-2$_C$, H-3$_C$), 3.96-4.08 (m, 6H, H-2$_A$, H-3$_A$, H-3$_B$, H-4$_C$, H-4$_B$, H-4$_A$), 3.91-3.96 (m, 2H, H-5$_A$, H-5$_C$), 3.84-3.89 (m, 1H, H-5$_B$), 3.77 (dt, J=9.7, 6.8 Hz, 1H, —O—C$\underline{H}_{2b}$), 3.57-3.63 (m, 1H, —O—C$\underline{H}_{2a}$), 3.33 (t, J=6.2 Hz, 2H, —C$\underline{H}_{2g}$), 2.82 (t, J=6.2 Hz, 2H, —C$\underline{H}_{2h}$), 2.33 (t, J=7.4 Hz, 2H, —C$\underline{H}_{2f}$), 1.64-1.74 (m, 4H, —C$\underline{H}_{2e}$, —C$\underline{H}_{2c}$), 1.39-1.49 (m, 2H, —C$\underline{H}_{2d}$), 1.25-1.35 (m, 9H, 3×H-6); $^{13}C$ NMR (126 MHz, $D_2O$): δ 178.3, 168.8 (×2), 165.8 (×2), 103.0, 102.9, 101.6, 99.3, 78.6, 78.3, 78.2, 78.1, 69.9, 69.2, 69.0, 68.9, 68.8 (×2), 68.6 (×2), 68.5, 68.4, 57.7, 53.0, 52.8 (×2), 52.7, 42.1, 42.1, 40.7, 36.7, 29.1, 26.0, 25.9, 17.9 (×2), 17.8 (×2), 17.7 (×2), 17.6 ppm; HRMS (ESI): m/z calcd for $C_{29}H_{51}N_5O_{14}Na$ [M+Na]+: 716.3325, found: 716.333.

1-[(2'-Aminoethylamido)carbonylpentyl 4,6-dideoxy-4-formamido-α-D-mannopyranosyl (1→2) 4,6-dideoxy-4-formamido-α-D-mannopyranosyl (1→2) 4,6-dideoxy-4-formamido-α-D-mannopyranoside] 2-butoxycyclobutene-3,4-dione (S25)

To a stirred solution of S24 (0.015 g, 0.022 mmol) in water (0.5 mL) and EtOH (0.5 mL), a solution of 3,4-dibutoxy-3-cyclobutene-1,2-dione (20% in ethanol, 70 μL) was added and pH was adjusted to 8 by careful addition of aq.$NaHCO_3$ (1%) solution. After 1 h, mass spectrometry showed the reaction was complete; the reaction mixture was neutralized using $CH_3COOH$ (10%) and concentrated in vacuo. The residue was purified by reversed phase HPLC on C18 column in gradient water-acetonitrile and lyophilized, to give the title compound S25 (0.0133 g, 73.2%) as white foam. Analytical data for S25: $^1H$ NMR (700 MHz, $D_2O$): δ 8.21-8.23 (Z) and 8.05 (E) (m, 3H, NCHO), 5.19 (s, 1H, H-1$_B$), 5.07 (s, 1H, H-1$_C$), 4.90-4.92 (m, 1H, H-1$_A$), 4.68-4.75 (m, 2H, —C$\underline{H}_{2i}$), 4.14-4.19 (m, 1H, H-2$_B$), 4.07-4.13 (m, 2H, H-2$_C$, H-3$_C$), 3.92-4.02 (m, 6H, H-2$_A$, H-3$_A$, H-3$_B$, H-4$_C$, H-4$_B$, H-4$_A$), 3.89 (m, 2H, H-5$_A$, H-5$_C$), 3.79-3.85 (m, 1H, H-5$_B$), 3.73 (t, J=5.0 Hz, 1H, —C$\underline{H}_{2g}$), 3.65-3.71 (m, 1H, —O—C$\underline{H}_{2b}$), 3.62 (t, J=5.0 Hz, 1H, —C$\underline{H}_{2g}$), 3.51 (dd, J=9.6, 6.5 Hz, 1H, —O—C$\underline{H}_{2a}$), 3.40-3.45 (m, 2H, —C$\underline{H}_{2h}$), 2.19-2.27 (m, 2H, —C$\underline{H}_{2f}$), 1.77-1.84 (m, 2H, —C$\underline{H}_{2j}$), 1.51-1.64 (m, 4H, —C$\underline{H}_{2e}$, —C$\underline{H}_{2c}$), 1.46 (dt, J=15.5, 7.9 Hz, 2H, —C$\underline{H}_{2k}$), 1.30-1.36 (m, 2H, —C$\underline{H}_{2d}$), 1.20-1.30 (m, 9H, 3×H-6), 0.94-0.98 (m, 3H, —C$\underline{H}_{2l}$); $^{13}C$ NMR (176 MHz, $D_2O$): δ 189.7, 184.1, 178.4, 177.8, 174.5, 168.6, 165.7, 165.7, 102.8, 101.5, 99.1, 98.9, 78.4, 78.1, 75.2, 75.1, 69.8, 69.1, 68.8, 68.7, 68.6, 68.4, 68.3 (×2), 57.8, 52.9, 52.7, 52.5, 45.0, 44.9, 40.2, 40.0, 36.6, 32.3, 29.1, 26.0, 25.9, 25.8, 25.7, 19.0, 18.9, 17.8 (×2), 17.7 (×2), 17.6, 17.5, 13.8 ppm; HRMS (ESI): m/z calcd for $C_{37}H_{59}N_5O_{17}Na$ [M+Na]+: 868.3798, found: 868.3808.

Preparation of BSA conjugate 5: BSA (15 mg) and trisaccharide squarate S25 (3.8 mg, 6.77 μmol) were dissolved in 0.1 M PBS buffer pH 9 (600 μL) and stirred slowly at 21° C. for 3 days. Then the reaction mixture was diluted with Mili-Q water, filtered through millipore filtration tube (10,000 MWCO, 4×10 mL), lyophilized and the BSA-conjugate 5 was obtained as a white foam (17.6 mg). The MALDI-TOF mass spectrometry analysis indicated the conjugate 5 had an average of 16.2 disaccharides per BSA.

The invention claimed is:
1. A diagnostic conjugate comprising a trisaccharide consisting of three units of 4,6-dideoxy-4-formamido-α-D-mannopyranose and comprising only $C_1$-$C_2$ links or comprising a disaccharide consisting of two units of 4,6-dideoxy-4-formamido-α-D-mannopyranose joined by a $C_1$-$C_2$ link, wherein the trisaccharide or disaccharide is linked to a non-saccharide carrier via the reducing end and wherein the non-saccharide carrier comprises a protein, surface, or bead that allows the detection of the presence of an antibody in a sample.

2. The diagnostic conjugate according to claim 1, wherein
i) the trisaccharide is Structure XII:

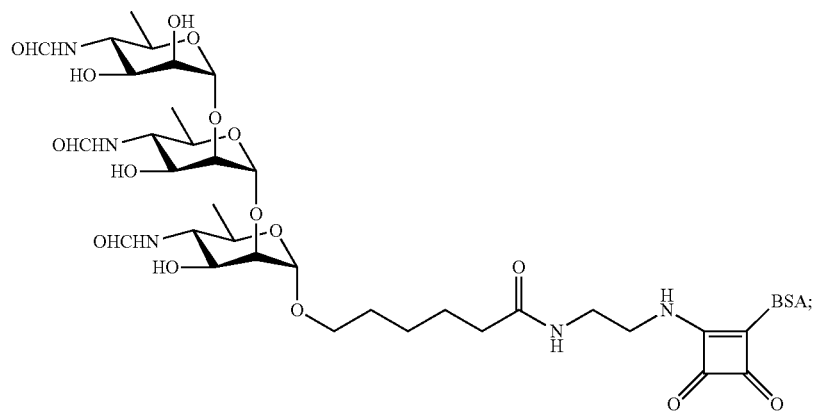

or ii) the disaccharide is Structure XI:

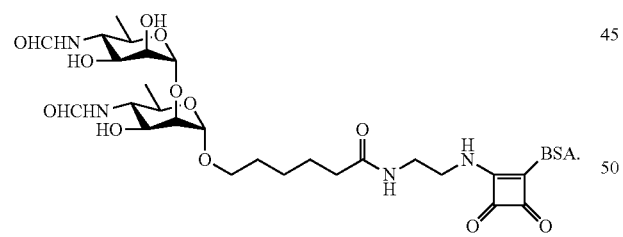

3. A diagnostic composition comprising the diagnostic conjugate according to claim 1, and further comprising a diagnostic conjugate comprising a monosaccharide consisting of one unit of 4,6-dideoxy-4-formamido-α-D-mannopyranose linked to a non-saccharide carrier via the $C_1$ carbon or a tetrasaccharide consisting of four units of 4,6-dideoxy-4-formamido-α-D-mannopyranose and comprising a central $C_1$-$C_3$ link and two $C_1$-$C_2$ links, the tetrasaccharide linked to a non-saccharide carrier via the reducing end, wherein the non-saccharide carrier allows the detection of the presence of an antibody in a sample.

4. A method for vaccinating an animal against infection by a *Brucella* organism, comprising:

(i) administering to the animal a protective amount of a molecule comprising a chain of seven or more contiguous units of 4,6-dideoxy-4-formamido-α-D-mannopyranose, adjacent units being joined by a $C_1$-$C_2$ or a $C_1$-$C_3$ link, the chain having a terminal end and a reducing end, wherein the pyranose ring in the unit of the chain most distal from the reducing end is linked to a cap structure; and (ii) obtaining a biological sample from the animal and contacting it with the diagnostic conjugate according to claim 1.

5. The method according to claim 4, wherein the method further comprises contacting the sample with a universal antigen comprising at least 6 consecutive units of 4,6-dideoxy-4-formamido-α-D-mannopyranose comprising $C_1$-$C_2$ links between most or all pairs of units and optionally comprising at least one $C_1$-$C_3$ link between a pair of units.

6. The method according to claim 5, wherein the universal antigen has or comprises a structure selected from the group consisting of:

i) the structure VIII:
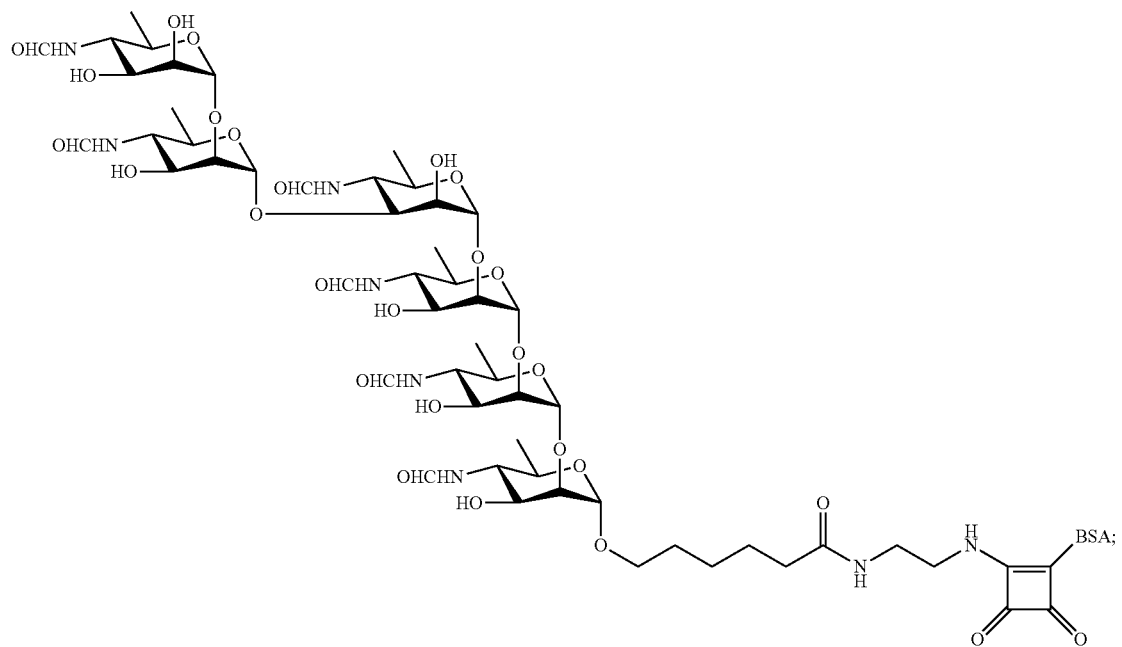
ii) the structure IX:
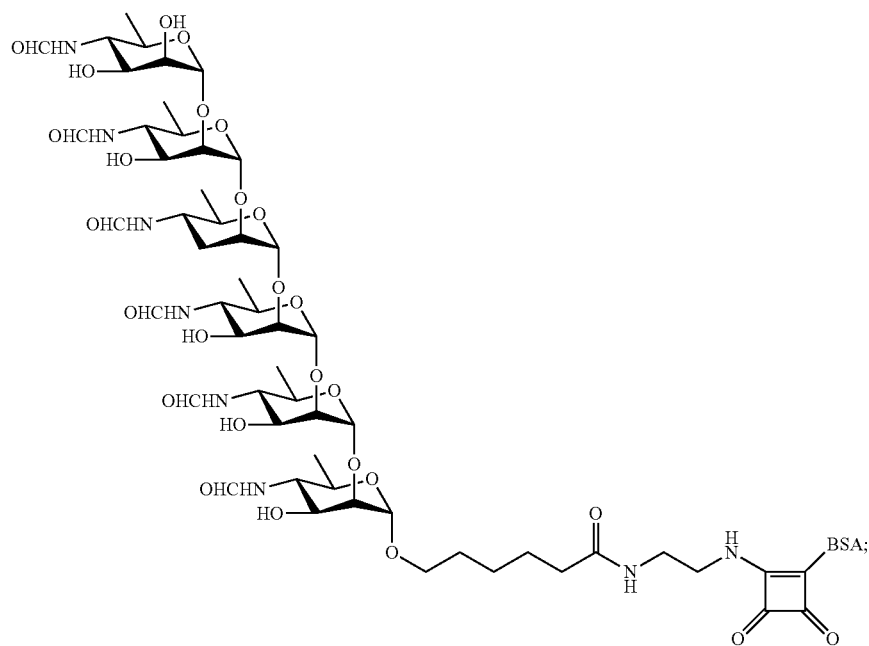

or iii) the structure XIX:

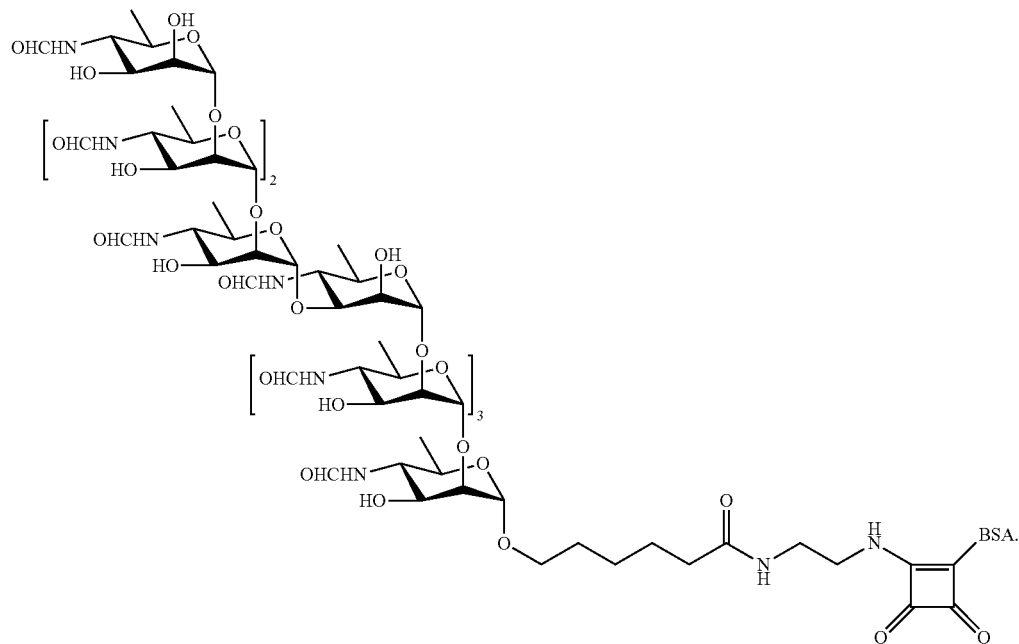

7. A method of detecting the presence of an anti-*Brucella* antibody in a sample, comprising contacting the sample with an antigen comprising a trisaccharide consisting of three units of 4,6-dideoxy-4-formamido-α-D-mannopyranose and comprising only $C_1$-$C_2$ links and/or with an antigen comprising a disaccharide consisting of two units of 4,6-dideoxy-4-formamido-α-D-mannopyranose joined by a $C_1$-$C_2$ link, wherein the trisaccharide or disaccharide is linked to a non-saccharide carrier via the reducing end and wherein the non-saccharide carrier allows the detection of the presence of the antibody in the sample.

8. The method according to claim 7, further comprising contacting the sample with an antigen comprising a monosaccharide consisting of one unit of 4,6-dideoxy-4-formamido-α-D-mannopyranose linked to a non-saccharide carrier via the $C_1$ carbon, wherein the non-saccharide carrier allows the detection of the presence of the antibody in the sample.

9. The method according to claim 7, further comprising contacting the sample with an antigen comprising a tetrasaccharide consisting of four units of 4,6-dideoxy-4-formamido-α-D-mannopyranose and comprising a central $C_1$-$C_3$ link and two $C_1$-$C_2$ links, the tetrasaccharide linked to a non-saccharide carrier via the reducing end, wherein the non-saccharide carrier allows the detection of the presence of an antibody in a sample.

10. The method according to claim 7, wherein (i) the trisaccharide is Structure XII:

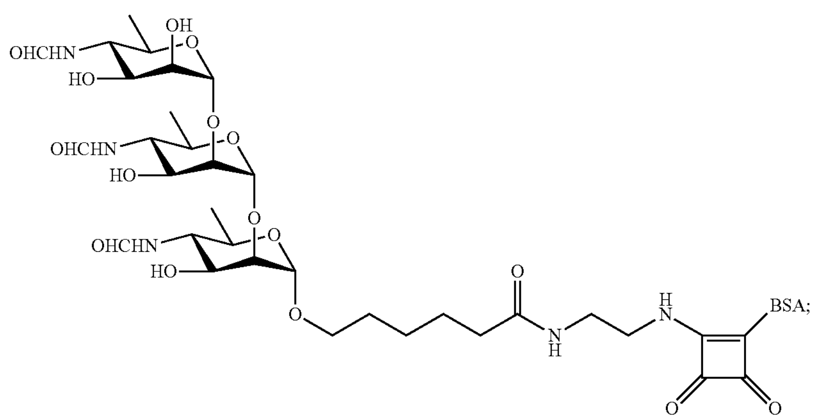

or (ii) the disaccharide is Structure XI:

[Structure XI: disaccharide-linker-BSA conjugate]

11. The method according to claim 8, wherein the monosaccharide is Structure II:

[Structure II: monosaccharide-linker-BSA conjugate]

12. The method according to claim 9, wherein the tetrasaccharide is Structure VI:

[Structure VI: tetrasaccharide-linker-BSA conjugate]

13. The method according to claim 7 for detecting an animal infected with a *Brucella* organism, wherein the method detects an infected animal from within a population of animals known to comprise individuals which have been vaccinated with a molecule comprising a chain of seven or more contiguous units of 4,6-dideoxy-4-formamido-α-D-mannopyranose, adjacent units being joined by a $C_1$-$C_2$ or a $C_1$-$C_3$ link, the chain having a terminal end and a reducing end, wherein the pyranose ring in the unit of the chain most distal from the reducing end is linked to a cap structure, the method comprising contacting a biological sample obtained from the animal with a diagnostic conjugate comprising a trisaccharide consisting of three units of 4,6-dideoxy-4-formamido-α-D-mannopyranose and comprising only $C_1$-$C_2$ links or comprising a disaccharide consisting of two units of 4,6-dideoxy-4-formamido-α-D-mannopyranose joined by a $C_1$-$C_2$ link, wherein the trisaccharide or disaccharide is linked to a non-saccharide carrier via the reducing end and wherein the non-saccharide carrier comprises a protein that allows the detection of the presence of an antibody in a sample, wherein detection of antibody binding to the diagnostic conjugate indicates that the sample was obtained from an animal infected with a *Brucella* organism.

14. The method according to claim 13, wherein the diagnostic conjugate has or comprises:

i) Structure XII:
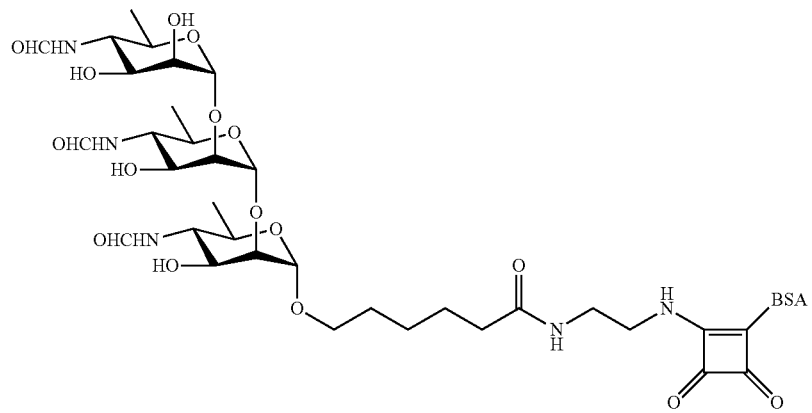
or
ii) Structure XI:
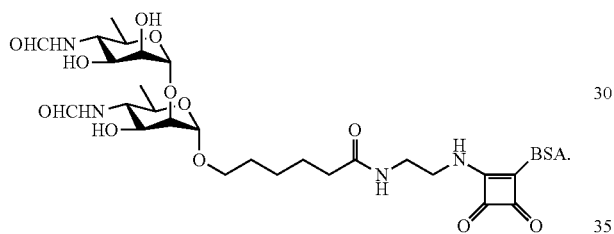
15. A diagnostic conjugate comprising:
Structure XII:
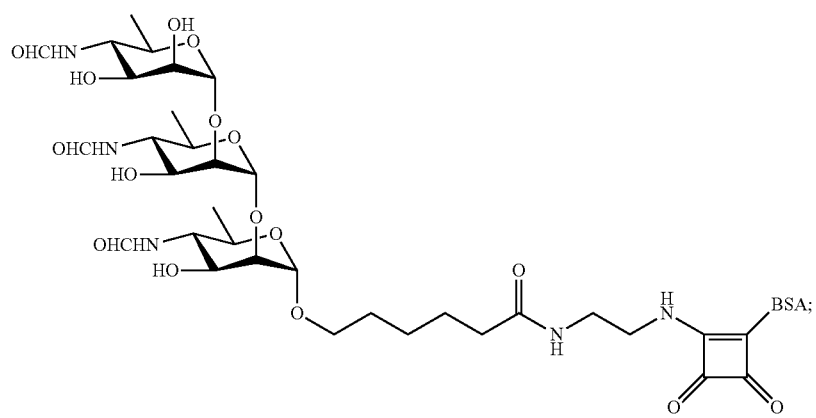

and Structure XI:

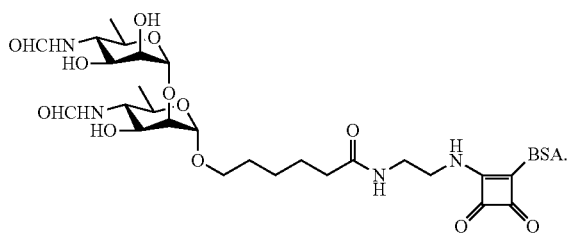

16. A method of detecting the presence of an anti-Brucella antibody in a sample, comprising
    contacting the sample with an antigen comprising a trisaccharide consisting of three units of 4,6-dideoxy-4-formamido-α-D-mannopyranose and comprising only $C_1$-$C_2$ links and/or with an antigen comprising a disaccharide consisting of two units of 4,6-dideoxy-4-formamido-α-D-mannopyranose joined by a $C_1$-$C_2$ link, wherein the trisaccharide or disaccharide is linked to a non-saccharide carrier via the reducing end and
    contacting the sample with an antigen comprising a monosaccharide consisting of one unit of 4,6-dideoxy-4-formamido-α-D-mannopyranose linked to the non-saccharide carrier via the $C_1$ carbon,
    wherein the non-saccharide carrier allows the detection of the presence of the antibody in the sample.

17. The method according to claim 16, wherein the monosaccharide is Structure II:

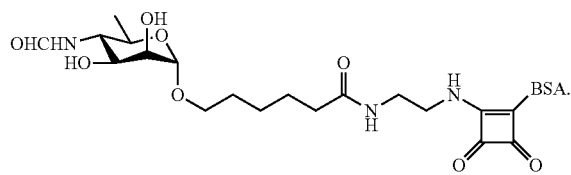

* * * * *